(12) United States Patent
Chamberlain et al.

(10) Patent No.: US 7,655,467 B2
(45) Date of Patent: Feb. 2, 2010

(54) COMPOSITIONS AND METHODS FOR SYSTEMIC NUCLEIC ACID SEQUENCE DELIVERY

(75) Inventors: Jeffrey S. Chamberlain, Seattle, WA (US); Paul Gregorevic, Seattle, WA (US); Michael J. Blankinship, Seattle, WA (US); James M. Allen, Seattle, WA (US)

(73) Assignee: The University of Washington, Seattle, WA (US)

( * ) Notice: Subject to any disclaimer, the term of this patent is extended or adjusted under 35 U.S.C. 154(b) by 0 days.

(21) Appl. No.: 10/988,723

(22) Filed: Nov. 15, 2004

(65) Prior Publication Data

US 2005/0158281 A1    Jul. 21, 2005

Related U.S. Application Data

(60) Provisional application No. 60/520,460, filed on Nov. 14, 2003.

(51) Int. Cl.
*C12N 15/86* (2006.01)
*A61K 48/00* (2006.01)
*A61K 31/70* (2006.01)

(52) U.S. Cl. .................. 435/456; 424/93.2; 514/44
(58) Field of Classification Search ................ 435/456; 424/93.2; 514/44
See application file for complete search history.

(56) References Cited

U.S. PATENT DOCUMENTS

| | | | |
|---|---|---|---|
| 5,239,060 A | 8/1993 | Kunkel et al. | |
| 5,260,209 A | 11/1993 | Campbell et al. | |
| 5,308,752 A | 5/1994 | Campbell et al. | |
| 5,430,129 A | 7/1995 | Campbell et al. | |
| 5,449,616 A | 9/1995 | Campbell et al. | |
| 5,541,074 A | 7/1996 | Kunkel et al. | |
| 5,621,091 A | 4/1997 | Kunkel et al. | |
| 5,686,073 A | 11/1997 | Campbell et al. | |
| 5,863,743 A | 1/1999 | Campbell et al. | |
| 6,156,303 A | 12/2000 | Russell et al. | |
| 6,177,403 B1 | 1/2001 | Stedman | |
| 6,582,692 B1 * | 6/2003 | Podsakoff et al. | 424/93.2 |
| 6,855,701 B2 * | 2/2005 | Lawrence et al. | 514/44 |
| 7,182,944 B2 * | 2/2007 | Bankiewicz | 424/93.2 |

FOREIGN PATENT DOCUMENTS

| | | |
|---|---|---|
| EP | 1059354 | 6/2000 |
| WO | WO9722696 | 6/1997 |
| WO | WO0229056 | 4/2002 |
| WO | WO03052051 | 6/2003 |
| WO | WO03052052 | 6/2003 |

OTHER PUBLICATIONS

Thomas et al. Nature Rev./Genet. 4: 346-358; 2003.*
Brockstedt et al. Clinical Immunol. 92:67-75; 1999.*
Harper et al. Nature Medicine 8: 253-261; 2002.*
Wilson et al. Adv. Drug Deliv. Rev. 46:205-209; 2001.*
Urabe et al. Mol. Ther. 13:823-828; 2006.*
Neufeld et al. FASEB J. 13:9-22, 1999.*
Harper et al. Nature Medicine 8:253-261; 2002.*
Bridges et al., Ann Thorac Surg. Jun. 2002;73(6):1939-46.
Autiero et al., Nat. Med. 2003, 9:936-42.
Houck et al., Mol. Endocrinol., 1991, 5:1806-14.
Wise et al, J. Biol. Chem., 278:38004-14, 2003.
Dvorak et al., J. Histochem. Cytochem., 2001; 49:419-32.
Muller et al., PNAS USA, 1997, 94:7192-7.
Christinger et al., Proteins, 1996, 26:353-7.
Robinson and Stringer, J. Cell. Sci, 2001, 114:853-65.
Chang et al., P. Nat. New Biol. 232:86-87, 1971.
Ma, et al., 2001, Biomed Environ Sci 14:302-311.
Mohanraj et al., 1995, Growth Factors 12:17-27.
Koenig, 1990, J Biol Chem 265:4560-4566.
Rutledge et al., J. Virol., 72:309-19, 1998.
Xiao et al., J. Virology 73:3994-4003, 1999.
Gao et al., 2002, PNAS USA, 99:11854-9.
Chao et al., Mol. Ther. 2:619-623, 2000.
Grimm et al., Mol. Ther., 2003, 7:839-50.
Scott et al., Neuromusc. Disord., 2002, 12(S):S23-S29.
Muzyczka, Curr Top Microbiol. Immunol.1992, 158:97-129.
Collaco et al., Gene, 1999, 238:397-405.
Xiao et al., J. Virol., 1998, 72:2224-32.
Grimm et al, Hum. Gene Ther., 1998, 9:2745-60.
Ferrari et al., Nature Med. 1997, 3:1295-1297.
Rabinowitz et al., J. Virol. 2002, 76:791-801.
Buning et al., Gene Ther., 2003, 10:1142-51.
Hauck and Xiao, J. Virol., 2003, 77:2768-74.
Bowles et al., J. Virol, 2003, 77:423-32.
Wu et al (J. Virol., 2000, 74:8635-47.
Shi et al (Hum. Gene Ther., 2001, 12:1697-711.
Ried et al, J. Virol, 2002, 76:4559-66.

(Continued)

Primary Examiner—Fereydoun G Sajjadi
(74) Attorney, Agent, or Firm—Casimir Jones, S.C.

(57) ABSTRACT

The present invention provides systemic nucleic acid sequence delivery without conventional systemic administration aids (SAAs). In certain embodiments, vascular permeability agents (VPAs), such as VEGF, are used in conjunction with nucleic acid viral vectors, such as adeno-associated virus (AAV). The present invention also provides methods of treating disease by co-administration of nucleic cid sequences encoding Igf-1 and dystrophin or dystrophin-like proteins.

14 Claims, 21 Drawing Sheets

OTHER PUBLICATIONS

Girod et al., Nat. Med., 1999, 5:1052-6.
Grifman et al., Mol. Ther., 2001, 3:964-75.
Yang et al., Hum. Gene Ther., 1998, 9:1929-37).
Haisma et al, Cancer Gene Ther., 200, 7:901-4.
Nicklin et al., Mol. Ther. 2001, 4:174-81.
Terman et al., Growth Factors, 1994, 11:187-95.
Yue, Circulation 108:1626-1632 (2003).
Amalfitano et al., J. Virol. 72:926-933 (1998).
Kumar-Singh et al, Hum. Mol. Genet., 5:913 (1996).
Fisher et al. Virology 217:11-22 (1996).
Kochanek et al., Proc. Nat. Acad. Sci. USA 93:5731-5736 (1996).
Hartigan-O'Connor et al., J. Virol. 73:7835-7841 (1999).
Xie et al., Acta. Crystallogr. D. Bioll. Crystallogr., 2003, 59:959-70.
Yano et al., Methods Mol. Med., 2003, 74:391-8.
Tjwa, et al., Cell Tissue Res. 324:5-15 (2003).
McPherron, Nature. 1997 387:83-90.
Lee et al., Annu Rev Cell Dev Biol. 2004;20:61-86.
Bogdanovich et al., Nature. 2002 420:418-21.
Zhu et al., Cytokine, 2004, 26:262-72 (Abstract only—Article in Chinese).
Harper et al., Nature Med., 8:253-261, 2002.
Phelps et al., Hum. Mol. Gen.; 4(8):1251-1258 (1995).
Hauser and Chamberlain, J. of Endocrinology, 149:373-378 (1996).
Rafael et al., Hum. Mol. Gen., 3(10):1725-1733 (1994).
Cox et al., Nature, 364:725-729 (1993).
Hartigan-O'Conner and Chamberlain, Microscopy Research and Technique, 48:223-238 (Feb. 2000).
Wells et al., Hum. Mol. Genet., 4(8):1245-50 (1995).

* cited by examiner

AAV6-CMV-LacZ

Solid black bar = $10^{12}$ vector genomes delivered with 10 µg V.P.F;
Solid gray bar = $10^{12}$ vector genomes delivered;
Diagonally hashed bars = $2\times10^{11}$ vector genomes delivered with 10 µg V.P.F;
Horizontally hashed bar = $2\times10^{11}$ vector genomes delivered.

FIGURE 13A

Micro-Utrophin DNA Sequence (SEQ ID NO:1)

GCGGCCGCGGTTTTTTTTATCGCTGCCTTGATATACACTTTCCACCATGGCCAAGTATGGGGACCTTGAAGCCAGG
CCTGATGATGGGCAGAACGAATTCAGTGACATCATTAAGTCCAGATCTGATGAACACAATGATGTACAGAAGAAAA
CCTTTACCAAATGGATAAACGCTCGATTTTCCAAGAGTGGGAAACCACCCATCAGTGATATGTTCTCAGACCTCAA
AGATGGGAGAAAGCTCTTGGATCTTCTCGAAGGCCTCACAGGAACATCATTGCCAAAGGAACGTGGTTCCACAAGG
GTGCATGCCTTAAACAATGTCAACCGAGTGCTACAGGTTTTACATCAGAACAATGTGGACTTGGTGAATATTGGAG
GCACGGACATTGTGGATGGAAATCCCAAGCTGACTTTAGGGTTACTCTGGAGCATCATTCTGCACTGGCAGGTGAA
GGATGTCATGAAAGATATCATGTCAGACCTGCAGCAGACAAACAGCGAGAAGATCCTGCTGAGCTGGGTGCGGCAG
ACCACCAGGCCCTACAGTCAAGTCAACGTCCTCAACTTCACCACCAGCTGGACCGATGGACTCGCGTTCAACGCCG
TGCTCCACCGGCACAAACCAGATCTCTTCAGCTGGGACAGAGTGGTCAAAATGTCCCCAATTGAGAGACTTGAACA
TGCTTTTAGCAAGGCCCACACTTATTTGGGAATTGAAAAGCTTCTAGATCCTGAAGATGTTGCTGTGCATCTCCCT
GACAAGAAATCCATAATTATGTATTTAACGTCTCTGTTTGAGGTGCTTCCTCAGCAAGTCACGATAGATGCCATCC
GAGAGGTGGAGACTCTCCCAAGGAAGTATAAGAAAGAATGTGAAGAGGAAGAAATTCATATCCAGAGTGCAGTGCT
GGCAGAGGAAGGCCAGAGTCCCCGAGCTGAGACCCCTAGCACCGTCACTGAAGTGGACATGGATTTGGACAGCTAC
CAGATAGCGCTAGAGGAAGTGCTGACGTGGCTGCTGTCCGCGGAGGACACGTTCCAGGAGCAAGATGACATTTCTG
ATGATGTCGAAGAAGTCAAAGAGCAGTTTGCTACCCATGAAACTTTTATGATGGAGCTGACAGCACACCAGAGCAG
CGTGGGGAGCGTCCTGCAGGCTGGCAACCAGCTGATGACACAAGGGACTCTGTCAGAGGAGGAGGAGTTTGAGATC
CAGGAACAGATGACCTTGCTGAATGCAAGGTGGGAGGCGCTCCGGGTGGAGAGCATGGAGAGGCAGTCCCGGCTGC
ACGACGCTCTGATGGAGCTGCAGAAGAAACAGCTGCAGCAGCTCTCAAGCTGGCTGGCCCTCACAGAAGAGCGCAT
TCAGAAGATGGAGAGCCTCCCGCTGGGTGATGACCTGCCCTCCCTGCAGAAGCTGCTTCAAGAACATAAAAGTTTG
CAAAATGACCTTGAAGCTGAACAGGTGAAGGTAAATTCCTTAACTCACATGGTGGTGATTGTGGATGAAAACAGTG
GGGAGAGTGCCACAGCTCTTCTGGAAGATCAGTTACAGAAACTGGGTGAGCGCTGGACAGCTGTATGCCGCTGGAC
TGAAGAACGTTGGAACAGGTTGCAAGAAATCAGTATTCTGTGGCAGGAATTATTGGAAGAGCAGTGTCTGTTGGAG
GCTTGGCTCACCGAAAAGGAAGAGGCTTTGAATAAAGTTCAAACCAGCAACTTTAAAGACCAGAAGGAACTAAGTG
TCAGTGTCCGGCGTCTGGCTATATTGAAGGAAGACATGGAAATGAAGAGGCAGACTCTGGATCAACTGAGTGAGAT
TGGCCAGGATGTGGGCCAATTACTCAGTAATCCCAAGGCATCTAAGAAGATGAACAGTGACTCTGAGGAGCTAACA
CAGAGATGGGATTCTCTGGTTCAGAGACTCGAAGACTCTTCTAACCAGGTGACTCAGGCGGTAGCGAAGCTCGGCA
TGTCCCAGATTCCACAGAAGGACCTATTGGAGACCGTTCATGTGAGAGAACAAGGGATGGTGAAGAAGCCCAAGCA
GGAACTGCCTCCTCCTCCCCCACCAAAGAAGAGACAGATTCACGTGGACTTAGAGAAACTCCGAGACCTGCAGGGA
GCTATGGACGACCTGGACGCAGACATGAAGGAGGTGGAGGCTGTGCGGAATGGCTGGAAGCCCGTGGGAGACCTGC
TTATAGACTCCCTGCAGGATCACATCGAGAAACCCTGGCGTTTAGAGAAGAAATTGCACCAATCAACTTAAAAGT
AAAAACAATGAATGACCTGTCCAGTCAGCTGTCTCCACTTGACTTGCATCCATCTCTAAAGATGTCTCGCCAGCTG
GATGACCTTAATATGCGATGGAAACTTCTACAGGTTTCCGTGGACGATCGCCTTAAGCAGCTCCAGGAAGCCCACA
GAGATTTTGGGCCATCTTCTCAACACTTTCTGTCCACTTCAGTCCAGCTGCCGTGGCAGAGATCCATTTCACATAA
TAAAGTGCCCTATTACATCAACCATCAAACACAGACAACCTGTTGGGATCATCCTAAAATGACTGAGCTCTTCCAA
TCCCTTGCTGATCTGAATAATGTACGTTTCTCTGCCTACCGCACAGCAATCAAAATTCGAAGGCTGCAAAAAGCAT
TATGTCTGGATCTCTTAGAGCTGAATACGACGAATGAAGTTTTCAAGCAGCACAAACTGAACCAAAATGATCAGCT
CCTGAGTGTCCCAGACGTCATCAACTGTCTGACCACCACTTACGATGGGCTTGAGCAGCTGCACAAGGACTTGGTC
AATGTTCCACTCTGCGTCGATATGTGTCTCAACTGGCTGCTCAACGTATACGACACGGGCCGGACTGGAAAAATTC
GGGTACAGAGTCTGAAGATTGGATTGATGTCTCTCTCCAAAGGCCTCTTAGAAGAGAAATACAGATGTCTCTTTAA
GGAGGTGGCAGGGCCAACAGAGATGTGTGACCAGCGGCAGCTTGGCCTGCTACTTCACGATGCCATCCAGATCCCT
AGGCAGCTGGGGGAAGTAGCAGCCTTTGGGGGCAGTAACATTGAGCCCAGTGTCCGCAGCTGCTTCCAGCAGAATA
ACAACAAGCCAGAAATCAGTGTGAAGGAGTTTATAGACTGGATGCATTTGGAACCCCAGTCCATGGTGTGGTTGCC
GGTTCTGCATCGGGTCGCAGCTGCTGAGACTGCAAAACATCAGGCCAAATGCAACATCTGCAAAGAATGCCCGATT
GTTGGGTTCAGATACAGGAGCCTAAAGCATTTTAATTATGATGTCTGCCAGAGTTGCTTCTTTTCTGGAAGAACAG
CAAAGGGCCACAAGTTACATTACCCGATGGTAGAATACTGCATACAGGCAATGTAGGAAGTCTTTTCCACATGGCA
GATGATTTGGGCAGAGCGATGGAGTCCTTAGTATCAGTCATGACAGATGAAGAAGGAGCAGAATAAATGTTTTACA
ACTCCTGATTCCCGCATGCGGCCGC

FIGURE 13B

Micro-Utrophin DNA Sequence (SEQ ID NO:2)

```
GCGGCCGCGGTTTTTTTTATCGCTGCCTTGATATACACTTTCCACCATGGCCAAGTATGGGGACCTTGAAGCCAGG
CCTGATGATGGGCAGAACGAATTCAGTGACATCATTAAGTCCAGATCTGATGAACACAATGATGTACAGAAGAAAA
CCTTTACCAAATGGATAAACGCTCGATTTTCCAAGAGTGGGAAACCACCCATCAGTGATATGTTCTCAGACCTCAA
AGATGGGAGAAAGCTCTTGGATCTTCTCGAAGGCCTCACAGGAACATCATTGCCAAAGGAACGTGGTTCCACAAGG
GTGCATGCCTTAAACAATGTCAACCGAGTGCTACAGGTTTTACATCAGAACAATGTGGACTTGGTGAATATTGGAG
GCACGGACATTGTGGATGGAAATCCCAAGCTGACTTTAGGGTTACTCTGGAGCATCATTCTGCACTGGCAGGTGAA
GGATGTCATGAAAGATATCATGTCAGACCTGCAGCAGACAAACAGCGAGAAGATCCTGCTGAGCTGGGTGCGGCAG
ACCACCAGGCCCTACAGTCAAGTCAACGTCCTCAACTTCACCACCAGCTGGACCGATGGACTCGCGTTCAACGCCG
TGCTCCACCGGCACAAACCAGATCTCTTCAGCTGGGACAGAGTGGTCAAAATGTCCCCAATTGAGAGACTTGAACA
TGCTTTTAGCAAGGCCCACACTTATTTGGGAATTGAAAAGCTTCTAGATCCTGAAGATGTTGCTGTGCATCTCCCT
GACAAGAAATCCATAATTATGTATTTAACGTCTCTGTTTGAGGTGCTTCCTCAGCAAGTCACGATAGATGCCATCC
GAGAGGTGGAGACTCTCCCAAGGAAGTATAAGAAAGAATGTGAAGAGGAAGAAATTCATATCCAGAGTGCAGTGCT
GGCAGAGGAAGGCCAGAGTCCCCGAGCTGAGACCCCTAGCACCGTCACTGAAGTGGACATGGATTTGGACAGCTAC
CAGATAGCGCTAGAGGAAGTGCTGACGTGGCTGCTGTCCGCGGAGGACACGTTCCAGGAGCAAGATGACATTTCTG
ATGATGTCGAAGAAGTCAAAGAGCAGTTTGCTACCCATGAAACTTTTATGATGGAGCTGACAGCACACCAGAGCAG
CGTGGGGAGCGTCCTGCAGGCTGGCAACCAGCTGATGACACAAGGGACTCTGTCAGAGGAGGAGGAGTTTGAGATC
CAGGAACAGATGACCTTGCTGAATGCAAGGTGGGAGGCGCTCCGGGTGGAGAGCATGGAGAGGCAGTCCCGGCTGC
ACGACGCTCTGATGGAGCTGCAGAAGAAACAGCTGCAGCAGCTCTCAAGCTGGCTGGCCCTCACAGAAGAGCGCAT
TCAGAAGATGGAGAGCCTCCCGCTGGGTGATGACCTGCCCTCCCTGCAGAAGCTGCTTCAAGAACATAAAAGTTTG
CAAAATGACCTTGAAGCTGAACAGGTGAAGGTAAATTCCTTAACTCACATGGTGGTGATTGTGGATGAAAACAGTG
GGGAGAGTGCCACAGCTCTTCTGGAAGATCAGTTACAGAAACTGGGTGAGCGCTGGACAGCTGTATGCCGCTGGAC
TGAAGAACGTTGGAACAGGTTGCAAGAAATCAGTATTCTGTGGCAGGAATTATTGGAAGAGCAGTGTCTGTTGGAG
GCTTGGCTCACCGAAAAGGAAGAGGCTTTGAATAAAGTTCAAACCAGCAACTTTAAAGACCAGAAGGAACTAAGTG
TCAGTGTCCGGCGTCTGGCTATATTGAAGGAAGACATGGAAATGAAGAGGCAGACTCTGGATCAACTGAGTGAGAT
TGGCCAGGATGTGGGCCAATTACTCAGTAATCCCAAGGCATCTAAGAAGATGAACAGTGACTCTGAGGAGCTAACA
CAGAGATGGGATTCTCTGGTTCAGAGACTCGAAGACTCTTCTAACCAGGTGACTCAGGCGGTAGCGAAGCTCGGCA
TGTCCCAGATTCCACAGAAGGACCTATTGGAGACCGTTCATGTGAGAGAACAAGGGATGGTGAAGAAGCCCAAGCA
GGAACTGCCTCCTCCTCCCCCACCAAAGAAGAGACAGATTCACGTGGACTTAGAGAAACTCCGAGACCTGCAGGGA
GCTATGGACGACCTGGACGCAGACATGAAGGAGGTGGAGGCTGTGCGGAATGGCTGGAAGCCCGTGGGAGACCTGC
TTATAGACTCCCTGCAGGATCACATCGAGAAACCCTGGCGTTTAGAGAAGAAATTGCACCAATCAACTTAAAAGT
AAAAACAATGAATGACCTGTCCAGTCAGCTGTCTCCACTTGACTTGCATCCATCTCTAAAGATGTCTCGCCAGCTG
GATGACCTTAATATGCGATGGAAACTTCTACAGGTTTCCGTGGACGATCGCCTTAAGCAGCTCCAGGAAGCCCACA
GAGATTTTGGGCCATCTTCTCAACACTTTCTGTCCACTTCAGTCCAGCTGCCGTGGCAGAGATCCATTTCACATAA
TAAAGTGCCCTATTACATCAACCATCAAACACAGACAACCTGTTGGGATCATCCTAAAATGACTGAGCTCTTCCAA
TCCCTTGCTGATCTGAATAATGTACGTTTCTCTGCCTACCGCACAGCAATCAAAATTCGAAGGCTGCAAAAAGCAT
TATGTCTGGATCTCTTAGAGCTGAATACGACGAATGAAGTTTTCAAGCAGCACAAACTGAACCAAAATGATCAGCT
CCTGAGTGTCCCAGACGTCATCAACTGTCTGACCACCACTTACGATGGGCTTGAGCAGCTGCACAAGGACTTGGTC
AATGTTCCACTCTGCGTCGATATGTGTCTCAACTGGCTGCTCAACGTATACGACACGGGCCGGACTGGAAAAATTC
GGGTACAGAGTCTGAAGATTGGATTGATGTCTCTCTCCAAAGGCCTCTTAGAAGAGAAATACAGATGTCTCTTTAA
GGAGGTGGCAGGGCCAACAGAGATGTGTGACCAGCGGCAGCTTGGCCTGCTACTTCACGATGCCATCCAGATCCCT
AGGCAGCTGGGGGAAGTAGCAGCCTTTGGGGGCAGTAACATTGAGCCCAGTGTCCGCAGCTGCTTCCAGCAGAATA
ACAACAAGCCAGAAATCAGTGTGAAGGAGTTTATAGACTGGATGCATTTGGAACCCCAGTCCATGGTGTGGTTGCC
GGTTCTGCATCGGGTCGCAGCTGCTGAGACTGCAAAACATCAGGCCAAATGCAACATCTGCAAAGAATGCCCGATT
GTTGGGTTCAGATACAGGAGCCTAAAGCATTTTAATTATGATGTCTGCCAGAGTTGCTTCTTTTCTGGAAGAACAG
CAAAGGGCCACAAGTTACATTACCCGATGGTAGAATACTGCATACCGACAACATCTGGGGAAGATGTGAGAGATTT
CACTAAGGTGCTGAAGAACAAGTTCAGGTCCAAGAAATATTTTGCCAAACATCCTCGGCTTGGCTACCTGCCTGTC
CAGACCGTGCTGGAAGGGGACAACTTAGAAACTAGGCCACAGGCAATGTAGGAAGTCTTTTCCACATGGCAGATGA
TTTGGGCAGAGCGATGGAGTCCTTAGTATCAGTCATGACAGATGAAGAAGGAGCAGAATAAATGTTTTACAACTCC
TGATTCCCGCATGCGGCCGC
```

FIGURE 13C

Human Micro-Utrophin DNA Sequence (SEQ ID NO:6)

ATGGCCAAGTATGGAGAACATGAAGCCAGTCCTGACAATGGGCAGAACGAATTCAGTGATATCATTAAGTCCAGAT
CTGATGAACACAATGACGTACAGAAGAAAACCTTTACCAAATGGATAAATGCTCGATTTTCAAAGAGTGGGAAACC
ACCCATCAATGATATGTTCACAGACCTCAAAGATGGAAGGAAGCTATTGGATCTTCTAGAAGGCCTCACAGGAACA
TCACTGCCAAAGGAACGTGGTTCCACAAGGGTACATGCCTTAAATAACGTCAACAGAGTGCTGCAGGTTTTACATC
AGAACAATGTGGAATTAGTGAATATAGGGGAACTGACATTGTGGATGGAAATCACAAACTGACTTTGGGGTTACT
TTGGAGCATCATTTTGCACTGGCAGGTGAAAGATGTCATGAAGGATGTCATGTCGGACCTGCAGCAGACGAACAGT
GAGAAGATCCTGCTCAGCTGGGTGCGTCAGACCACCAGGCCCTACAGCCAAGTCAACGTCCTCAACTTCACCACCA
GCTGGACAGATGGACTCGCCTTTAATGCTGTCCTCCACCGACATAAACCTGATCTCTTCAGCTGGGATAAAGTTGT
CAAAATGTCACCAATTGAGAGACTTGAACATGCCTTCAGCAAGGCTCAAACTTATTTGGGAATTGAAAAGCTGTTA
GATCCTGAAGATGTTGCCGTTCGGCTTCCTGACAAGAAATCCATAATTATGTATTTAACATCTTTGTTGAGGTGC
TACCTCAGCAAGTCACCATAGACGCCATCCGTGAGGTAGAGACACTCCCAAGGAAATATAAAAAAGAATGTGAAGA
AGAGGCAATTAATATACAGAGTACAGCGCCTGAGGAGGAGCATGAGAGTCCCCGAGCTGAAACTCCCAGCACTGTC
ACTGAGGTCGACATGGATCTGGACAGCTATCAGATTGCGTTGGAGGAAGTGCTGACCTGGTTGCTTTCTGCTGAGG
ACACTTTCCAGGAGCAGGATGATATTTCTGATGATGTTGAAGAAGTCAAAGACCAGTTTGCAACCCATGAAGCTTT
TATGATGGAACTGACTGCACACCAGAGCAGTGTGGGCAGCGTCCTGCAGGCAGGCAACCAACTGATAACACAAGGA
ACTCTGTCAGACGAAGAAGAATTTGAGATTCAGGAACAGATGACCCTGCTGAATGCTAGATGGGAGGCTCTTAGGG
TGGAGAGTATGGACAGACAGTCCCGGCTGCACGATGTGCTGATGGAACTGCAGAAGAAGCAACTGCAGCAGCTCTC
CGCCTGGTTAACACTCACAGAGGAGCGCATTCAGAAGATGGAAACTTGCCCCCTGGATGATGATGTAAAATCTCTA
CAAAAGCTGCTAGAAGAACATAAAAGTTTGCAAAGTGATCTTGAGGCTGAACAGGTGAAAGTAAATTCACTAACTC
ACATGGTGGTCATTGTTGATGAAAACAGTGGTGAGAGCGCTACAGCTATCCTAGAAGACCAGTTACAGAAACTTGG
TGAGCGCTGGACAGCAGTATGCCGTTGGACTGAAGAACGCTGGAATAGGTTACAAGAAATCAATATATTGTGGCAG
GAATTATTGGAAGAACAGTGCTTGTTGAAAGCTTGGTTAACCGAAAAAGAAGAGGCTTTAAATAAAGTCCAGACAA
GCAACTTCAAAGACCAAAAGGAACTAAGTGTCAGTGTTCGACGTCTGGCTATTTTGAAGGAAGACATGGAAATGAA
GCGTCAAACATTGGATCAGCTGAGTGAGATTGGCCAGGATGTGGGACAATTACTTGATAATTCCAAGGCATCAAG
AAGATCAACAGTGACTCAGAGGAACTGACTCAAAGATGGGATTCTTTGGTTCAGAGACTAGAAGATTCCTCCAACC
AGGTGACTCAGGCTGTAGCAAAGCTGGGGATGTCTCAGATTCCTCAGAAGGACCTTTTGGAGACTGTTCGTGTAAG
AGAACAAGCAATTACAAAAAAATCTAAGCAGGAACTGCCTCCTCCTCCTCCCCAAAGAAGAGACAGATCCATGTG
GATTTGGAGAAACTCAGAGACCTGCAGGGAGCTATGATGACCTGGACGCTGACATGAAGGAGGCAGAGTCCGTGC
GGAATGGCTGGAAGCCCGTGGGAGACTTACTCATTGACTCGCTGCAGGATCACATTGAAAAAATCATGGCATTTAG
AGAAGAAATTGCACCAATCAACTTTAAAGTTAAAACGGTGAATGATTTATCCAGTCAGCTGTCTCCACTTGACCTG
CATCCCTCTCTAAAGATGTCTCGCCAGCTAGATGACCTTAATATGCGATGGAAACTTTTACAGGTTTCTGTGGATG
ATCGCCTTAAACAGCTTCAGGAAGCCCACAGAGATTTTGGACCATCCTCTCAGCATTTTCTCTCTACGTCAGTCCA
GCTGCCGTGGCAAAGATCCATTTCACATAATAAAGTGCCCTATTACATCAACCATCAAACACAGACCACCTGTTGG
GACCATCCTAAAATGACCGAACTCTTTCAATCCCTTGCTGACCTGAATAATGTACGTTTTTCTGCCTACCGTACAG
CAATCAAAATCCGAAGACTACAAAAAGCACTATGTTTGGATCTCTTAGAGTTGAGTACAACAAATGAAATTTTCAA
ACAGCACAAGTTGAACCAAAATGACCAGCTCCTCAGTGTTCCAGATGTCATCAACTGTCTGACAACAACTTATGAT
GGACTTGAGCAAATGCATAAGGACCTGGTCAACGTTCCACTCTGTGTTGATATGTGTCTCAATTGGTTGCTCAATG
TCTATGACACGGGTCGAACTGGAAAAATTAGAGTGCAGAGTCTGAAGATTGGATTAATGTCTCTCTCCAAAGGTCT
CTTGGAAGAAAATACAGATATCTCTTTAAGGAAGTTGCGGGGCCGACAGAAATGTGTGACCAGAGGCAGCTGGGC
CTGTTACTTCATGATGCCATCCAGATCCCCCGGCAGCTAGGTGAAGTAGCAGCTTTTGGAGGCAGTAATATTGAGC
CTAGTGTTCGCAGCTGCTTCCAACAGAATAACAATAAACCAGAAATAAGTGTGAAAGAGTTTATAGATTGGATGCA
TTTGGAACCACAGTCCATGGTTTGGCTCCCAGTTTTACATCGAGTGGCAGCAGCGGAGACTGCAAAACATCAGGCC
AAATGCAACATCTGTAAAGAATGTCCAATTGTCGGGTTCAGGTATAGAAGCCTTAAGCATTTTAACTATGATGTCT
GCCAGAGTTGTTTCTTTTCGGGTCGAACAGCAAAAGGTCACAAATTACATTACCCAATGGTGGAATATTGTATACC
TACAACATCTGGGGAAGATGTACGAGACTTCACAAAGGTACTTAAGAACAAGTTCAGGTCGAAGAAGTACTTTGCC
AAACACCCTCGACTTGGTTACCTGCCTGTCCAGACAGTTCTTGAAGGTGACAACTTAGAGACTAGGCCACAGGCAA
TGTAG

FIGURE 14
A.  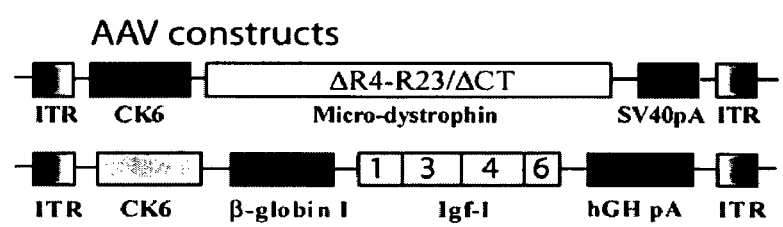
B. 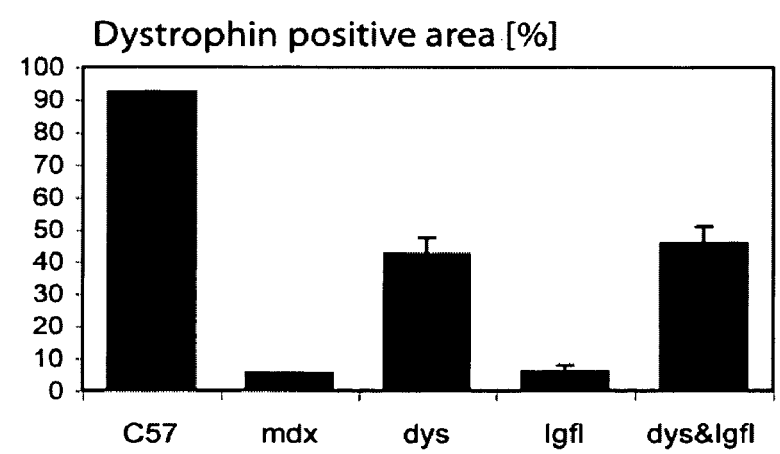

FIGURE 16
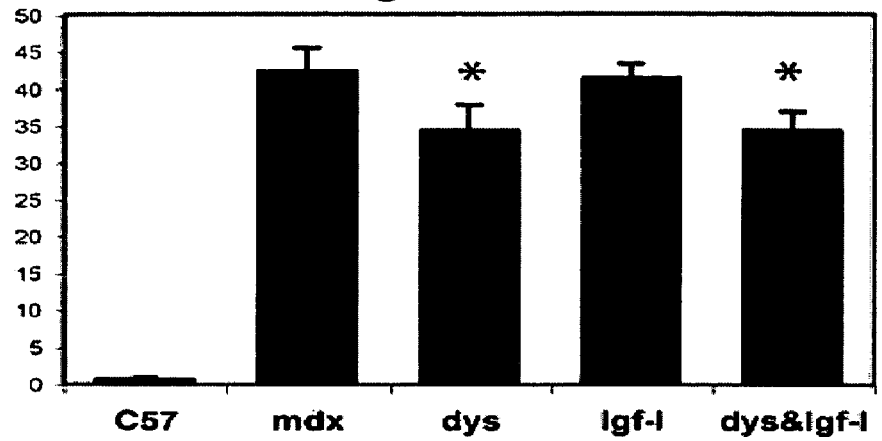
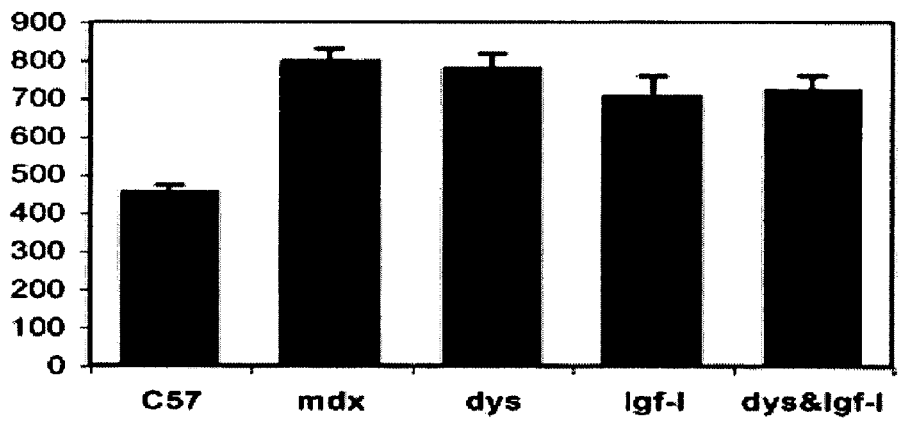
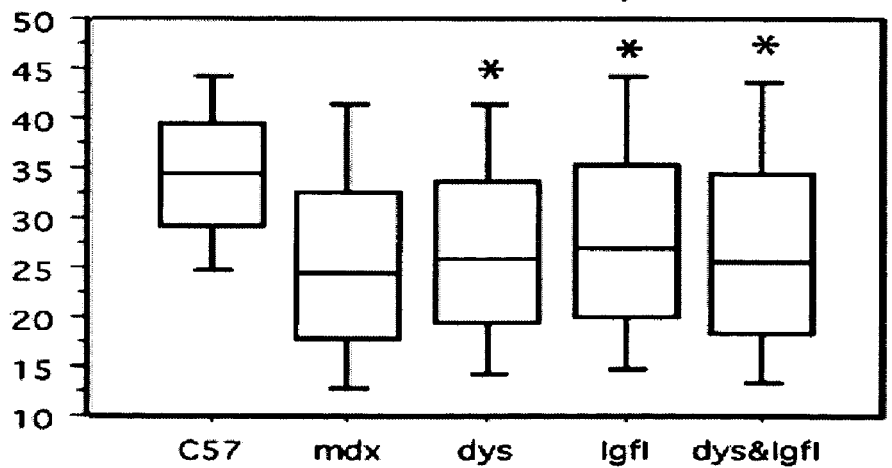

FIGURE 17
A.
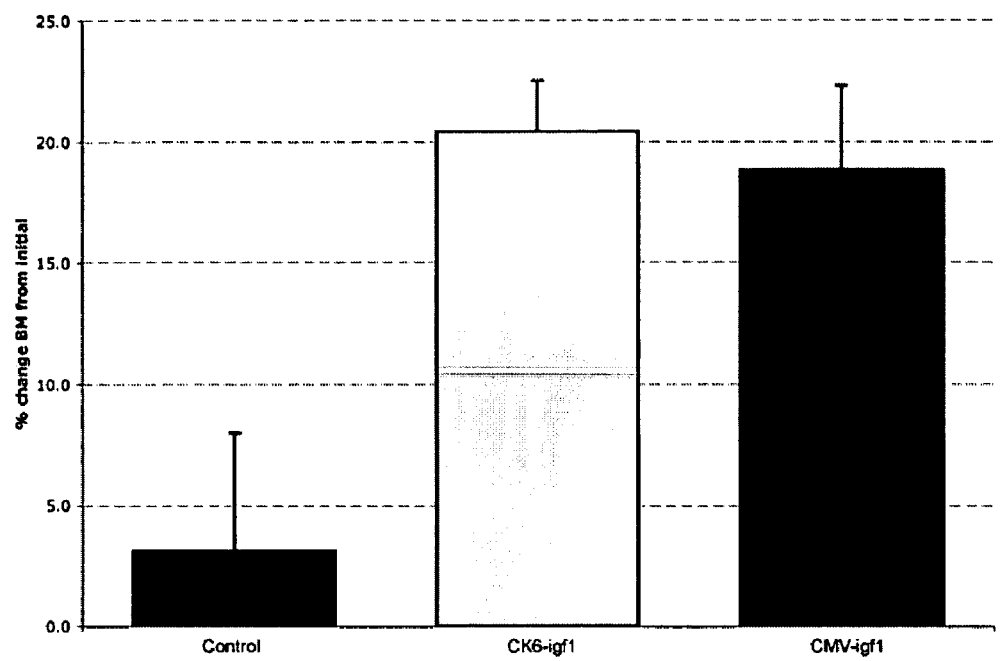
B.
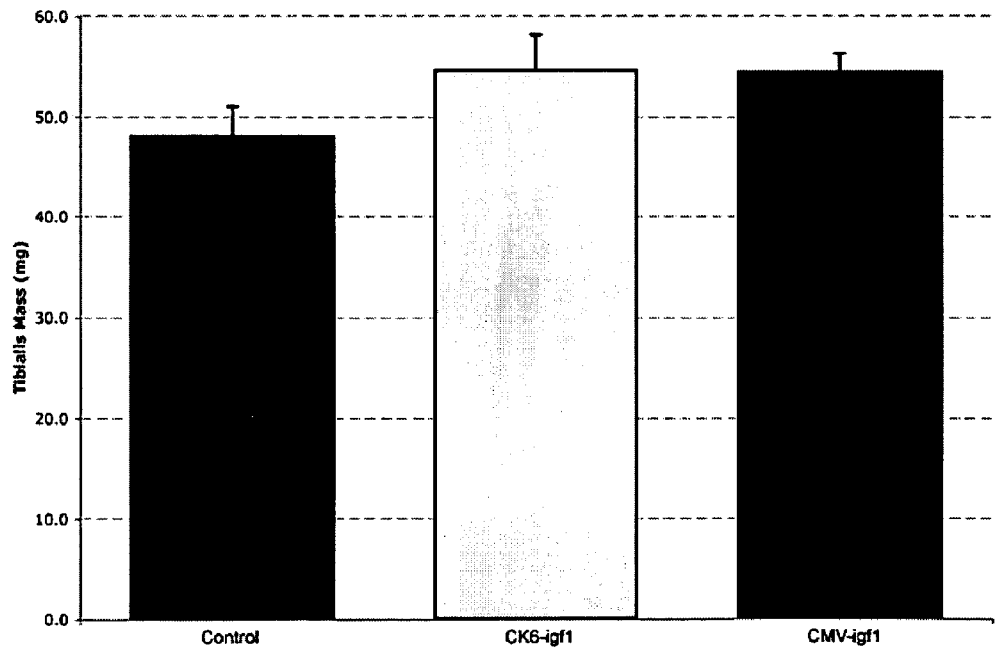

FIGURE 18
A. The tibialis anterior (TA) muscles of treated old mice generate increased force compared with the muscles of untreated mice
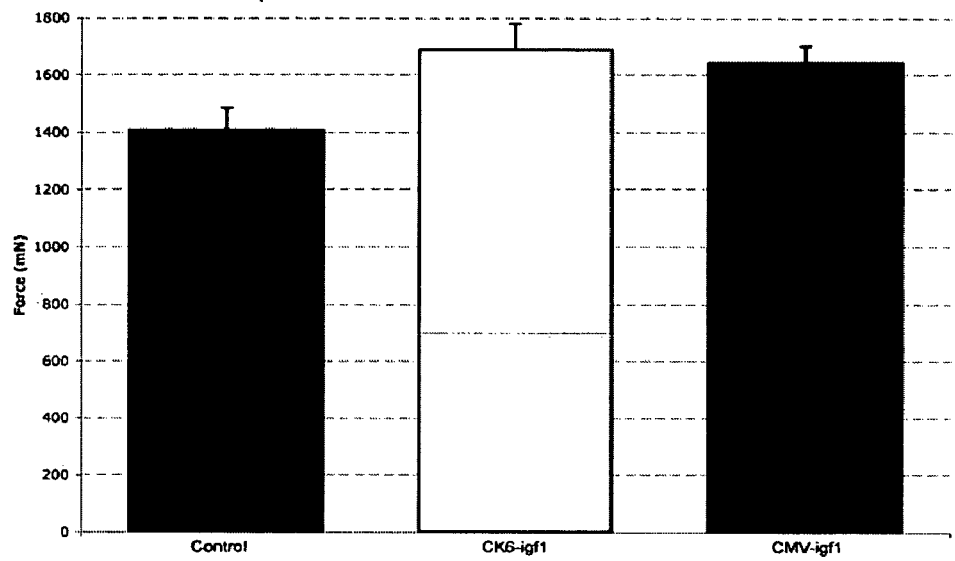
B. The muscles of treated mice display increased force output over a protocol of repetitive stimulation, and at recovery
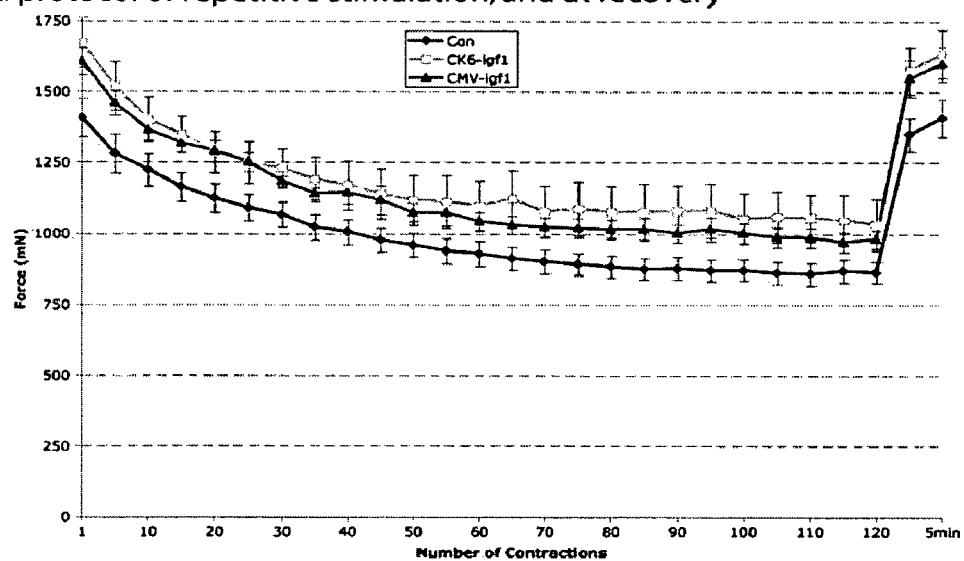

FIGURE 19

Murine Igf-I Eb (SEQ ID NO:3)

ATTGCTCTAACATCTCCCATCTCTCTGGATTTCTTTTTCGCCTCATTATCCCTGCCCACCAATTCATTTCCAGACT
TTGTACTTCAGAAGCGATGGGGAAAATCAGCAGCCTTCCAACTCAATTATTTAAGATCTGCCTCTGTGACTTCTTG
AAGATAAAGATACACATCATGTCGTCTTCACACCTCTTCTACCTGGCGCTCTGCTTGCTCACCTTCACCAGCTCCA
CCACAGCTGGACCAGAGACCCTTTGCGGGGCTGAGCTGGTGGATGCTCTTCAGTTCGTGTGTGGACCGAGGGGCTT
TTACTTCAACAAGCCCACAGGCTATGGCTCCAGCATTCGGAGGGCACCTCAGACAGGCATTGTGGATGAGTGTTGC
TTCCGGAGCTGTGATCTGAGGAGACTGGAGATGTACTGTGCCCCACTGAAGCCTACAAAAGCAGCCCGCTCTATCC
GTGCCCAGCGCCACACTGACATGCCCAAGACTCAGAAGTCCCGTCCCTATCGACAAACAAGAAAACGAAGCTGCA
AAGGAGAAGGAAAGGAAGTACATTTGAAGAACACAAGTAGAGGAAGTGCAGGAAACAAGACCTACAGAATGTAGGA
GGAGCCTCCCACGGAGCAGGAAATGCCACATCACCGCAGGATCCTTTGCTGCTTGAGCAACCTGCAAAACATCGAA
ACACCTACCAAATAACAATAATAAGTCCAATAACATTACAAAGATGGGCATTTCCCCCAATGAAATATACAAGTAA
ACATT

Murine Igf-I Ea (SEQ ID NO:4)

ATTGCTCTAACATCTCCCATCTCTCTGGATTTCTTTTTCGCCTCATTATCCCTGCCCACCAATTCATTTCCAGACT
TTGTACTTCAGAAGCGATGGGGAAAATCAGCAGCCTTCCAACTCAATTATTTAAGATCTGCCTCTGTGACTTCTTG
AAGATAAAGATACACATCATGTCGTCTTCACACCTCTTCTACCTGGCGCTCTGCTTGCTCACCTTCACCAGCTCCA
CCACAGCTGGACCAGAGACCCTTTGCGGGGCTGAGCTGGTGGATGCTCTTCAGTTCGTGTGTGGACCGAGGGGCTT
TTACTTCAACAAGCCCACAGGCTATGGCTCCAGCATTCGGAGGGCACCTCAGACAGGCATTGTGGATGAGTGTTGC
TTCCGGAGCTGTGATCTGAGGAGACTGGAGATGTACTGTGCCCCACTGAAGCCTACAAAAGCAGCCCGCTCTATCC
GTGCCCAGCGCCACACTGACATGCCCAAGACTCAGAAGGAAGTACATTTGAAGAACACAAGTAGAGGAAGTGCAGG
AAACAAGACCTACAGAATGTAGGAGGAGCCTCCCACGGAGCAGAAAATGCCACATCACCGCAGGATCCTTTGCTGC
TTGAGCAACCTGCAAAACATCGAAACACCTACCAAATAACAATAATAAGTCCAATAACATTACAAAGATGGGCATT
TCCCCCAATGAAATATACAAGTAAACATT

Human Igf-I (SEQ ID NO:5)

TTCAGAGCAGATAGAGCCTGCGCAATGGAATAAAGTCCTCAAAATTGAAATGTGACATTGCTCTCAACATCTCCCA
TCTCTCTGGATTTCTTTTTGCTTCATTATTCCTGCTAACCAATTCATTTTCAGACTTTGTACTTCAGAAGCAATGG
GAAAAATCAGCAGTCTTCCAACCCAATTATTTAAGTGCTGCTTTTGTGATTTCTTGAAGGTGAAGATGCACACCAT
GTCCTCCTCGCATCTCTTCTACCTGGCGCTGTGCCTGCTCACCTTCACCAGCTCTGCCACGGCTGGACCGGAGACG
CTCTGCGGGGCTGAGCTGGTGGATGCTCTTCAGTTCGTGTGTGGAGACAGGGGCTTTTATTTCAACAAGCCCACAG
GGTATGGCTCCAGCAGTCGGAGGGCGCCTCAGACAGGCATCGTGGATGAGTGCTGCTTCCGGAGCTGTGATCTAAG
GAGGCTGGAGATGTATTGCGCACCCCTCAAGCCTGCCAAGTCAGCTCGCTCTGTCCGTGCCCAGCGCCACACCGAC
ATGCCCAAGACCCAGAAGGAAGTACATTTGAAGAACGCAAGTAGAGGGAGTGCAGGAAACAAGAACTACAGGATGT
AGGAAGACCCTCCTGAGGAGTGAAGAGTGACATGCCACCGCAGGATCCTTTGCTCTGCACGAGTTACCTGTTAAAC
TTTGGAACACCTACCAAAAAATAAGTTTGATAACATTTAAAAGATGGGCGTTTCCCCCAATGAAATACACAAGTAA
ACTTCCAACATTGTCTTTAGGAGTGATTTGCACCTTGCAAAAATGGTCCTGGAGTTGGTAGATTGCTGTTGATCTT
TTATCAATAATGTTCTATAGAAAAGAAAAAAAAATTATATATATATATATATCTTAGTCCCTGCCTCTCAAGAGC
CACAAATGCATGGGTGTTGTATAGATCCAGTTGCACTAAATTCCTCTCTGAATCTTGGCTGCTGGAGCCATTCATT
CAGCAACCTTGTCTAAGTGGTTTATGAATTGTTTCCTTATTTGCACTTCTTTCTACACAACTCGGGCTGTTTGTTT
TACAGTGTCTGA

COMPOSITIONS AND METHODS FOR SYSTEMIC NUCLEIC ACID SEQUENCE DELIVERY

The present Application claims priority to U.S. Provisional Application 60/520,460 filed Nov. 14, 2003, which is herein incorporated by reference.

The present application was funded in part with government support under grant numbers 5 R01 AR0 44533-08 and 2 P01 AG015434-06 from the National Institutes of Health. The government has certain rights in this invention.

FIELD OF THE INVENTION

The present invention relates to compositions, methods and kits for systemic nucleic acid sequence delivery. In particular, the present invention relates to systemic nucleic acid sequence delivery without conventional systemic administration aids (SAAs). In certain embodiments, vascular permeability agents (VPAs), such as VEGF, are used in conjunction with nucleic acid viral vectors, such as adeno-associated virus (AAV). The present invention also provides methods of treating disease by co-administration of nucleic cid sequences encoding Igf-1 and dystrophin or dystrophin-like proteins.

BACKGROUND OF THE INVENTION

Delivery of a therapeutic transgene to cells widely distributed throughout the body (such as skeletal muscle, nerves, skin, bone or fat) via a systemic route has traditionally proven ineffective. From attempts to utilize the intravascular route for systemic delivery to skeletal muscle fibers, it has been determined that the vascular endothelium represents the critical barrier to dispersion of vectors beyond the bloodstream. Early approaches attempting to overcome cellular barriers utilized methods of mechanical disruption of cell membranes (e.g. electrical field poration, high energy ultrasound, or extra-cellular matrix degrading agents) that were accompanied by considerable tissue damage. These methods are presently considered either unsuitable for clinical development, or present limited potential for scaling to human application. More recent strategies employed to breach the endothelial barrier in vivo, rely on dramatically elevated hydrostatic pressure, coupled with pre-treatments incorporating potent pharmacological agents to increase the blood flow within a limited number of select target tissues, and enhance local vascular permeability (typically papaverine and histamine, respectively).

The clinical potential of these methodologies is severely limited owing to the considerable risks of adverse effects imposed on frail patients by the current techniques (e.g. acute hypertension-related events, profound acute anaphylaxis). Furthermore, target tissues have previously been isolated from the circulation via occlusion of major arteries and veins, with support via external artificial circulation, which requires invasive procedures, particularly for some tissues that are difficult to access. For instance, transduction of the myocardium has necessitated circulatory isolation by highly invasive surgical means to administer the aforementioned interventions. The combined risks associated with highly invasive procedures incorporating intra-vascular pressure elevation and pharmacological agents with established toxic potential represent significant shortcomings to the realization of an efficacious procedure that is safe for systemic administration and body-wide dispersion of therapeutic genetic components.

Therefore, what is needed are compositions and methods that allow for systemic nucleic acid sequence delivery without the need for systemic administration aids such as increased vascular pressure, isolated blood vessels or organs, or extracorporeal support for a subject.

SUMMARY OF THE INVENTION

The present invention provides compositions, methods and kits for systemic nucleic acid sequence delivery. In particular, the present invention provides systemic nucleic acid sequence delivery without conventional systemic administration aids (SAAs). In certain embodiments, vascular permeability agents (VPAs), such as VEGF, are used in conjunction with nucleic acid viral vectors, such as recombinant adeno-associated virus (AAV). The present invention also provides methods of treating disease by co-administration of nucleic cid sequences encoding Igf-1 and dystrophin or dystrophin-like proteins.

In some embodiments, the present invention provides methods of systemic transduction of extravascular tissue comprising; a) providing; i) a first composition comprising nucleic acid vectors, wherein the nucleic acid vectors comprise a nucleic acid sequence of interest, ii) a second composition comprising a vascular permeabilizing agent (e.g. a VEGF molecule such as a VEGF isoform), and iii) a subject comprising a first type of extravascular tissue; and b) administering the first and second compositions systemically to the subject, without using a systemic administration aid (i.e. systemic administration aid-free administration), under conditions such that the first type of extravascular tissue is transduced by the nucleic acid vectors. In particular embodiments, the first and second compositions are mixed together prior to the administering.

In certain embodiments, the present invention provides methods of systemic transduction of extravascular tissue comprising; a) providing; i) a first composition comprising nucleic acid vectors, wherein the nucleic acid vectors comprise a nucleic acid sequence of interest, ii) a second composition comprising a vascular permeabilizing agent, and iii) a subject comprising a first type of extravascular tissue; and b) administering the first and second compositions systemically to the subject under conditions such that: i) the subject lacks at least one subject systemic administration aid; and ii) the first type of extravascular tissue is transduced by the nucleic acid vectors. In particular embodiments, the first and second compositions are mixed together prior to the administering.

In other embodiments, the subject lacks at least one subject systemic administration aid selected from the group consisting of: a reduction in body temperature of the subject; the subject is unconscious, the subject is on extracorporeal circulatory support, the first type of extravascular tissue is isolated from the remainder of the subject, the first type of extravascular tissue in the subject is exsanguinated, and the subject has hepatic inflow occlusion. In some embodiments, the subject lacks at least two, or three or four or five subject systemic administration aids selected from the group consisting of: a reduction in body temperature of the subject; the subject is unconscious, the subject is on extracorporeal circulatory support, the first type of extravascular tissue is isolated from the remainder of the subject, the first type of extravascular tissue in the subject is exsanguinated, and the subject has hepatic inflow occlusion. In particular embodiments, the subject lacks all six of the following subject systemic administration aids: a reduction in body temperature of the subject; the subject is unconscious, the subject is on extracorporeal circulatory support, the first type of extravascular tissue is isolated from the remainder of the subject, the first type of extravascular tissue in the subject is exsanguinated, and the subject has hepatic inflow occlusion.

In certain embodiments, the subject is conscious. In other embodiments, the body temperature of the subject is normal (not reduced). In further embodiments, the subject is free from extracorporeal circulatory support. In other embodiments, the subject is not in cardiac arrest and/or is not under anesthesia. In some embodiments, the first type of extravascular tissue is not isolated from the remainder of the subject. In additional embodiments, the first type of extravascular tissue is non-exsanguinated. In certain embodiments, the subject does not have heppatic inflow occlusion. In further embodiments, the administering is performed without at least one blood vessel systemic administration aid.

In some embodiments, the present invention provides methods of systemic transduction of extravascular tissue comprising; a) providing; i) a first composition comprising nucleic acid vectors, wherein the nucleic acid vectors comprise a nucleic acid sequence of interest, ii) a second composition comprising a vascular permeabilizing agent, and iii) a subject comprising a first type of extravascular tissue; and b) administering the first and second compositions systemically to one or more blood vessels in the subject, without using at least one blood vessel systemic administration aid, under conditions such that the first type of extravascular tissue is transduced by the nucleic acid vectors. In particular embodiments, the first and second compositions are mixed together prior to the administering.

In certain embodiments, the at least one blood vessel systemic administration aid is selected from the group consisting of: increased perfusion pressure in the one or more blood vessels (i.e. increased perfusion pressure not caused by the injection itself and not caused as a result of a biological reaction caused by the VPA); where one or more blood vessels are isolated from the remainder of the subject; wherein the site or sites of administration is not distant from the first type of extravascular tissue; wherein the administration is directly in the coronary circulation of the subject; wherein the administration is followed by administering an oxygen-transporting agent to the on or more blood vessels; and prior to the administration, delivering a vasodilating agent to the one or more blood vessels.

In additional embodiments, the administering is conducted without at least two, or three, or four, or five blood vessel systemic administration aids selected from the group consisting of: increased perfusion pressure in the one or more blood vessels (i.e. increased perfusion pressure not caused by the injection itself and not caused as a result of a biological reaction caused by the VPA); wherein the one or more blood vessels are isolated from the remainder of the subject; wherein the site or sites of administration is not distant from the first type of extravascular tissue; wherein the administration is directly in the coronary circulation of the subject; wherein the administration is followed by administering an oxygen-transporting agent to the on or more blood vessels; and prior to the administration, delivering a vasodilating agent to the one or more blood vessels.

In particular embodiments, the administering is conducted without any of the following six blood vessel systemic administration aids: increased perfusion pressure in the one or more blood vessels (i.e. increased perfusion pressure not caused by the injection itself and not caused as a result of a biological reaction caused by the VPA), wherein the one or more blood vessels are isolated from the remainder of the subject, wherein the site or sites of administration is not distant from the first type of extravascular tissue, wherein the administration is directly in the coronary circulation of the subject, wherein the administration is followed by administering an oxygen-transporting agent to the on or more blood vessels, and prior to the administration, delivering a vasodilating agent to the one or more blood vessels.

In some embodiments, the administering is in a blood vessel or blood vessels of the subject that is (are) distant from the first type of extravascular tissue (e.g. in a blood vessel not directly associated with the first type of extravascular tissue, or at least 5 inches, or 10 inches or 20 inches or 2 feet from the first type of extravascular tissue). In certain embodiments, the administering is to one or more blood vessels under physiologically normal (non-enhanced) pressure, and/or the pressure is not increased after the administering. In additional embodiments, the one or more blood vessels are not isolated from the remainder of the subject. In some embodiments, the administration is not directly in the coronary circulation of the subject. In certain embodiments, the administering is not followed by administering an oxygen-transporting agent to the one or more blood vessels (e.g. no oxygen-transport agent is administered to the one or more blood vessels within 24-48 hours of the administration of the first and second compositions. In other embodiments, no vasodilating agent is delivered to the one or more blood vessels prior, or during, to the administering the first and second compositions (e.g. no vasodilating agent is present in the first or second composition and no vasodilating agent is delivered before the first and second compositions are administered).

In certain embodiments, at least 30%, 40%, 50%, 60%, 70%, 80%, 85%, 90%, 95% or substantially all cells in the first type of extravascular tissue express the nucleic acid sequence of interest. In other embodiments, the level of transduction is achieved with a single administration of the first and second compositions (e.g. no additional treatments are given over the next 90 days).

In preferred embodiments, the first and second compositions are administered simultaneously (e.g. as part of single combined-composition or within 20 seconds of each other). In other embodiments, the first composition is administered within 5 minutes of the second composition. In some embodiments, the first composition is administered within 3 minutes, 2 minutes, 30 second, 10 seconds, 5 seconds, or at the same time as the second composition.

In some embodiments, the first composition and the second composition are administered to the same blood vessel. In other embodiments, the first composition and the second composition are administered to different blood vessels. In additional embodiments, the first and/or second composition further comprises heparin. In other embodiments, the methods further comprise providing a third composition comprising heparin, wherein the administering further comprises systemically administering the third composition to the subject.

In particular embodiments, the first type of extravascular tissue is heart tissue (e.g. the heart or a portion thereof, such as the muscle tissue in the heart). In other embodiments, the first type of extravascular tissue is skeletal muscle tissue (e.g. muscles in the legs, muscles in the arms, muscles in the abdomen, muscles in the back, muscles in the face, or substantially all the skeletal muscles of the subject).

In certain embodiments, a significant proportion of the skeletal muscle tissue in the subject is transduced by the nucleic acid vectors (e.g. 30%, 40% or 60% of the skeletal muscle tissue in the subject expresses the nucleic acid sequence of interest). In preferred embodiments, as a result of the administering, substantially all of the skeletal muscle tissue in the subject is transduced by the nucleic acid vectors (e.g. as evidenced by at least 75 or at least 85%, or 90% of the skeletal muscle tissue expressing the nucleic acid sequence of interest). This may be determined by biopsy or inferred based on activity levels of the muscles before and after administering the first and second compositions. In certain preferred embodiments, the nucleic acid sequence of interest encodes dystrophin or is a mini-dystrophin nucleic acid sequence.

In certain embodiments, the nucleic acid vectors are viral vectors. In other embodiments, the nucleic acid vectors are adeno-associated vectors. In some embodiments, the adeno-associated vectors are AAV1-AAV9, (e.g. AAV6 or AAV1 are preferred). In preferred embodiments, the nucleic acid vectors comprise an AAV6 capsid (e.g., AAV6 vectors or AAV6 psuedo-typed vectors).

In additional embodiments, the vascular permeabilizing agent is a VEGF molecule (e.g. a VEGF isoform, or mimetic, VEGF165, PGF, fragmets thereof, an agent that is able to bind Flt1 or Flk1, or a non-toxic vascular permeabilizing agent). In certain embodimetns, the first and second compositions are together in a combined-composition. In further embodiments, a vascular permeabilizing agent is conjugated to the nucleic acid vectors. In other embodiments, the viral vectors further comprise a ligand specific for the vascular pemerabilizing agent (e.g. Fab, single chain antibody region, protein A, Flt1, Flk1, etc.).

In some embodiments, the first composition is a vasodilating agent-free composition (i.e. does not contain a vasodilating agent). In other embodiments, the second composition is a vasodilating agent-free composition (i.e. does not contain a vasodilating agent). In further embodiments, the administering is conducted without ever administering a vasodilating agent. In particular embodiments, the administering is conducted without ever administering histamine.

In additional embodiments, the subject has symptoms of a disease, and wherein the administering reduces at least one of the symptoms of disease. In some embodiments, this reduction in symptoms is the result of a single administration of the first and second compositions (e.g. no additional administration occurs over the 90 days following the initial administration). In certain embodiments, the disease is selected from heart disease, a muscular dystrophy, a nueuropathy such as Alzheimer's disease, hemophelia, cancer (e.g. breast cancer, lung cancer, skin cancer, prostate cancer, etc.), Pompe's disease, Fabry's disease, bacterial or viral infection, or diseases associated with aging.

In some embodiments, the subject has symptoms of disease in the first type of extravascular tissue, and wherein the administering reduces at least one of the symptoms of disease in the first type of extravascular tissue. In other embodiments, the subject has symptoms of disease in the first type of extravascular tissue such that the first type of extravascular tissue has a function deficit compared to wild type (e.g. a reduced ability to function for its intended function compared to a wild type), and wherein the administering at least partially compensates for the function deficit (e.g. reduces symptoms of disease is the extravascular tissue, and/or improves the extravascular tissue such that it is nearly equal in function compared to the wild type; e.g. 80% of the activity of wild type or 90%, or 95% of the activity of wild type). In preferred embodiments, the disease treated is a muscular dystrophy such as DMD.

In further embodiments, the first type of extravascular tissue is an organ selected from: heart, kidney, eyes, pancrease, liver, gall bladder, intestines, stomach, lungs, urinary track, and diaphragm. In other embodiments, the first type of extravascular tissue is skeletal muscle tissue, heart muscle tissue, diaphragm tissue, leg muscle tissue, arm muscle tissue, etc. In some embodiments, the subject comprises a second extravascular tissue type, and the administering is under conditions such that the first and second extravascular tissues are transduced by the nucleic acid vectors. In preferred embodiments, the administering is performed with a needle and syringe. In particular embodiments, the administering is in one or more blood vessels of the subject. In some embodiments, the nucleic acid sequence of interest is selected from dystrophin, mini-dystrophin, or other therapeutic sequences. In further embodiments, the administering is conducted with a muscle transduction aid (e.g., heat, moderate exercise, ultrasound, etc.).

In certain embodiments, the first composition comprises less than $1 \times 10^{12}$ nucleic acid vectors per milliliter (e.g., $8 \times 10^{11}$ nucleic acid vectors per milliliter or less; $1-5 \times 10^{11}$ nucleic acid vectors per milliliter or less; $1 \times 10^{9}-8 \times 10^{11}$ nucleic acid vectors per milliliter, or $1 \times 10^{10}-3 \times 10^{11}$ nucleic acid vectors per milliliter). In some embodiments, the first composition is administered to the subject at a dosage of less than $1 \times 10^{12}$ vectors per kilogram of the subject (e.g., $8 \times 10^{11}$ vectors per kilogram of the subject or less; $1-5 \times 10^{11}$ vectors per kilogram of the subject or less; $1 \times 10^{9}-8 \times 10^{11}$ vectors per kilogram of the subject, or $1 \times 10^{10}-3 \times 10^{11}$ vectors per kilogram of the subject).

In some embodiments, the compositions of the present invention comprises about $1 \times 10^{12}$ nucleic acid vectors per milliliter, about $1 \times 10^{13}$ nucleic acid vectors per milliliter, about $1 \times 10^{14}$ nucleic acid vectors per milliliter, about $1 \times 10^{15}$ nucleic acid vectors per milliliter, about $1 \times 10^{16}$ nucleic acid vectors per milliliter, or about $1 \times 10^{17}$ nucleic acid vectors per milliliter. In particular embodiments, the compositions contain no more than $1 \times 10^{16}$ nucleic acid vectors per milliliter, or $1 \times 10^{17}$ nucleic acid vectors per milliliter. In certain embodiments, the compositions of the present invention are administered to a subject at a dosage of about $1 \times 10^{11}$ nucleic acid vectors per kilogram of subject, about $1 \times 10^{12}$ nucleic acid vectors per kilogram of subject, about $1 \times 10^{13}$ nucleic acid vectors per kilogram of subject, about $1 \times 10^{14}$ nucleic acid vectors per kilogram of subject, about $1 \times 10^{15}$ nucleic acid vectors per kilogram of subject, about $1 \times 10^{16}$ nucleic acid vectors per kilogram of subject, or about $1 \times 10^{17}$ nucleic acid vectors per kilogram of subject (e.g. about $4 \times 10^{14}$ nucleic acid vectors per kilogram of subject, or about $8 \times 10^{14}$ nucleic acid vectors per kilogram of subject). In additional embodiments, the compositions contain no more than $1 \times 10^{16}$ nucleic acid vectors per kilogram of subject, or no more than $1 \times 10^{17}$ nucleic acid vectors per kilogram of subject.

In further embodiments, the administering is in a blood vessel in a limb (e.g. arm or leg). In certain embodiments, the administering is in a blood vessel of the subject that is distant from the first type of extravascular tissue (e.g. in a blood vessel not directly associated with the first type of extravascular tissue, or at least 5 inches, or 10 inches or 20 inches or 2 feet from the first type of extravascular tissue). In some embodiments, the nucleic acid vectors are less than 70 μm in diameter (e.g., vectors with a diameter around 10 nm to 50 nm or 5 nm to 70 nm).

In additional embodiments, the present invention provides methods of systemic transduction of extravascular tissue comprising; a) providing; i) a composition comprising nucleic acid vectors, wherein the nucleic acid vectors comprise an AAV6 capsid and a nucleic acid sequence of interest, and ii) a subject comprising a first type of extravascular tissue; and b) administering the composition systemically to the subject, without using a systemic administration aid, under conditions such that the first type of extravascular tissue is transduced by the nucleic acid vectors.

In other embodiments, the present invention provides methods of systemic transduction of extravascular tissue comprising; a) providing; i) a composition comprising nucleic acid vectors, wherein the nucleic acid vectors comprise an AAV6 capsid and a nucleic acid sequence of interest, and ii) a subject comprising a first type of extravascular tissue; and b) administering the composition systemically to the subject under conditions such that: i) the subject lacks at least one subject systemic transduction aid; and ii) the first type of extravascular tissue is transduced by the nucleic acid vectors.

In some embodiments, the present invention provides methods of systemic transduction of extravascular tissue comprising; a) providing; i) a composition comprising nucleic acid vectors, wherein the nucleic acid vectors comprise an AAV6 capsid and a nucleic acid sequence of interest, and ii) a subject comprising a first type of extravascular tissue; and b) administering the composition systemically to one or more blood vessels in the subject, without using at least one blood vessel systemic administration aid, under conditions such that the first type of extravascular tissue is transduced by the nucleic acid vectors.

In other embodiments, the composition comprises at least $1 \times 10^{12}$ nucleic acid vectors per milliliter (e.g., $8 \times 10^{12}$ nucleic acid vectors per milliliter or more, $1-5 \times 10^{12}$ nucleic acid vectors per milliliter or more; $1 \times 10^{13}-8 \times 10^{13}$ nucleic acid vectors per milliliter; $1 \times 10^{13}-3 \times 10^{13}$ nucleic acid vectors per milliliter). In particular embodiments, the composition is administered to the subject at a dosage of greater than $1 \times 10^{12}$ vectors per kilogram of the subject (e.g., $8 \times 10^{13}$ vectors per kilogram of the subject or more, $1-5 \times 10^{13}$ vectors per kilogram of the subject or more; $1 \times 10^{13}-8 \times 10^{13}$ vectors per kilogram of the subject, or $1 \times 10^{13}-3 \times 10^{13}$ vectors per kilogram of the subject).

In some embodiments, the present invention provides methods of systemic transduction of extravascular tissue comprising; a) providing; i) a first composition comprising nucleic acid vectors, wherein the nucleic acid vectors comprise a nucleic acid sequence of interest, and wherein the first composition comprises less than $1 \times 10^{12}$ nucleic acid vectors per milliliter, ii) a second composition comprising a vascular permeabilizing agent, and iii) a subject comprising a first type of extravascular tissue; and b) administering the first and second compositions systemically to the subject under conditions such that the first type of extravascular tissue is transduced by the nucleic acid vectors.

In other embodiments, the present invention provides methods of systemic transduction of extravascular tissue comprising; a) providing; i) a composition comprising nucleic acid vectors, wherein the nucleic acid vectors comprise an AAV6 capsid and a nucleic acid sequence of interest, and wherein the composition comprises at least $1 \times 10^{12}$ nucleic acid vectors per milliliter, and ii) a subject comprising a first type of extravascular tissue; and b) administering the composition systemically to the subject under conditions such that the first type of extravascular tissue is transduced by the nucleic acid vectors.

In further embodiments, the present invention provides compositions comprising: a) a vascular permeabilizing agent, and b) nucleic acid vectors comprising a nucleic acid sequence of interest, wherein the nucleic acid vectors are present in a concentration between $1 \times 10^9$ nucleic acid vectors and $1 \times 10^{12}$ nucleic acid vectors per milliliter. In some embodiments, the nucleic acid vectors are present in a concentration between $1 \times 10^{10}$ nucleic acid vectors and $5 \times 10^{11}$ nucleic acid vectors per milliliter. In other embodiments, the nucleic acid vectors are present in a concentration of about $1 \times 10^{11}$ nucleic acid vectors per milliliter. In additional embodiments, the compositions do not contain a vasodilating agent. In other embodiments, the composition does not contain histamine. In some embodiments, the compositions further comprise heparin. In preferred embodiments, the vascular permeabilizing agent is non-toxic. In particular embodiments, the vascular permeabilizing agent is conjugated to the nucleic acid vector. In preferred embodiments, the nucleic acid sequence of interest is dystrophin, mini-dystrophin sequence, or a truncated or modified dystrophin sequence.

In some embodiments, the nucleic acid vectors are viral vectors. In further embodiments, the nucleic acid vectors are adeno-associated vectors (e.g., AAV1-AAV9, AAV6 or AAV1). In certain embodiments, the nucleic acid vectors comprise an AAV6 capsid (e.g., AAV6 vectors or AAV6 psuedo-typed vectors). In some embodiments, the vascular permeabilizing agent is a VEGF molecule.

In other embodiments, the present invention provides compositions comprising nucleic acid vectors, wherein the nucleic acid vectors comprise a nucleic acid sequence of interest, are wherein the nucleic acid vectors are present in a concentration between $1 \times 10^{12}$ nucleic acid vectors and $1 \times 10^{15}$ nucleic acid vectors per milliliter. In certain embodiments, the compositions further comprises heparin. In some embodiments, the composition does not contain a vascular permeabilizing agent.

In particular embodiments, the present invention provides kits comprising; a) a first composition comprising nucleic acid vectors, wherein the nucleic acid vectors comprise a nucleic acid sequence of interest, b) a second composition comprising a vascular permeabilizing agent, and c) a written insert comprising instructions for systemically administering the first and second compositions, wherein the instructions do not indicate that one or more systemic administration aids are to be employed.

In other embodiments, the present invention provides kits comprising: a) a composition comprising: i) nucleic acid vectors, wherein the nucleic acid vectors comprise a nucleic acid sequence of interest, and ii) a vascular permeabilizing agent, and c) a written insert comprising instructions for systemically administering the composition, wherein the instructions do not indicate that one or more systemic administration aids are to be employed.

In some embodiments, the present invention provides kits comprising; a) a first composition comprising nucleic acid vectors, wherein the nucleic acid vectors comprise an AAV6 capsid and a nucleic acid sequence of interest, and b) a written insert comprising instructions for systemically administering the first and second compositions, wherein the instructions do not indicate that one or more systemic administration aids are to be employed.

In certain embodiments, the present invention provides methods of treating a subject comprising; a) providing; i) a first plurality of nucleic acid sequences encoding dystrophin or dystrophin-like proteins, ii) a second plurality of nucleic acid sequences encoding insulin-like growth factor 1 (Igf-1), and iii) a subject comprising muscle tissue; and b) administering the first and second plurality of nucleic acid sequences to the subject under conditions such that the muscle tissue of the subject exhibits an increase in mass, strength, and protection from contraction-induced injury. In some embodiments, the dystrophin-like proteins are selected from the group consisting of: micro-dystrophin proteins, utrophin proteins, micro-utrophin proteins, dystrophin/utrophin chimera proteins, and micro-dystrophin/utrophin chimera proteins. In further embodiments, the administering comprises systemic injection of the first and second plurality of nucleic acid sequences simultaneously, or within 1 hour of each other, or within 12 days of each other (e.g. within 5 minutes to 7 days of each other). In particular embodiments, the first or second plurality of nucleic acid sequences are packaged in adeno-associated virus capsids. In preferred embodiments, the subject is an elderly human (e.g. a human patient 65 years or older who's exhibits symptoms of muscle tissue wasting).

In some embodiments, the present invention provides methods of treating a subject comprising; a) providing; i) a composition comprising nucleic acid vectors, wherein the nucleic acid vectors comprise a nucleic acid sequence encoding insulin-like growth factor 1 (Igf-1), and ii) a subject with symptoms of a muscle wasting disease; b) administering the composition to the subject under conditions such that at least one symptom of muscle wasting is reduced or eliminated. In preferred embodiments, the subject is an elderly human (e.g. a human patient 65 years or older who's exhibits symptoms of muscle tissue wasting).

In certain embodiments, the present invention provides compositions comprising micro-utrophin proteins or micro-utrophin/dystrphin chimeric proteins, or nucleic acid sequences encoding these proteins. For example, in some embodiments, the present invention provides nucleic acid sequences encoding micro-utrophin proteins with 4.0 utrophin spectrin-like repeats (see, e.g. FIG. 12). In other embodiments, the present invention provides nucleic acid sequences encoding micro-utrophin/dystrophin chimeric proteins with 4.0 spectrin-like repeats from utrophin and dystrophin (e.g. 3 utrophin and 1 dystrophin spectrin-like repeats, or 2 utrophin and 2 dystrophin spectrin-like repeats, or 1 utrophin and 3 dystrophin spectrin-like repeats; see e.g. FIG. 12). In other embodiments, the micro proteins comprise other elements (e.g. from utrophin or dystrophin) such as an actin binding amino-terminal domain, 2, 3 or 4 hinge domains, and WW and cysteine rich domains. In certain embodiments, the micro-utrohin sequences are similar to or identical to SEQ ID NOs. 1, 2 and 6. In some embodiments, the micro-utrophin nucleic sequence (or peptides) are used to treat a subject (e.g. a subject with a muscle wasting disease). In further embodiments, a vascular permeablizing agent (e.g. VEGF-A or AAV6 empty capsids) are combined with the micro-utrophins nucleic acid sequences.

DESCRIPTION OF THE FIGURES

FIG. 2 shows β-galactosidase activity (driven by the CMV promoter) in various muscles and organs following systemic delivery of $2 \times 10^{11}$ or $10^{12}$ doses of viral vector with and without VEGF

FIG. 13A shows the nucleic acid sequence (SEQ ID NO:1) of the murine micro-utrophin sequence employed in Example 6. FIG. 13B shows the nucleic acid sequence (SEQ ID NO:2) of an additional murine micor-utrophin sequence that could be employed to treat muscle wasting type conditions. FIG. 13C shows the nucleic acid sequence (SEQ ID NO:6) of a human micro-utrophin sequence that could be employed (e.g. for treating a human subject). Of course changes could be introduced into these sequences to produce additional micro-utrophins sequences (see e.g. FIG. 12).

FIG. 14A shows the micro-dystrophin and Igf-1 constructs used in Example 7. FIG. 14B shows a graph reporting dystrophin positive area type results of Example 7.

FIG. 16 shows a graph of results of tissue measurements from mice treated as described in Example 7, including: A) percentage of central nuclei; B) number of fibers/area; and C) fiber diameter.

FIG. 17A shows a graph that indicates that intravenous administration of rAAV6-Igf-1 vectors to old mice in Example 8 results in increased body mass consistent with increased muscle mass. FIG. 17B show the change in Tibialis anterior (hindlimb) muscle mass for the control mice and mice receiving Igf-1 as described in Example 8, revealing that Igf-1 treatment in old mice results in increased muscle strength and performance.

FIG. 18A is a graph that shows the tibialis anterior (TA) muscles of old mice treated with Igf-1 expressing vectors in Example 8 generates increased force compared with the muscles of untreated mice. FIG. 18B is a graph that shows that the muscles of Igf-1 treated mice in Example 8 display increased force output over a protocol of repetitive stimulation and at recovery.

FIG. 19 show the nucleic acid sequences for murine Igf-1 Eb (SEQ ID NO:3), murine Igf-I Ea (SEQ ID NO:4), and human Igf-1 (SEQ ID NO:5).

DEFINITIONS

Figure 1:
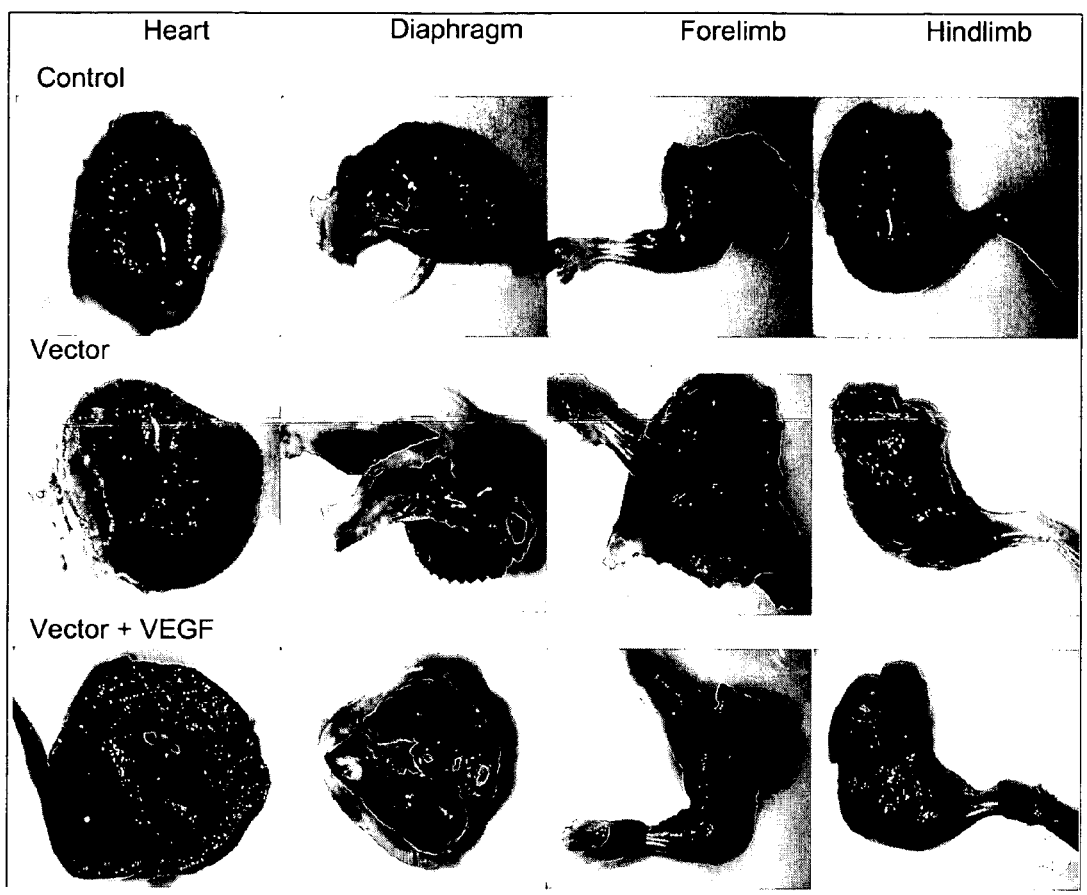
FIG. 1 shows a plate demonstrating the gray/black muscles of mice receiving vector and VEGF/heparin, as well as mice receiving vector alone. The dark shading is a reaction generated from the enzyme produced by the gene (LacZ) delivered by the virus.

To facilitate an understanding of the invention, a number of terms are defined below.

As used herein, the terms "subject" and "patient" refer to any animal, such as a mammal like a dog, cat, bird, livestock, and preferably a human.

As used herein, the term "subject systemic administration aid" or "SSAA" refers to non-trivial changes that are made to a subject prior to or during systemic administration of a nucleic acid vector in order to increase the transduction efficiency of the administered nucleic acid vector. In preferred embodiments, SSAAs include: a reduction in body temperature of the subject; a subject that is unconscious (e.g., subject to anesthesia), placing a subject on extracorporeal circulatory support (e.g., using a heart and lung machine), isolating the target extravascular tissue from the remainder of the subject, exsanguinating (removing the majority of blood from) the target extravascular tissue/organ, providing the subject with hepatic inflow occlusion.

As used herein, the term "blood vessel systemic administration aid" or "BVSAA" refers to: non-trivial changes that are made to a blood vessel prior to or during systemic administration of a nucleic acid vector; choice of blood vessel site of administration of the nucleic acid vector; or reagents applied to a blood vessel prior to, during, or immediately after administration; all used in order to increase transduction efficiency of the administered nucleic acid vector. In preferred embodiments, BVSAAs include: increased perfusion pressure in a blood vessel (i.e. increased perfusion pressure not caused by the injection itself and not caused as a result of a biological reaction caused by the VPA); isolating the blood vessel from the remainder of the subject; employing a site of administration that is close to and/or generally associated with the target extravascular tissue (i.e. not a site distant from the target extravascular tissue), administration directly in the coronary circulation of the subject (i.e. choosing a coronary blood vessel for site of administration); administering an oxygen-transporting agent to one or more blood vessels following administration of the nucleic acid vector; and prior to the administration of the nucleic acid vectors, delivering a vasodilating agent to a blood vessel.

As used herein, the term "systemic administration aid" or "SAA" includes both subject systemic administration aids (SSAAs) and the blood vessel systemic administration aids (BVSAAs).

The term "fragment" as used herein refers to a polypeptide that has an amino-terminal deletion, and/or carboxy-terminal deletion, and/or both amino terminal and carboxy terminal deletion (e.g. leaving only a center portion) as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions with its various ligands and/or substrates.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the terms "vector" or "nucleic acid vector" are used in reference to nucleic acid molecules (e.g., plasmids) or viruses (e.g. adeno-associated viruses) that transfer DNA segment(s) from one cell to another. The term "vehicle" is sometimes used interchangeably with "vector." Examples include, but are not limited to plasmids, adeno-associated viruses, and adenoassociated viruses. When a nucleic acid vector contains a nucleic acid sequence of interest, generally the nucleic acid vector includes, for prokaryotic expression, nucleic acid sequences such as a promoter, an operator (optional), and a ribosome binding site, often along with other sequences. If the nucleic acid vector is to be used in eukaryotic cells, nucleic acid sequence such as promoters, enhancers, and termination and polyadenylation signals are generally included with the nucleic acid sequence of interest.

As used herein, the term "transduction" refers to the introduction of foreign nucleic acid, such as a nucleic acid sequence of interest, into cell via a nucleic acid vector.

As used herein, "extravascular tissue" refers to a tissue which is located outside of a blood vessel. It is noted that extravascular tissue may surround a given blood vessel. Examples of extravascular tissue include, but are not limited to, skeletal muscle, heart muscle, diaphragm tissue, etc.

As used herein, "vascular permeability agent" is a composition of matter which, when supplied to a blood vessel of an animal, preferably a mammal, increases the permeability of the endothelial layer of the vessel, such that substances within the vessel may pass through the endothelial layer.

As used herein, a "vasodilating agent" is a composition of matter which, when supplied to a blood vessel of an animal, preferably a mammal, increases the luminal diameter of the vessel. Stated another way, a vasodilating agent, when administered to a blood vessel of an animal, increases the caliber of the vessel.

As used herein, the "perfusion pressure" within a blood vessel means the peak pressure differential between the fluid within the lumen of the vessel and the fluid surrounding the vessel. It is understood that the peak pressure within the vessel corresponds to the driving force for blood flow through the vessel by the beating action of the animal heart. The "normal physiological" perfusion pressure within a blood vessel means the perfusion pressure within the vessel of a healthy animal in a resting state.

As used herein, an "oxygen-transporting agent" means a composition of matter which, when in a liquid or solution form, is capable of capturing an oxygen molecule and delivering the oxygen molecule to a biological oxygen carrier such as hemoglobin or myoglobin. By way of example, numerous synthetic blood substitutes and perfluorochemical liquids are oxygen-transporting agents.

As used herein, the phrase "extracorporeal circulatory support" means a subject is attached to a mechanical device which is capable of circulating the blood of the subject through all or a part of the circulatory system of the subject without assistance from the heart of the subject. By way of example, a heart-lung machine, which is well known in the art, is a device which is useful for providing extracorporeal circulatory support.

DESCRIPTION OF THE INVENTION

The present invention provides compositions, methods and kits for systemic nucleic acid sequence delivery. In particular, the present invention provides systemic nucleic acid sequence delivery without conventional systemic administration aids (SAAs). In certain embodiments, a vascular permeability agents (VPAs), such as VEGF, are used in conjunction with nucleic acid viral vectors, such as adeno-associated virus (AAV). The present invention also provides methods of treating disease by co-administration of nucleic cid sequences encoding Igf-1 and dystrophin or dystrophin-like proteins. For convenience, the invention is described in further detail below in the following sections: (I) Systemic Nucleic Acid Sequence Delivery; (II) Vascular Permeabilizing Agents; (III) Nucleic Acid Vectors; (IV) Nucleic Acid Vector Conjugates; (V) Nucleic Acid Sequence of Interest; and (VI) Administration of Therapeutic Compositions.

I. Systemic Nucleic Acid Sequence Delivery

The present invention provides methods and compositions for systemic nucleic acid sequence delivery to extravascular tissue such as skeletal muscle or heart muscle without using systemic administration aids (SAAs) such as subject systemic administration aids (SSAAs) and blood vessel systemic administration aids (BVSAAs). This is important as, prior to the present invention, delivery of vectors via the vasculature has resulted in useful levels of transduction only in organs such as the liver, which contain highly permeable fenestrated vasculature designed to filter the blood of foreign particles. Intra-vascular delivery of vectors has met with extremely limited success in most other tissues, including muscle. One exception, mentioned above, is an extremely invasive technique (using systemic administration aids) that involves placing an animal under general anesthesia and isolating the target limb from the blood system by occluding the major veins and arteries. The limb is exsanguinated and the blood volume is replaced with a solution containing potent vasodilators and permeabilizing agents (principally histamine and papaverine). Following pretreatment, the pharmacological agents are washed out and a vector containing solution is pumped into the limb under hydrostatic pressure. At the culmination of vector administration, residual solution is evacuated and the limb is returned to the blood supply. This technique has also been applied to the heart, where it is necessary to place the animal on life support during the process in order to access the heart via the chest cavity, and in some modifications of the procedure, the heart is excised and surgically reattached after treatment with vector (See, e.g., Bridges et al., Ann Thorac Surg. June 2002; 73(6):1939-46). These techniques increase the efficiency of gene transfer to one limb or the heart, but are not truly systemic. Additionally, they are extremely invasive and some patients may not survive the insult. Together, these limitations limit the clinical relevance of the techniques reported in previous studies (see also, U.S. Pat. No. 6,177,403 to Stedman).

Also, it is the accepted practice to use the pharmacologic intervention as a pre-treatment that is removed before administration of the vector. This contrasts to some embodiments of the present invention (see, e.g., Examples sections below) where co-administration of the vector with the bioactive agent at the same time leads to markedly increased transduction efficiencies.

In certain prior art methods, such as those shown in U.S. Pat. No. 6,177,403 to Stedman, it is believed necessary to perform many systemic administration aids in order to achieve significant systemic transduction levels. For example, Stedman teaches the necessity to isolate a blood vessel, treat with a vasodilating agent, and treat with a vascular pemeability agent prior to systemically administering any type of vector (as well as providing an oxygen-transporting agent to the vessel after administration). Stedman also shows, in Table 1, that muscle can only be transduced using, inter alia, moderate or high pressure in the blood vessel (as well as requiring both histamine and papaverine). The Stedman patent also indicates the need to place a subject on extracorporeal circulatory support and oxygenation prior to providing any vector (as well as requiring an increase in perfussion pressure in the blood vessel). The present invention does not require these elaborate and often dangerous procedures.

Existing methods prescribe that the pharmacologic agents and vector are administered into an isolated heart or limb of an anesthetized animal by accessing the major artery feeding the heart or limb. In contrast, the present invention employs a much simpler venous access directly into a conscious animal without isolating portions of its body from the circulation. The prevailing opinion in the field is that vector should be fed directly into an artery feeding the area of interest to preserve the vector from being taken up by non-target organs such as the liver, or neutralized in vivo prior to accessing the target tissue. However, the present invention allows for distant administration (systemic administration not near the target tissue). As shown in the Example below, high efficiency transduction with venous administration has been observed with limited transduction of non-target (including liver) relative to target tissues.

The present invention (e.g. as shown in the Example below) also does not employ the high injection volumes and increases in vascular pressure that are used in many reported protocols and are considered to be a critical to their efficiencies. Indeed, in preferred embodiments, the present invention does not necessitate increases in blood pressure nor the replacement of the blood with a reagent-containing buffer. For example, in the Example below, injections directly into the blood represented only about 10% total blood volume; a clinically tolerated volume in humans.

As noted above, the present invention allows for systemic nucleic acid administration, (with extravascular transduction), without the need for systemic administration aids, such as subject systemic administration aids or blood vessel administration aids.

Subject systemic administration aids or "SSAAs" are non-trivial changes that are made to a subject prior to or during systemic administration of a nucleic acid vector in order to increase the transduction efficiency of the administered nucleic acid vector. The present invention allows systemic administration and transduction without the need for such aids. Examples of SSAAs include: a reduction in body temperature of the subject; a subject that is unconscious (e.g., subject to anesthesia), placing a subject on extracorporeal circulatory support (e.g., using a heart and lung machine), isolating the target extravascular tissue from the remainder of the subject, exsanguinating (removing the majority of blood from) the target extravascular tissue/organ, and providing the subject with hepatic inflow occlusion. Rather than employing such SSAAs, the present invention allows systemic nucleic acid administration where: the body temperature of the subject is normal (not reduced); the subject is free from extracorporeal circulatory support and/or oxygenation; the subject is not in cardiac arrest and/or is not under anesthesia; the extravascular tissue is not isolated from the remainder of the subject; the extravascular tissue is non-exsanguinated; the subject does not have heppatic flow occlusion.

Blood vessel systemic administration aids or BVSAAs are non-trivial changes that are made to a blood vessel prior to or during systemic administration of a nucleic acid vector; choice of blood vessel site of administration of the nucleic acid vector; or reagents applied to a blood vessel prior to, during, or immediately after administration; all used in order to increase transduction efficiency of the administered nucleic acid vector. The present invention allows systemic administration of nucleic acid vectors without BVSAAs. Examples of the BVSAAs include: increased perfusion pressure in a blood vessel; isolating the blood vessel from the remainder of the subject; employing a site of administration that is close to and/or generally associated with the target extravascular tissue (i.e. not a site distant from the target extravascular tissue), administration directly in the coronary circulation of the subject (i.e. choosing a coronary blood vessel for site of administration), administering an oxygen-transporting agent to the on or more blood vessels following administration of the nucleic acid vector, and prior to the administration, delivering a vasodilating agent to a blood vessel. Rather that employing such BVSAAs, the present invention allows systemic nucleic acid administration where: the administering is in a blood vessel or blood vessels of the subject that is (are) distant from the target extravascular tissue (e.g. in a blood vessel not directly associated with the first type of extravascular tissue, or at least 5 inches, or 10 inches or 20 inches or 2 feet from the first type of extravascular tissue); the administering is to one or more blood vessels under physiologically normal (non-enhanced) pressure, and/ or the pressure is not increased after the administering; the one or more blood vessels are not isolated from the remainder of the subject; the administration is not directly in the coronary circulation of the subject; the administering is not followed by administering an oxygen-transporting agent to the on or more blood vessels (e.g. no oxygen-transport agent is administered to the one or more blood vessels within 24-48 hours of the administration nucleic acid vectors and vascular permeabilizing agent); no vasodilating agent is delivered to the blood vessels prior, or during, to the administering of the nucleic acid vectors.

II. Vascular Permeabilizing Agents (VPAs)

As noted above, in certain embodiments, the present invention employs vascular pemerabilizing agents (VPAs) in conjunction with a nucleic acid vector during systemic administration to subject. While the present invention is not limited to any particular VPA, agents that are able to bind Flt1 and Flk1 are preferred (e.g. VEGF molecules, such as VEGF165 or fragments or variants thereof).

A. VPAs in General

The present invention is not limited by the type of VPA that is employed. Examples of VPAs include, but are not limited to, histamine, acetylcholine, adenosine nucleotides, arachidonic acid, bradykinin, cyanide, endothelin, various endotoxins, interleukin-2, ionophore A23187, nitroprusside, various leukotrienes, oxygen radicals, phospholipases, platelet activating factor, protamine, mannitol, sorbitol, serotonin, tumor necrosis factor, vascular endothelial growth factor (VEGF), empty adeno-associated virus capsids (e.g. AAV6 capsids that do not contain viral nucleic acid), venoms, vasoactive amines, fragments or variants of any of the above, as well as combinations of VPAs. In preferred embodiments, the VPA of the present invention is non-toxic such that it can be administered to a subject without harming the subject. A VPA is considered "non-toxic" if it does not have harmful affects on a subject when administered at a dose (with nucleic acid vectors) such that the nucleic acid vectors are able to transduce extravascular tissue at a therapeutic level when administered systemically. One example of a non-toxic VPA is VEGF (e.g. various isoforms, fragments and variants of VEGF).

Importantly, one may determine if a candidate compound (e.g. fragment or variant of the above, or some additional compound) is suitable to serve as a VPA in the present invention by screening the candidate compound. For example, the candidate compound may be substituted for VEGF in Example 1 below. After running the assays described in Example 1 with the candidate compound, the results can be examined to determine if the VPA allows transduction by a viral vector at significant levels (and to determine if the candidate compound is toxic to the animals). In this regard, fragments or variants of the compounds listed above, or other compounds may be screened for usefulness in the methods and compositions of the present invention.

B. VEGF Molecules and the VEGF Receptor Molecules

As noted above, VEGF molecules are preferred in the methods and compositions of the present invention. A "VEGF molecule" includes any VEGF isoform from any species or any fragment or variant of a VEGF isoform that has the same ability to facilitate extravascular transduction by systemic administration of nucleic acid vectors. Fragments and variants of VEGF isoforms may be constructed using known methods in the art such as directed evolution and site directed mutagenesis, and preferably employ Flt1 and Flk1 as binding partners to isolate good VEGF molecule candidates. Such molecules may be screened for usefulness in Example 1 (e.g. by replacing VEGF in the Example) to determine if the candidate VEGF molecule can in fact serve as a VEGF molecule (e.g. facilitate extravascular transduction via systemic administration of nucleic acid vectors). In certain embodiments, the VEGF molecules (e.g. VEGF-A-165) are administered with NP-1 (neurophilin-1).

Vascular endothelial growth factor (VEGF) family members have attracted a great deal of study primarily because of their ability to induce new blood vessel formation, a property related to their ability to act as mitogens on vascular endothelial cells (e.g. Autiero et al., Nat. Med. 2003, 9:936-42). However, some VEGF family members are also known to be potent vascular permeabilizing agents (Senger et al., Science, 1983, 219:983-5, herein incorporated by reference). There are currently 5 known family members of mammalian VEGF, including VEGF-A, VEGF-B, VEGF-C, VEGF-D and placental growth factor (PGF, also known as PLGF). VEGF-A is the most well studied member of the family, and exhibits both mitogenic and vascular permeabilization activities. VEGF-A is expressed as four isoforms, VEGF121 (see Example 3 below), VEGF 165 (known as VEGF164 in mice), VEGF189 and VEGF206, which arise by differential splicing (Houck et al., Mol. Endocrinol., 1991, 5:1806-14). Both VEGF121 and VEGF165 have been reported to display vascular permeabilization activity.

Naturally occurring family members of VEGF are soluble, glycosylated proteins that homodimerize either non-covalently, or via disulfide bonds. Three known receptors have been described, VEGFR-1 (Flt1), VEGFR-2 (Flk-1 or KDR) and VEGFR-3 (Flt-4). VEGF-A binds to both Flt1 and Flk1, while PDF binds only to Flt1. Flt-4 binds only VEGF-C and VEGF-D, which can also bind to Flk-1. VEGF-B binds to Flt1 (reviewed in Wise et al, J. Biol. Chem., 278:38004-14, 2003, herein incorporated by reference). The interaction between VEGF and Flk-1 has been suggested to be responsible for the induction of vascular permeability (Dvorak et al., J. Histochem. Cytochem., 2001; 49:419-32). An additional clue as to the molecular determinants in VEGF that are important for vascular permeabilization has come from studies of different VEGF isoforms, including virally-encoded VEGF isoforms, and the study of VEGF homologues such as placenta growth factor. In one study, Wise et al (2003) studied VEGF genes from 5 different parapoxviruses and showed that they display a large degree of sequence variation, and a variable ability to induce vascular permeabilization. Those authors detected a significant correlation between the ability of viral VEGF proteins to induce vascular permeability and their ability to bind Flk-1. Also, those proteins that induced vascular permeability, including VEGF164, also displayed an interaction with Neuropilin-1 (NP-1) (Wise et al., 2003). In contrast, VEGF-D, which binds Flk-1, fails to bind NP-1 or induce vascular permeability. Also, VEGF121 has been reported to display vascular permeabilization activity, but lacks the VEGF exon 7 sequences thought to mediate interaction with NP-1.

Thus, VEGF peptides that can induce vascular permeability generally have several common features. These features have been suggested to be an ability to interact with Flk-1 and, possibly via heparin, with NP-1. Binding of VEGF-A to Flk-2/KDR is mediated by residues 8-109 of the protein (Muller et al., PNAS USA, 1997, 94:7192-7), and a fragment containing amino acids 1-110 binds Flk-1 as tightly as does VEGF165 (the human homologue of mouse VEGF164) (Christinger et al., Proteins, 1996, 26:353-7). In particular, it has been shown that residues in a hairpin loop between amino acids 80 and 90 are important for binding of VEGF to Flk-1.

All the VEGF molecules described above, as well as fragments and variants thereof, are contemplated as useful as the VPA to be used with the nucleic acid vector in the methods and compositions of the present invention. In certain preferred embodiments, VEGF165 is employed (e.g. conjugated or unconjugated to a nucleic acid vector such as AAV6 or AAV1). In other preferred embodiments, VEGF121 is employed as the VPA in the present invention (e.g. since it shares all of its sequence in common with the N-terminal 121 amino acids of VEGF 165 (Robinson and Stringer, J. Cell. Sci., 2001, 114:853-65). In other embodiments, a fragment of VEGF121, encompassing amino acids 98-109, is employed as the VPA in the present invention (e.g. conjugated or not conjugated to a nucleic acid vector such as AAV). It is noted that this fragment of VEGF121 is a good facilitator of vector delivery to muscle as shown in Example 3 below.

In certain preferred embodiments, fragments from VEGF121 (or any other VEGF molecule) could be used to modify the capsid structure of AAV vectors to render them inherently capable of vascular permeabilization without the need for added soluble VPA such as VEGF. Such fragments, include, but are not limited to are: VEGF164, VEGF165, VEGF121, VEGF1-110, VEGF 8-109, VEGF8-99, VEGF25-108, VEGF50-108, VEGF50-99, VEGF 70-108, VEGF 70-99, VEGF75-108, VEGF75-99 or any fragment similar to these fragments. Another protein that could be incorporated into a viral capsid is Substance P, which is only 11 amino acids in length (See, Chang et al., P. Nat. New Biol. 232:86-87, 1971, herein incorporated by reference). In regard to incorporating VEFG type molecules into an AAV capsid, one issue is that biologically active VEGF is an anti-parallel dimer. Biologically active VEGF dimers are readily obtained when VEGF monomers are produced in bacteria, yeast, and 293 cells (Ma, et al., 2001, Biomed Environ Sci 14:302-311; and Mohanraj et al., 1995, Growth Factors 12:17-27). A number of approaches could be employed to enable dimer formation on the capsid. First, one could transfect a CMV-VEGF expression plasmid into the 293 cell line to enable co-expression of soluble VEGF fragments together with the VEGF-modified capsid. Second, one could insert into the capsid gene an autodimerizing version of the appropriate VEGF fragment consisting of a cassette encoding two tandem fragments of VEGF separated by a short, flexible linker. This linker will enable formation of anti-parallel dimers in the capsid. One example of a linker is one of the short loops that connect the coiled-coil units of the dystrophin spectrin-like repeats (Koenig, 1990, J Biol Chem 265:4560-4566, herein incorporated by reference).

C. Empty Viral Capsids as VPAs

Another type of VPA are empty adeno-associated viral capsides (AAVs that do not contain viral nucleic acid). In preferred embodiments, the empty AAV capsids are AAV6 capsids. Example 5 below describes methods of generating different populations of AAV6 capsids (e.g. with different percentages of empty vs. nucleic acid containing capsids). In certain embodiments, compositions comprising less than 1% of empty capsids are employed to enhance systemic transduction of vectors (e.g. when intravenously injected). In other embodiments, compositions comprising at least 50%, or at least 95% or at least 99% empty capsids are employed to enhance systemic transduction of vectors. In further embodiments, VPAs (such as those described above) are combined with the empty capsids. In certain embodiments, only fragments of the AAV capsids (rather than the entire capsid) are employed to enhance systemic tranduction.

D. Additional VPAs

Additional potential VPAs that could be screened (e.g. repeating Example 1 but replacing VEGF with a candidate VPA) include, but are not limited to, placental growth factor (PIGF), platelet-derived growth factor (PDGF), VEGF-C, heterodimeric VEFG-A/PIGF, substance P, and basic fibroblast growth factor (bFGF). The ability of these agents may be compared by injecting them in the tail vein of a mouse together with $10^{11}$ vg of rAAVG-CMVβgal and examining the level of expression in various tissues in the mouse.

III. Nucleic Acid Vectors

The present invention contemplates the use of nucleic acid vectors with the compositions and methods of the present invention. The present invention is not limited by the choice of nucleic acid vector employed. In general, nucleic acid vectors suitable for use with the methods and compositions of the present invention, for example, should be able to adequately package and carry a nucleic acid sequence of interest (as well as sequences necessary for expression of the nucleic acid sequence in a cell). A number of suitable vectors are known in the art including, but are not limited to, the following: A) Adeno-Associated Viral Vectors; B) Adenoviral Vectors; C) Second Generation Adenoviral Vectors; D) Gutted Adenoviral Vectors; E) Lentiviral Vectors; and F) Retroviruses.

Those skilled in the art will recognize and appreciate that other vectors are suitable for use with methods and compositions of the present invention. Indeed, the present invention is not intended to be limited to the use of the recited vectors, as such, alternative means for delivering the compositions of the present invention are contemplated. For example, in various embodiments, the compositions of the present invention are associated with retrovirus vectors and herpes virus vectors, plasmids, cosmids, artificial yeast chromosomes, and bacterial artificial chromosomes. Exemplary delivery approaches are discussed below.

A. Adeno-Associated Virus Vectors

In preferred embodiments, the nucleic acid sequence of interest is inserted in adeno-associated vectors (AAV vectors), such as AAV6 or AAV1.

1. Serotypes of AAV

Adeno-associated viruses (AAV) are non-pathogenic members of the parvovirus family. At least six serotypes of AAV have been identified from human cells and tissues, and these are referred to as AAV serotypes 1-6, or simply AAV1-6

(Rutledge et al., J. Virol., 72:309-19, 1998, and Xiao et al., 73:3994-4003, 1999, herein incorporated by reference). Parvoviruses are known to infect many different species, and recently two additional non-human serotypes named AAV7 and 8 have been described (Gao et al., 2002, PNAS USA, 99:11854-9, and WO03052051, herein incorporated by reference). Another serotype, AAV9, is discussed in WO03052052 (herein incorporated by reference). It is also believed that a large number of additional AAVs have been discovered and will be made public in the near future (e.g. by James Wilson at Pennsylvania University, see Gao et al., J Virol. June 2004; 78(12):6381-8, herein incorporated by reference). These viruses display a broad host range, and the different serotypes display numerous differences in their tropism for different cell types (e.g. Chao et al., Mol. Ther. 2:619-623, 2000, and Grimm et al., Mol. Ther., 2003, 7:839-50). For example, serotypes AAV 1, 5 and 6 have been reported to be particularly effective at transducing muscle fibers from mice and/or humans (Scott et al., Neuromusc. Disord., 2002, 12(S):S23-S29. AAV vectors have been exploited by numerous laboratories to develop gene transfer vectors that may be of use in gene therapy applications. AAV vectors have a single stranded genome composed of approximately 4,700 bases flanked by short, inverted terminal repeats (Muzyczka, 1992, 158:97-129, herein incorporated by reference). The genome contains 2 genes, rep and cap, that encode 4 Rep proteins and 3 capsid proteins, VP1, VP2 and VP3. These proteins are generated by the use of alternate promoters and alternative splicing. The VP proteins form the viral capsid. The different forms differ from one another by the length of the N-terminal region, and 60 copies of the capsid protein are present in a viral particle in ratios of VP1:VP2:VP3 of 1:1:8.

Recombinant AAV vectors (rAAV) can be prepared in the laboratory using a variety of different methods (e.g., Collaco et al., Gene, 1999, 238:397-405, and Xiao et al., J. Virol., 1998, 72:2224-32). The rAAV vector genomes contain a gene expression cassette flanked by the terminal repeats (TR) from wild-type AAV. The AAV TRs are thus the only portion of wild-type AAV that is packaged into the recombinant AAV vector. Such a rAAV can be grown in tissue culture cells, such as human 293 cells, that have been co-transfected with a transfer plasmid and with a helper virus or with helper plasmids (e.g. Grimm et al, Hum. Gene Ther., 1998, 9:2745-60). The transfer plasmid is composed of a plasmid vector containing the recombinant AAV genome. The helper functions can be provided by infection of the 293 cells with herpes viruses, adenoviruses or by co-transfection with one or more plasmids carrying appropriate genes for helper function. In one such application, rAAV genomes are prepared by a three plasmid co-transfection method: the first plasmid is the terminal-repeat-expression cassette plasmid (transfer plasmid); the second plasmid contains the AAV genes rep and cap, and the third plasmid carries critical helper genes from adenovirus, such as E4, E2, and VARNA (Ferrari et al., Nature Med. 1997, 3:1295-1297). Another method described uses a two plasmid co-transfection system in which the transfer vector is co-transfected with a plasmid encoding rep, cap, and the aforementioned three adenoviral genes (e.g. Grimm et al., Mol. Ther. 2003, 7:838-50). Recombinant AAV vectors can be prepared from any of the reported serotypes 1-8 (or other that are discovered) using genomes, rep and cap genes derived from the individual wild-type AAV viruses. Alternatively, pseudotyped vectors may be prepared using an AAV2 genome, the rep gene from AAV2, and the cap gene from the particular serotype of interest (e.g., Rabinowitz et al., J. Virol. 2002, 76:791-801). If the cap gene is derived from AAV6, the vector is referred to as pseudotyped rAAV6 (Rutledge et al., J. Virol., 1998, 72:309-19).

rAAV vectors are particularly attractive for human gene therapy applications, as they have been reported to efficiently transduce numerous cell types and support stable, long-term gene expression without induction of inflammation, an immune response or other pathogenic responses. However, in some cases, such as in dystrophin-deficient muscles from the mdx mouse model for Duchenne muscular dystrophy (DMD), or in the sarcoglycan-deficient Bio14.6 hamster model for limb-girdle muscular dystrophy (LGMD), an inflammatory response has been observed following delivery of AAV2 vectors that express an immugenic protein, such as beta-galactosidase, under control of a ubiquitously active promoter, such as the human cytomegalovirus immediate early promoter. Other proteins delivered to the dystrophic mdx mouse, such as dystrophin, have not elicited an obvious immune response. Some studies have suggested that this immune response may depend on the pathologic state of the target tissue, whether or not a tissue-restricted promoter element, such as that derived from the muscle creatine kinase gene, is used and the intracellular localization of the expressed transgene.

2. AAV Capsids

The tropism of rAAV vectors is derived from the nature of the capsid gene used for growth and encapsidation of the vectors (Grimm et al., 2003 and Rutledge 1998). Several research groups have exploited the tropism of the different capsids to increase the transduction efficiency of several different tissues or cell types. For example, AAV1, AAV5 and AAV6 have been shown to display a greater ability to transduce skeletal muscle cells than does AAV2 (e.g. Scott et al., 2002). A number of investigators have attempted to modify the natural sequence or structure of either individual capsid proteins, or the overall structure of the viral capsid. For example, several groups have attempted to alter rAAV tropism by directly mutating the sequence of an AAV capsid gene. These mutations have taken the form of amino acid substitutions, additions, deletions and insertions (e.g. Buning et al., Gene Ther., 2003, 10:1142-51 and Grifman et al., Mol. Ther. 2001, 3:964-75). These sequence modifications have generally been within the middle of the capsid sequence. However, several reports have shown that larger sequences can be appended onto the C-terminal end of the VP3 protein. In theory, these types of modifications appear capable of generating rAAV vectors with tropism for almost any specific cell type.

Previous attempts to mutate AAV capsid proteins have been reported primarily for the AAV2 capsids, although at least one report focused on AAV1 (Hauck and Xiao, J. Virol., 2003, 77:2768-74) and another on AAV3 (Bowles et al., J. Virol, 2003, 77:423-32). However, the known capsid protein sequences are all quite similar, as shown by the published alignment of the AAV serotypes 2-6 capsid protein sequences. To date, only a few sites within the AAV2 capsid have been successfully mutated or used for insertion/deletion mutations that introduced new amino acid sequences. These sites have generally involved sequences thought to reside in loops located on the exterior side of the AAV capsid. Wu et al (J. Virol., 2000, 74:8635-47) performed an extensive mutational analysis of the AAV2 capsid gene, and found a number of discreet sequences within the sequence that could be mutated without loss of the ability of the recombinant vectors to be produced. Nonetheless, most of these mutants could not be packaged, or displayed a loss of the ability to transduce target cells. Shi et al (Hum. Gene Ther., 2001, 12:1697-711)

incorporated peptides up to 15 amino acids in length into multiple sites within the Vp1, 2 or 3 coding regions of the AAV2 capsid gene. Some of the modified viruses prepared with these mutant capsid genes were viable and able to be grown to high titers. In one example, those authors inserted a 15 amino acid peptide that binds to the luteinizing hormone (LH) receptor immediately after capsid amino acid 520, and showed that these rAAV particles were able to bind to cells that expressed high levels of the LH receptor. In another example, a 34 amino-acid peptide was inserted immediately after capsid amino acid 587 of AAV2. The rAAV particles grown in the presence of this modified capsid could be packaged and purified at high titer, and enabled tropism modifications by enabling binding of the inserted peptide and specific IgG proteins directed at different epitopes (Ried et al, J. Virol, 2002, 76:4559-66). In a third example, AAV2 capsid mutants were generated by inserting a 14 amino acid peptide into multiple loop structures of the capsid (Girod et al., Nat. Med., 1999, 5:1052-6). These authors reported that all the mutants they isolated supported efficient packaging of rAAV2 vector genomes, although only half expressed the inserted peptide on their outer surface. In a fourth example, Grifman et al incorporated a variety of peptides up to 13 amino acids in length into AAV2 capsids (Grifman et al., Mol. Ther., 2001, 3:964-75). These authors obtained the best results by inserting peptides at amino acid positions 449 (in loop III) and 588 (in loop IV). Insertion of these peptides was facilitated by deleting between 6 and 13 amino acids from the capsid sequence at the site of insertion.

From these examples it appears that the best success to date has been reported with insertions into the AAV2 capsid amino acid site 587 or 588 (Reid et al, 2002; Griffman et al, 2001). Amino acid 587 of the AAV2 capsid corresponds to amino acid 588 of the AAV6 capsid (Rutledge, 2001). The AAV6 capsid gene encodes 3 capsid proteins that all share a common C-terminal region (see, e.g., U.S. Pat. No. 6,156,303 to Rutledge et al. describing AAV6; herein incorporated by reference). The predicted amino acid sequence of these three proteins, VP1, VP2 and VP3 is shown in U.S. Pat. No. 6,156,303. The longest protein, VP1, is 736 amino acids in AAV6, and 735 amino acids in AAV2.

Recombinant AAV vector capsid proteins can also be modified to the variable region of single-chain antibodies. Yang et al (1998) used this approach to engineer a rAAV2 vector that incorporated an antibody chain specific for human CD34 cell surface receptors (Yang et al., Hum. Gene Ther., 1998, 9:1929-37). DNA sequences encoding this single chain antibody molecule were fused in-frame at the N-terminal sequence of the AAV2 VP2 protein. The resulting vectors displayed enhanced binding to a human CD34-positive myoleukemia cell line that was otherwise refractory to transduction by AAV2. Other groups have attempted to alter the tropism of AAV2 vectors by appending new amino acid sequences onto the C-terminal end of the VP3 protein. In one case, insertion of a 6-His (six histamines) tag onto the C-terminal end of the AAV2 capsid resulted in virions that did not display growth or transduction abnormalities. In contrast, Wu et al (2000) observed that incorporation of several different peptides between 5 and 9 amino acids in length prevented encapsidation of rAAV2 genomes. These results indicate that some sequences can be incorporated onto the C-terminus of VP3.

Chimeric AAV capsid genes have also been prepared by co-transfection of DNA fragments of the AAV3 capsid gene together with mutant and non-functional AAV2 capsid genes. Rescued virions all displayed altered tropism, which was shown to have occurred by homologous recombination between the AAV2 and 3 capsid genes, resulting in chimeric capsid genes that incorporated between 16 and 2,200 bases of the AAV3 capsid gene into the recombinant AAV2 capsid gene (Bowles et al., 2003). Another approach that attempted to identify sequences in AAV1 and AAV2 responsible for the tropism of those serotypes involved transferring discreet regions from AAV1 and AAV2 capsid genes to make hybrid AAV2/1 capsid vectors that displayed intermediate tropisms for muscle compared with the parental vectors (Hauck and Xiao, 2003). These studies also suggest that rAAV vectors can be grown in cell lines that express two or more different capsid genes derived from multiple different serotypes of AAV. Such recombinant AAV vectors are expected to display different cell binding characteristics than rAAV vectors prepared using a capsid gene from a single serotype.

Another approach to altering AAV tropism involves modifying the AAV2 capsid gene to encode a particular epitope. rAAV vectors prepared in the presence of this modified capsid protein could then be combined in vitro with an immunoglobulin, or antibody, that recognizes or binds to the epitope. If the antibody is a bi-specific single-chain antibody, such as those described by Haisma et al (Cancer Gene Ther., 200, 7:901-4), a second ligand can be attached to the antibody to increase the tropism of the rAAV-antibody complex for specific cell types by virtue of their increased binding affinity for receptors on the surface of those cells.

Methods similar to the above, in some embodiments, could be used such that rAAV particles are re-targeted to bind VEGF receptor proteins Flt1 or Flk1 (e.g. rAAV capsid conjugated to a VPA such as VEGF, see below). At least one group has incorporated a seven amino acid peptide into the capsid of rAAV2 at position 587, and the resulting modified vectors displayed enhanced targeting of human vascular endothelial cells (Nicklin et al., Mol. Ther. 2001, 4:174-81).

These examples have generally used a fully mutated capsid gene for generation of rAAV particles, such that all the capsid proteins incorporated into the capsid contain the same modification. It is also contemplated, however, that one could grow rAAV particles by co-transfecting the vector producing 293 cell line with a mixture of wild-type and mutated capsid genes such that the rAAV particles would contain only a subset of modified capsid proteins, as the AAV particle contains 60 copies of the capsid protein. A rAAV vector produced in such a manner would retain tropism characteristics that retain the natural tropism of the wild-type AAV serotype, for example for striated muscle, while also allowing increased binding to additional cell types or receptors, such as a receptor present on vascular endothelial cells. For example, if a rAAV vector were prepared in the presence of the AAV6 capsid gene and a mutant AAV6 capsid that incorporated a ligand for the VEGF receptor proteins Flt1 and Flk1 (e.g., Terman et al., Growth Factors, 1994, 11:187-95; and A; Autiero, 2003, 9:936-43, both of which are herein incorporated by reference), then that rAAV vector might display an increased ability to traverse vascular endothelial cell barriers in capillaries and transduce striated muscle cells.

B. Adenoviral Vectors

Self-propagating adenovirus (Ad) vectors have been extensively utilized to deliver foreign genes to a great variety of cell types in vitro and in vivo. "Self-propagating viruses" are those which can be produced by transfection of a single piece of DNA (the recombinant viral genome) into a single packaging cell line to produce infectious virus; self-propagating viruses do not require the use of helper virus for propagation. As with many vectors, adenoviral vectors have limitations on the amount of heterologous nucleic acid they are capable of delivering to cells. For example, the capacity of adenovirus is approximately 8-10 kb, the capacity of adeno-associated virus is approximately 4.8 kb, and the capacity of lentivirus is approximately 8.9 kb.

C. Second Generation Adenoviral Vectors

In an effort to address the viral replication problems associated with first generation Ad vectors, so called "second generation" Ad vectors have been developed. Second generation Ad vectors delete the early regions of the Ad genome (E2A, E2B, and E4). Highly modified second generation Ad vectors are less likely to generate replication-competent virus during large-scale vector preparation, and complete inhabitation of Ad genome replication should abolish late gene replication. Host immune response against late viral proteins is thus reduced [See Amalfitano et al., "Production and Characterization of Improved Adenovirus Vectors With the E1, E2b, and E3 Genes Deleted," J. Virol. 72:926-933 (1998)]. The elimination of E2A, E2B, and E4 genes from the Ad genome also provide increased cloning capacity. The deletion of two or more of these genes from the Ad genome allows for example, the delivery of full length cDNA dystrophin genes, or mini-dystrophin genes via Ad vectors [Kumar-Singh et al, Hum. Mol. Genet., 5:913 (1996)].

D. Gutted Adenoviral Vectors

"Gutted," or helper dependent, Ad vectors contain cis-acting DNA sequences that direct adenoviral replication and packaging but do not contain viral coding sequences [See Fisher et al. "Recombinant Adenovirus Deleted of All Viral Genes for Gene Therapy of Cystic Fibrosis," Virology 217: 11-22 (1996) and Kochanek et al. "A New Adenoviral Vector: Replacement of All Viral Coding Sequences With 28 kb of DNA Independently Expressing Both Full-length Dystrophin and Beta-galactosidase" Proc. Nat. Acad. Sci. USA 93:5731-5736 (1996)]. Gutted vectors are defective viruses produced by replication in the presence of a helper virus, which provides all of the necessary viral proteins in trans. Since gutted vectors do not contain any viral genes, expression of viral proteins is not possible.

Recent developments have advanced the field of gutted vector production [See Hardy et al., "Construction of Adenovirus Vectors Through Cre-lox Recombination," J. Virol. 71:1842-1849 (1997) and Hartigan-O'Conner et al., "Improved Production of Gutted Adenovirus in Cells Expressing Adenovirus Preterminal Protein and DNA Polymerase," J. Virol. 73:7835-7841 (1999)]. Gutted Ad vectors are able to maximally accommodate up to about 37 kb of exogenous DNA, however, 28-30 kb is more typical. For example, a gutted Ad vector can accommodate the full length dystrophin or cDNA, but also expression cassettes or modulator proteins.

E. Lentiviral Vectors

Vectors based on human or feline lentiviruses have emerged as another vector useful for gene therapy applications. Lentivirus-based vectors infect nondividing cells as part of their normal life cycles, and are produced by expression of a package-able vector construct in a cell line that expresses viral proteins. The small size of lentiviral particles constrains the amount of exogenous DNA they are able to carry to about 10 kb.

F. Retroviruses

Vectors based on Moloney murine leukemia viruses (MMLV) and other retroviruses have emerged as useful for gene therapy applications. These vectors stably transduce actively dividing cells as part of their normal life cycles, and integrate into host cell chromosomes. Retroviruses may be employed with the compositions of the present invention (e.g. gene therapy), for example, in the context of infection and transduction of muscle precursor cells such as myoblasts, satellite cells, or other muscle stem cells.

G. Size of Nucleic Acid Vectors

AAV particles have bee reported to be between 20-25 nm in diameter as determined by electron microscopy of purified viral particles (Xie et al., Acta. Crystallogr. D. Bioll. Crystallogr., 2003, 59:959-70). Adenovirus particles are icosahedral shaped and have a diameter between 70-100 nm. The data generated during the development of the present invention indicates that rAAV vectors are readily transferred to striated muscle via the vasculature using the systemic administration methods described herein, whereas adenoviral vectors do not accumulate to a large degree in muscle with this approach. Consequently, viral vectors around the size of AAV (e.g. vectors with a diameter around 10 nm to 50 nm or 5 nm to 70 nm) are the preferred vectors for gene delivery to muscle via the vasculature using the methods of the present invention. Other vectors with diameters in the range of 70-100 nm may also be transferred with these methods, although they may be less efficient (e.g. a higher dose may be required).

IV. Nucleic Acid Vector Conjugates

In some embodiments, the nucleic acid vectors of the present invention, such as AAV, are conjugated to a VPA or to a VPA receptor/ligand. The present invention is not limited by the method used to generate the nucleic acid vector conjugates. Below are a number of exemplary ways in which one nucleic acid vector, the AAV, may be mutated to allow for increased vascular permeabilization and subsequent penetration of the endothelial cell barriers lining capillaries.

In the first exemplary method, peptides derived from a VEGF molecule (e.g. a VEGF isoform) are directly incorporated into the AAV capsid by inserting a nucleic acid sequence encoding these peptides into the AAV capsid gene. These peptides may be a fragment (or variant) of a VEGF isoform up to the full size of the VEGF isoform. Preferred fragments of a VEGF isoform may range in size from 25 to 100 amino acids (see above) (e.g. Yano et al., Methods Mol. Med., 2003, 74:391-8, herein incorporated by reference). A similar method could be applied in which peptides from a number of other vascular permeabilizing proteins, such as placental growth factor (Autiero, et al., 2003, Tjwa, et al., 2003), are incorporated into the AAV capsid (e.g. using the capsid-peptide conjugation methods known in the art and described above in part II).

In a second method, the full-length, or various fragments from a VEGF isoform are appended onto the C-terminal end of the VP3 protein. This approach may be accomplished by cloning a nucleic acid sequence encoding the appropriate VEGF amino acid sequences onto the 3' end of the VP3 gene in an AAV helper plasmid. A similar method may also be used in which peptides from other vascular permeabilizing proteins, such as placental growth factor (PGF, also known as PLGF), are incorporated into the AAV capsid at the carboxy-terminal end of VP3.

In a third method, a single-chain variable region fragment (e.g. from a monoclonal antibody or Fab) that binds a vascular permeabilizing agent, such as VEGF164 or VEGF165, is appended onto the C-terminal end of the VP3 protein. This approach may be accomplished by cloning a nucleic acid sequence encoding the appropriate single-chain variable region fragment onto the 3' end of the VP3 gene in an AAV helper plasmid. The corresponding vascular permeabilizing agent, such as VEGF164 or VEGF165, is then be attached to rAAV particles grown in the presence of this modified capsid protein, to facilitate binding of the rAAV particle to the vascular permeabilizing agent in vitro.

In a fourth method, a single-chain variable region fragment (e.g. from a monoclonal antibody or Fab) that binds a receptor for vascular permeabilizing agent, such as one of the VEGF receptors Flt1 and Flk1, is appended onto the C-terminal end of the VP3 protein. This approach may be accomplished by cloning a nucleic acid sequence encoding the appropriate single-chain variable region fragment onto the 3' end of the VP3 gene in an AAV helper plasmid. rAAV particles grown in the presence of this modified capsid protein would be expected to display an increased affinity for the cell surface receptor for the appropriate vascular permeabilizing agent.

In a fifth method, an AAV capsid gene in an AAV helper plasmid is modified by insertion of a nucleic acid sequence encoding an immunoglobulin-binding domain derived from protein A. IgG molecules specific for one or more vascular permeabilizing agents (VPAs), such as VEGF165, are attached to rAAV particles grown in the presence of this modified capsid protein, via the protein A motif in the capsid, to facilitate binding of the rAAV particle to the vascular permeabilizing agent(s) in vitro. Such a modified rAAV particle would be expected to display an increased tropism for cells that express the receptor for the particular vascular permeabilizing agent, e.g. the VEGF receptors Flt1 and Flk1.

In a sixth method, a sequence encoding a particular epitope is incorporated into an AAV capsid gene of an AAV helper plasmid. rAAV particles grown in the presence of this modified capsid protein are combined in vitro with an immunoglobulin, or antibody, that recognizes or binds to the incorporated epitope. By using a bi-specific single-chain Fv (scFv) antibody that binds to the epitope as well as a vascular permeabilizing agent, such as VEGF165, the vascular permeabilizing agent is then be attached to the antibody to generate a rAAV particle physically attached to the vascular permeabilizing agent. Such a modified rAAV particle is expected to display an increased tropism for cells that express the receptor for the particular vascular permeabilizing agent, e.g. the VEGF receptors Flt1 and Flk1. It is also noted that, with this approach, one could also simply use a bi-specific single-chain antibody composed of an anti-epitope single-chain Fv antibody fused to an scFv antibody directed against either VEGF, or the VEGF receptor. Similarly, one could also simply use a bi-specific scFv antibody composed of an anti-AAV capsid scFv antibody fused to an scFv antibody directed against either VEGF, or the VEGF receptor.

In a seventh method, a purified, rAAV is biotinylated in vivo using the endogenous biotin ligase known to exist in human 293 cells. This directed biotinylation simply requires that a short biotin acceptor peptide be inserted into the capsid protein, at any of the various sites described in the above paragraphs, such as amino acid 587. The biotinylated rAAV capsid could then be combined in vitro with VEGF, or another vascular permeabilizing agent, conjugated directly to streptavidin or avidin, which display a high affinity for biotin. Such a modified rAAV particle are expected to display an increased tropism for cells that express the receptor for the particular vascular permeabilizing agent, e.g. the VEGF receptors Flt1 and Flk1. Alternatively, the biotinylated AAV particle could be conjugated to biotinylated antibodies against the VEGF-receptor, or against VEGF, using avidin as a linker.

V. Nucleic Acid Sequence of Interest

In some embodiments, the nucleic acid vectors of the present invention comprise a nucleic acid sequence of interest. Preferably, the nucleic acid sequence of interest is a therapeutic nucleic acid sequence (e.g. when the nucleic acid vector delivers the nucleic acid sequence of interest to the cells of a subject, the nucleic acid sequence of interest is expressed and provides a therapeutic benefit to the subject). For example, nucleic acid sequences that encode a protein that is defective or missing in a recipient subject, or a heterologous gene that encodes a protein having a desired biological or therapeutic effect (e.g. an antibacterial, antiviral, or antitumor function) are suitable nucleic acid sequences of interest. Other suitable nucleic acid sequences of interest include, but are not limited to, those encoding proteins used for the treatment of endocrine, metaloic, hematologic, cardiovascular, neurologic, musculoskeletal, urologic, pulmonary, and immune disorders, including such disorders as inflammatory diseases, autoimmune disease, chronic and infectious diseases, such as AIDS, cancer, hypercholestemia, insulin disorders such as diabetes, growth disorders, various blood disorders including various enemias, thalassemias, and hemophilia; genetic defects such as cystic fibrosis, Gaucher's disease, Hurler's disease, adenosine deaminase (ADA) deficiency, aging related symptoms (e.g. age related muscle wasting), cancer cachexia, and emphysema.

In certain embodiments, the nucleic acid sequence of interest encodes a protein that inhibits myostatin (GDF-8). Myostatin has been identified as a potent negative regulator of muscle fiber size during myogenesis and after birth (see, McPherron, Nature. 1997 387:83-90, herein incorporated by reference). The biologically active component of myostatin is a protein homodimer that targets membrane-bound activin receptors in skeletal muscle. The availability of biologically active myostatin is regulated by a) synthesis of the precursor protein, b) cleavage and dissociation of the myostatin propeptide to liberate the active, ligand-binding molecule, c) interaction between the active dimer and other proteins that negatively regulate its activity such as follistatin, Follistatin Related Gene (FLRG), and Growth and Differentiation Associated Serum Protein-1 (GASP-1) (see, Lee et al., Annu Rev Cell Dev Biol. 2004; 20:61-86, herein incorporated by reference), and d) negative feedback of signal transduction elements stimulated by myostatin. Attempts have been made to negatively regulate myostatin activity by reduction of circulating protein levels via infusion of myostatin specific antibodies (Bogdanovich et al., Nature. 2002 420:418-21, herein incorporated by reference), and inhibition of proteolytic activation of myostatin by over-expressing a modified, noncleaving synthetic precursor peptide (Lee and McPherron, PNAS, 2001, 98:9306-9311, herein incorporated by reference). Delivery of expression cassettes containing, for example, a muscle specific promoter and cDNA encoding components of follistatin isoforms could be employed to attempt to diminish or suppress the biological activity of endogenous myostatin and its negative effects on muscle fiber growth. Alternatively, overexpressing signal transduction elements that negatively regulate the pathways activated by myostatin (e.g, SMAD6 and SMAD7) after ligand receptor interaction could be employed as methods of suppressing myostatin-mediated inhibition of muscle hypertrophy (Zhu et al., Cytokine, 2004, 26:262-72, herein incorporated by reference). As such, in some embodiments, the present invention provides methods of systemic delivery of vectors to a subject such that myostatin inhibitors are expressed. In preferred embodiments, the subject has a muscle wasting disorder, such as in the muscular dystrophies, aging, or cancer cachexia, that is treated by this approach (e.g. at least some of the symptoms associated with the muscle wasting are reduced or eliminated). In certain embodiments, the subject is a member of the armed forces or an astronaut who might not exhibit symptoms of pathology, but who could benefit from treatment with the compositions of the present invention.

In some embodiments, the nucleic acid sequence of interest may not have therapeutic value. For example, the nucleic acid sequence of interest may be a reporter gene, or a gene used to increase muscle mass (e.g. in a farm animal or human athlete) or the nucleic acid sequence of interest improves physical appearance or alters physical appearance in an animal (e.g. a cosmetic type effect results).

The nucleic acid sequence of interest, in some embodiments, will code for a protein antigen. The antigen may include a native protein or protein fragment, or a synthetic protein or protein fragment or peptide. Examples of antigens include, but are not limited to, those that are capable of eliciting an immune response against viral or bacterial hepatitis, influenza, diphtheria, tetanus, pertussis, measles, mumps, rubella, polio, pneumococcus, herpes, respiratory syncytial virus, hemophilus influenza type b, chlamydia, varicella-zoster virus or rabies.

The nucleic acid sequence of interest may also be a normal muscle gene that is effected in a muscle disease (e.g. muscular dystrophies like Duchenne muscular dystrophy, limb-girdle muscular dystrophy, Landouzy-Dejerine muscular dystrophy, Becker's muscular dystrophy, ocular myopathy, and myotonic muscular dystrophy). For such muscular dystrophies, the nucleic acid may be a heterologous gene encoding the full length dystrophin gene (or cDNA sequence), BMD-minigene, AH2-R19 minigene, Laminin-a2, utrophin, a-sarcoglycan, and emerin. BMD mini-gene refers to dystrophin cDNAs containing internal truncations.

Preferred nucleic acid sequences of interest are dystrophin, preferably micro (mini) dystrophin constructs. Preferred mini-dystrophin constructs have 4, 8, or 16 spectrin like repeats (e.g. utrophin or dystrophin derived repeats). Preferred constructs are provided in WO0229056 and Harper et al., Nature Med., 8:253-261, 2002, both of which are explicitly incorporated by reference as if fully reproduced herein. These references describe constructs with a perfect number of spectrin like repeats (e.g. 4.0 repeats, or 8.0 repeats), as well as constructs that only have a limited number of the four natural hinge regions in the dystrophin gene. Other references that describe dystrophins of reduced size are as follows: Yausa et al. FEBS Letters 425:329-336, 1998, which describes a series of truncated dystrophin cDNAs containing 3, 2, 1, or 0 rod repeats (spectrin-like repeats; see FIG. 1 of this reference); Wang et al. PNAS, 97(25):13714-13719, Dec. 5, 2000 which describes a series of minidystrophin genes (e.g. with 5 and 6 rod repeats as shown in FIG. 1; see also WO0183695 to Xiao Xiao, published November 8; Phelps et al., Hum. Mol. Gen.; 4(8):1251-1258 (1995); Hauser and Chamberlain, J. of Endocrinology, 149:373-378 (1996); Rafael et al., Hum. Mol. Gen., 3(10):1725-1733 (1994); Cox et al., Nature, 364:725-729 (1993); and Hartigan-O'Conner and Chamberlain, Microscopy Research and Technique, 48:223-238 (February, 2000); U.S. Pat. No. 5,239,060; U.S. Pat. No. 5,541,074; U.S. Pat. No. 5,621,091; U.S. Pat. No. 5,430,129; U.S. Pat. No. 5,863,743; U.S. Pat. Nos. 5,260,209; 5,308,752; 5,449,616; and 5,686,073; Wells et al., Hum. Mol. Genet., 4(8):1245-50 (1995); WO9722696; and EP1059354; all of which are specifically herein incorporated by reference.

Figure 12:
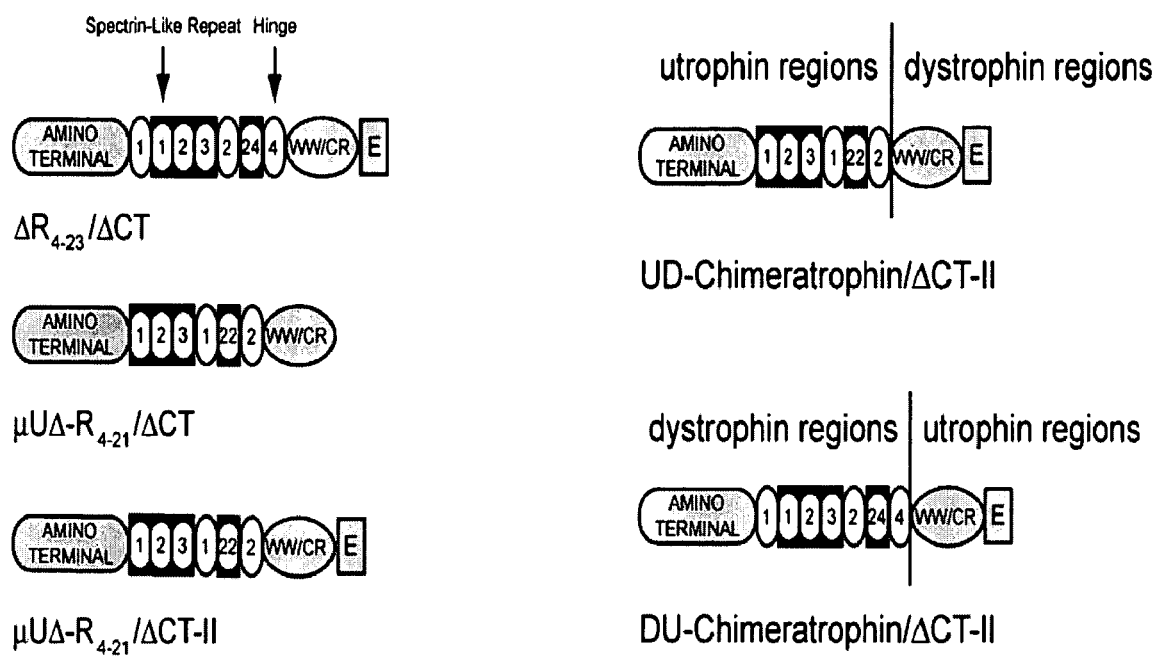
FIG. 12 shows schematics of various micro-dystrophin, micro-utrophin, and micro-dystrophin/utrophin chimeras.

Additional mini dystrohin, utrohpin, and dystrophin-utrophin hybrid micro-genes are shown in FIG. 12. FIG. 12 shows various preferred mini-gene type constructs that could be used with the present invention. The microdystrophin construct, $\Delta R_{4\text{-}23}/\Delta CT$, contains the actin binding amino-terminal domain, spectrin-like repeats 1, 2, 3, and 24, hinge domains 1, 2, and 4, as well as the WW and cysteine rich domains (designated by the shaded oval labeled, "WW/CR"). The microutrophin construct, $\mu U\text{-}\Delta R_{4\text{-}21}/\Delta CT$, contains analogous regions to those present in construct $\Delta R_{4\text{-}23}/\Delta CT$ with the exception of approximately 50 amino acids after the ZZ domain portion of the cysteine rich domain, designated in FIG. 12 as a shaded rectangle labeled "E". The amino acids contained in region "E" are not known to be required for binding to the dystroglycan complex. These approximately 50 amino acids are included in $\Delta R_{4\text{-}23}/\Delta CT$ but not in $\mu U\text{-}\Delta R_{4\text{-}21}/\Delta CT$; though these amino acids are present in the microutrophin construct, $\mu U\text{-}\Delta R_{4\text{-}21}/\Delta CT\text{-}II$. The constructs, UD-Chimeratrophin/$\Delta CT$-II and DU-Chimeratrophin, are hybrid proteins. Chimeratrophin/$\Delta CT$-II combines domains from the amino terminal domain through hinge 2 of $\mu U\text{-}\Delta R_{4\text{-}21}/\Delta CT$-II and the WW/CR domain of $\Delta R_{4\text{-}23}/\Delta CT$. DU-Chimeratrophin combines domains from the amino terminal domain through hinge 4 of $\Delta R_{4\text{-}23}/\Delta CT$ and the WW/CR domain from $\mu U\text{-}\Delta R_{4\text{-}21}/\Delta CT$-II. The sequence of three micro-utrophin sequences are shown in FIGS. 13A (SEQ ID NO:1), 13B (SEQ ID NO:2), and FIG. 13C (SEQ ID NO:6). Changes to these sequences could also be made and tested (e.g. substituted for the micro-dystrophins described in the Examples below). In this regard, additional micro-utrophin sequences could be identified and used to treat subjects with muscle wasting diseases.

As used herein, the term "dystrophin-like" nucleic acid refers to any nucleic acid that encodes a protein that could be used to functionally substitute for the dystrophin protein, including those that are able to link the actin cytoskeleton to dystrogylcan, or the actin cytoskeletal to the extracellular matrix (e.g. cDNA for CT GalNAc transferase, see, Nguyen et al., PNAS, 2002, 99:5616-21, herein incorporated by reference). Examples include, but are not limited to, micro-dystrophins, utrophin, micro-utrophins, dystrophin/utrophin chimeras, and micro-dystrophin/utrophin chimeras.

In certain embodiments, the nucleic acid sequence of interest is Igf-1 (e.g. any isoform from any species). Examples of nucleic acid sequences encoding Igf-1 are the mouse sequence (NM_010512) and the rat sequence (NM_178866). Additional examples include murine Igf-I Ea which contains exons 1,3,4,6 (SEQ ID NO:4), murine Igf-I Eb which contains exons 1,3,4,5,6 (SEQ ID NO:3), and human Igf-1 (SEQ ID NO:5). Vectors encoding Igf-1 may be administered to subject to treat muscle wasting disorders and particularly to treat muscle wasting associated with aging (e.g. treat a human 65 or older, 70 or older or 75 or older). For example, methods for systemic delivery if Igf-1 similar to those described in Example 8 (e.g. except used to treat a human with a human form of the Igf-1 sequence) may be employed (e.g. to treat an elderly human). Preferably, the Igf-1 leads to over-expression of Igf-1 in the subject (e.g. 2 times, 10 times, or 30 times or 50 times the natural level of Igf-1).

In particular embodiments, the present invention provides methods of treating a subject with both Igf-1 and a dystrophin type nucleic acid (full or micro-dystrophin, utrophin, micro-utrophin, dystroph-utrophin chimeric, or any other sequence that can effectively substitute for dystrophin) such that both Igf-1 and the dystrophin type protein are expressed in a subject. As described in Example 7 below, it has been determined that the combination of Igf-1 and dystrophin has a synergistic affect in vivo that allows muscle wasting type disorders to be effectively treated. Methods similar to Example 7 could be employed to treat a human in need of such treatment. The present invention also provides kits and compositions comprising vectors with both Igf-1 and dystrophin like sequence (e.g. in the same vector or different vectors; or in the same composition or separate compositions).

Nucleic acid sequences of interest may also be antisense molecules (e.g. for blocking the expression of an abnormal muscle gene). The nucleic acid sequence may also code for proteins that circulate in mammalian blood or lymphatic systems. Examples of circulating proteins include, but are not limited to, insulin, peptide hormones, hemoglobin, growth factors, liver enzymes, clotting factors and enzymes, complement factors, cytokines, tissue necrosis factor and erythropoietin. Nucleic acid sequences of interest may also genes encoding proteins that are to be produced in muscle cells in vitro or in vivo.

In some embodiments, the nucleic acid sequence of interest is an siRNA (RNAi) molecule that is able to suppress a targeted RNA transcript. RNAi represents an evolutionary conserved cellular defense for controlling the expression of foreign genes in most eukaryotes, including humans. RNAi is triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference. siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing Brummelkamp et al, Science 2002; 296:550-3; and Holen et al, Nucleic Acids Res. 2002; 30:1757-66, both of which are herein incorporated by reference.

In certain embodiments, the nucleic acid sequences of interest are operably linked to a tissue-specific promoter and/ or enhancers. In this regard, expression of the nucleic acid sequence of interest can be primarily localized to one target tissue type. Examples of muscle specific promoters and enhancers are found in WO0206495, herein incorporated by reference in its entirety. In some embodiments, the sequence of interest is alpa-7 intergrin (see, Burkin et al., J. Cell. Biol., 2001, 152:1207-8, herein incorporated by reference).

VI. Therapeutic Administration

As indicated above, the preferred route of administration of the compositions of the present invention is systemic administration to a blood vessel of a subject without one or more systemic administration aids. However, the present invention is not limited to un-aided systemic administration or to only systemic administration. For example, in some embodiments, the compositions of the present invention (e.g. nucleic acid vector with a VPA, or high doses of AAV6) are administered to a subject via a route selected from: intravenously, intramuscularly, subcutaneously, intradermally, intraperitoneally, intrapleurally, intrathecally, orally, rectally or topically. In some embodiments, formulations for such administrations may comprise sterile water or physiological saline.

Data gathered during development of the present invention has shown that while co-delivery of AAV6 and VEGF led to efficient gene transfer to striated muscle, if the vector is administered 10 minutes after the VEGF, the effect is largely lost. These observations indicate that vector should be delivered within about 5 minutes of administration of a VPA (e.g. VEGF), preferably within 2 minutes of VPA administration, more preferably within 30 seconds of VPA administration, and most preferably the vector and VPA are co-administered (e.g. as a single combined combination).

In other embodiments, the VPAs described above (including VEGF and empty AAV6 capsids) are pre-injected into the vascular of a subject. After pre-injection (pre-penneabilization) vectors with a sequence are then injected into the subject (e.g. within 30 seconds, 2 minutes, or 10 minutes). In other embodiments, the time per single infusion employed with the methods of the present invention varies from 3 second to 60 minutes (e.g. 5 second, 45 second, 10 minutes or 30 minutes).

As noted above, systemic administration of the compositions of the present invention can be to the veins or arteries or to both. Also, various catheters can be employed to access various locations in a subject. In certain embodiments, the maximal dosage of AAV6 in solution is about $10^{15}$ particles per ml.

In certain embodiments, the VPA is initially administered with the vector (e.g. in the same composition or separate compositions administered close in time), and then a second administration occurs later (e.g. 1 min, 5 min, 15 min, 1 hour or 3 hours later) that contain only the VPA and not additional vector. While not limited to any mechanism, it may be that additional blood circulating vectors could still be present in the subject at the time of the second administration such that the VPA administration allows the vectors to reach target cells and tissues without the need for additional vectors. In additional embodiments, localized heat and/or exercise are used to increase transduction efficiencies. In certain embodiments, localized ultrasound is used to heat the limb.

In some embodiments, vector administration is repeated a number of times, while avoiding or minimizing an immune response from a subject. In particular embodiments, the vector is administered to the subject over a period of 5-10 days. While not limited to any mechanism, it is believed that human immunity to the vectors (e.g. AAVs) takes about 5-10 days to develop, allowing repeat administration in this time window. In other embodiments, transient immune suppression is utilized to prevent an immune response (e.g. a humoral immune response to viral capsid proteins).

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); DS (dextran sulfate); and C (degrees Centigrade).

EXAMPLE 1

Adeno-Associated Viral Transduction with VEGF

This example describes systemic administration of an adeno-associated virus in combination with VEGF to animals without the use of systemic administration aids. This example also describes systemic administration of AAV6 without a vascular permeabilizing agent and without the use of systemic administration aids.

A. Materials and Methods

The following section describes the general procedure used to administer adeno-associated viral genomes and VEGF to mice.

Virus Production:

Recombinant adeno-associated virus (rAAV) vectors containing the various promoter and transgene casettes (see below) flanked by AAV serotype 2 terminal repeats were packaged using the Rep and Cap open reading frames of AAV serotype 6. To generate virus, 293D cells were transfected at a density of 3.5 to $4.0 \times 10^6$ cells per 10 cm diameter tissue culture dish. Transfection was carried out via calcium phosphate precipitation. Each 10 cm diameter plate was transfected with 20 µg of the packaging plasmid, pDG6, and 10 µg of the appropriate vector genome containing plasmid. Medium was exchanged to serum free medium 16 to 24 hours post transfection and 72 hours post transfection cells and medium were collected. The cells and medium were reduced to a cleared lysate via passage through a microfluidizer (Microfluidics, Newton, Mass., model M110S) and loaded onto a HiTrap Heparin column (Amersham, N.J.) using an AKTA-purifier 10 HPLC (Amersham). Vectors were eluted from the column in 400 mM NaCl supplemented Ringer's solution and dialyzed to Ringer's.

Experimental Animals:

All experimental manipulation of animals was approved by the Institutional Animal Care and Use Committee (IACUC) of the University of Washington. Animal strains used were either the wild-type, C57Bl/10J, or dystrophic, C57Bl/10ScSn-Dmd-mdx/J.

Viral Injections:

Young adult (6-8 wk) mice were injected with a range of rAAV $\sim 2.5 \times 10^{10}$ to $\sim 1 \times 10^{13}$ vector genomes in 250 µl via tail vein while conscious. Mice were administered 0-20 µg of recombinant human VEGF-165 (R & D Systems, Minn.) in 50 µl of Ringer's solution containing 0.05% mouse serum albumin and 2 IU heparin either as i.v. pre-treatment 10 min prior to administration of vector, or as i.v. co-treatment with vector. The co-administration of vector and VEGF intravenously is our principal method of facilitating systemic delivery, although we have also conducted pilot studies utilizing intraperitoneal and intrathoracic injections of vector and have observed appreciable transduction in musculature of the thorax and adjacent limb muscles. Following vector administration, animals were returned to their cages where they remained under observation until sacrifice at chosen time points for tissue harvest and analysis.

B. AAV6-CMV-LacZ

This section describes the results of experiments with an AAV6 containing the lacZ gene with the constitutive CMV promoter (AAV6-CMV-LacZ).

FIG. 1 shows a plate demonstrating the gray/black muscles of mice receiving vector and VEGF/heparin, as well as mice receiving vector alone. The dark shading is a reaction generated from the enzyme produced by the gene (LacZ) delivered by the virus. In particular, FIG. 1 demonstrates transduction of cardiac, trunk, and limb muscles of mice following systemic delivery of an AAV6-CMV-LacZ delivered via a single I.V. injection into the tail vein of adult animals. Note the differences in intensity of staining between rows 2 and 3 in FIG. 1, indicating the greatly increased transduction efficiency with co-treatment of VEGF. The staining of row two alone however, is greater than similar results reported in the literature, illustrating the value of the AAV6 serotype for transduction of muscle.

Figure 2:
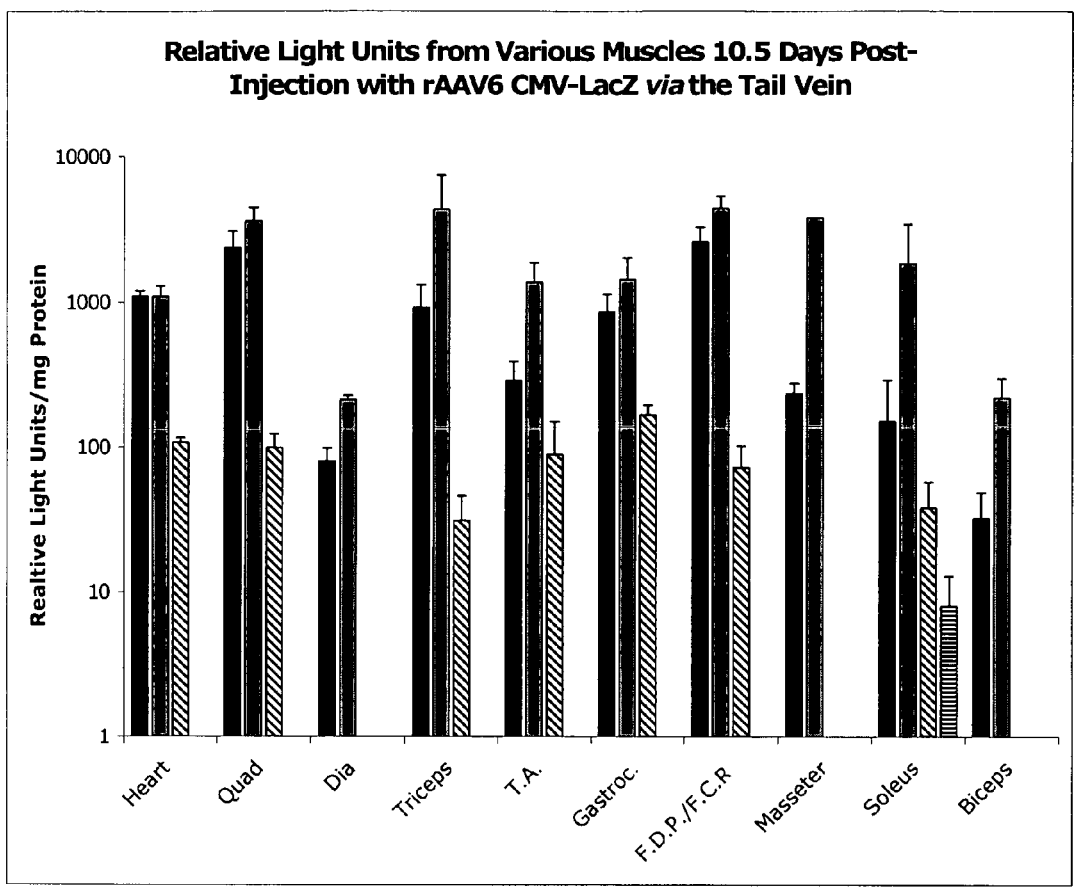
FIG. 2 shows a graph demonstrating the enzymatic activity measured in muscles and various organs from mice receiving various doses of vector with and without co-treatment of VEGF and heparin. In particular.

FIG. 2 shows a graph demonstrating the enzymatic activity measured in muscles and various organs from mice receiving various doses of vector with and without co-treatment of VEGF and heparin. In particular, FIG. 2 shows β-galactosidase activity (driven by the CMV promoter) in various muscles and organs following systemic delivery of $2 \times 10^{11}$ or $10^{12}$ doses of viral vector with and without VEGF. Virus was injected into young adult mice (6 to 8 weeks) while conscious as a bolus in a volume of ~300 µl into the tail vein. Animals were sacrificed approximately 10.5 days post injection. Muscles and organs were isolated and homogenized. The extract was used in a luminescent assay for β-galactosidase activity. If bars are absent it indicates a level of activity not detectable above background.

Data was collected for the following tissue types: masseter, FDP/FCR (flexor digitorum brevis/flexor carpi radialis), bicep, tricep, heart, diamprham, quadricep, gastocnemius, masseter, soleus, tibialis anterior, eye, brain, lung, intestines, liver, kidney, spleen, and testes. Data was assembled by determining which groups were significantly different from uninjected values, and then subtracting the uninjected values from the significant groups to display the level of activity above background. FIG. 2 does not display all of the non-muscle organs (i.e. eye, brain, lung, intestines, liver, kidney, spleen, and testes) as they failed to express levels of activity above uninjected controls.

All $10^{12}$ genome groups are significantly different from the $2 \times 10^{11}$ genome groups. All probability levels are a minimum $\leq 0.05$ according to Student's t-test. In FIG. 2, the following designations were used: solid black bar=$10^{12}$ vector genomes delivered with 10 µg V.P.F; solid grey bar=$10^{12}$ vector genomes delivered; diagonally hashed bars=$2 \times 10^{11}$ vector genomes delivered with 10 µg V.P.F; horizontally hashed bar=$2 \times 10^{11}$ vector genomes delivered. Values in FIG. 2 equal to or exceed transduction via intra-muscular injection previously observed. It is noted that these levels do not directly relate to the percent positive muscle fibers within a muscle (i.e. two muscles with different total activities may have the same percent muscle fibers transduced due to differing levels of enzyme within each individual fiber.)

FIG. 2 also shows that, with the exception of soleus limb muscle, no other tissue from $2 \times 10^{11}$ does mice without VEGF failed to register above controls. Thus, this figure demonstrates that there is considerable differences in the level of transduction achieved at the low dose ($2 \times 10^{11}$) with VEGF compared to without VEGF (i.e. VEGF made a big difference in transduction efficiency at $2\times10^{11}$ as only soleus limb muscle was above background at this level without the presence of VEGF). Therefore, the co-administration of VEGF with viral vector allows a lower dose of viral vector to be used in order to see significant transduction, which will help reduce concerns of viral load in clinical administration.

Figure 3:
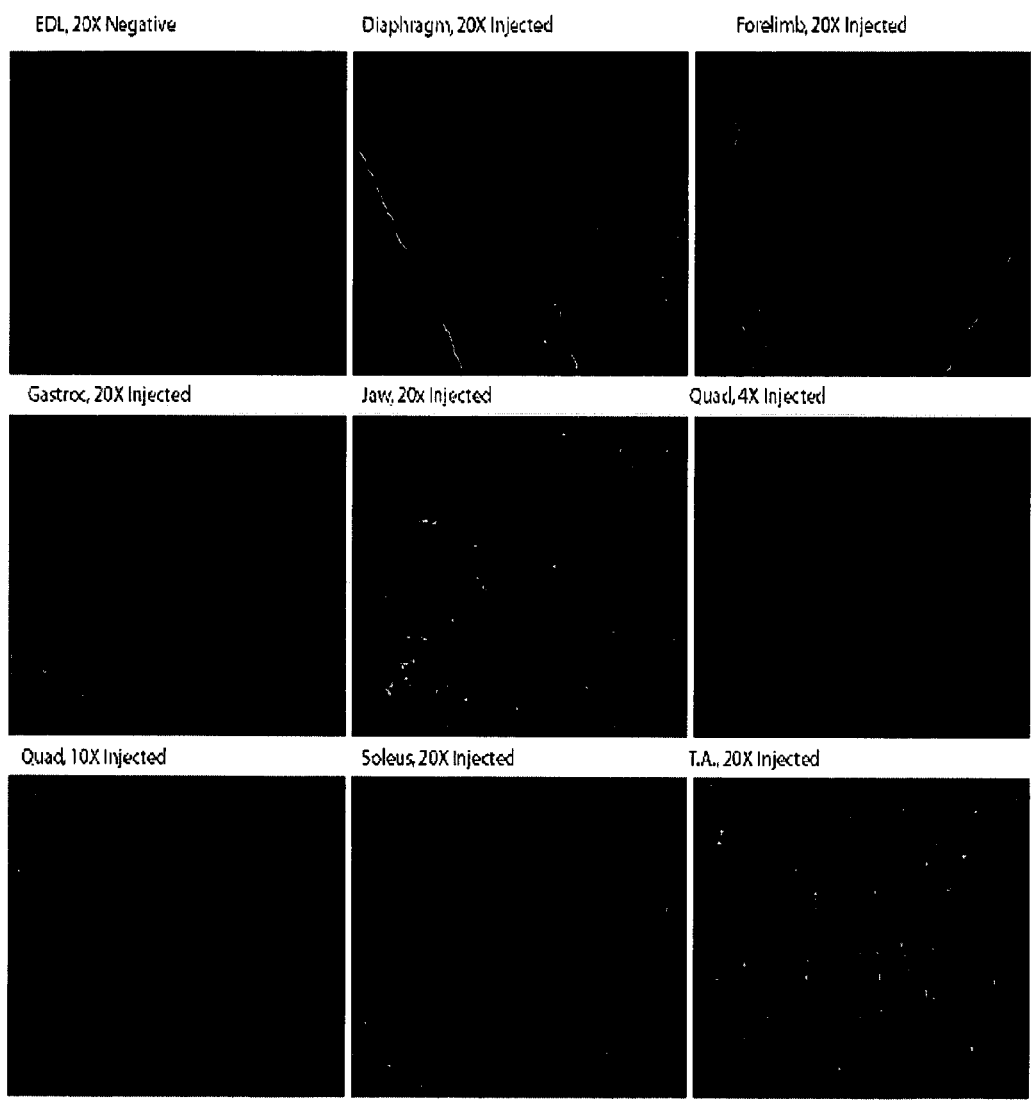
FIG. 3 shows various muscles of the body transduced with a gene encoding β-galactosidase following a single i.v. injection (using the AAV6-CMV-LacZ constructs into a conscious animal). The gray staining is indicative of positive signal.

FIG. 3 shows various muscles of the body transduced with β-galactosidase following a single i.v. injection (using the AAV6-CMV-LacZ constructs into a conscious animal). The gray staining is indicative of positive signal, $1\times10^{12}$ vector genome and 2 IU of heparin were delivered into a conscious mouse via the tail vein in a bolus of ~300 µl. The mice were sacrificed approximately 11 days post injection. Note that FIG. 3 shows that the various muscles exhibit approximately 90% or above transduction on the basis of individual muscle fibers which stain positive for β-galactosidase activity. These results compare favorably or exceed reported values in the literature using intramuscular injections (which was the most effective method to date, although limited in the amount of muscular tissue transduced). Similar results were seen when the virus and heparin were administered with VEGF though this vasodilator and permeability factor was not essential for widespread transduction at this viral dose.

Figure 4:
FIG. 4 shows a transverse section of a mouse heart harvested 11 d after a single systemic delivery of $1 \times 10^{12}$ viral genomes (i.e. about $4 \times 10^{13}$ vg/kg) of AAV6-CMV-LacZ vector in conjunction with 10 ug VEGF via the tail vein into a conscious mouse. This heart section was reacted for activity of the β-galactosidase transgene delivered by the vector, and transduced cells present as gray in FIG. 4.

FIG. 4 shows a transverse section of a mouse heart harvested 11 d after a single systemic delivery of $1\times10^{12}$ viral genomes (i.e. about $4\times10^{13}$ vg/kg) of AAV6-CMV-LacZ vector in conjunction with 10 ug VEGF via the tail vein into a conscious mouse. This heart section was reacted for activity of the β-galactosidase transgene delivered by the vector, and transduced cells present as gray in FIG. 4. As shown in FIG. 4, virtually the entire heart muscle is gray from reporter gene activity (i.e. this image demonstrates that greater than 90% of the myocardial tissue can be successfully transduced via a single intravenous administration of vector to a conscious adult mammal). This level of transduction elicits an ~10,000 fold increase in β-galactosidase activity compared with the hearts of untreated mice. It is noted that prior to this result, the art had not acknowledged that the AAV vector could generate an immune response in an adult wild type mouse, but such high levels of expression of this reporter gene (which is of bacterial origin) have been achieved in this example that the mouse started to react against it (very surprising result in non-diseased models). It is also noted that immunogenicity concerns can be addressed with tissue specific promoters (e.g. heart or muscle) and using a nucleic sequence of interest that is not immuogenic.

C. AAV6-CK6-LacZ

This section describes the results of experiments with an AAV6 containing the lacZ gene with the muscle specific creatine kinase promoter driving expression of the β-gal reporter gene (AAV6-CK6-LacZ). Various muscles of the body (mouse body) were transduced with β-galactosidase following a single i.v. injection of AAV6-CK6-LacZ. The results of this administration were seen after various muscle groups were isolated from the sacrificed mice. The blue staining in these muscle groups (not shown) was indicative of positive signal. $1\times10^{12}$ or $1\times10^{13}$ vector genomes were delivered with 10 µg VEGF-165 (also known as vascular permeability factor, VPF) and 2 IU of heparin into a conscious animal via the tail vein in a bolus of ~300 µl. The animals were sacrificed 14 days post injection. The results revealed a result approximately equal to outcomes achieved using 10 fold less vector containing CMV-LacZ which demonstrates the importance of intelligent promoter-transgene configuration in vector design. These results compare favorably or exceed reported values in the literature using intramuscular injections, the most effective method to date though limited in the amount of muscular tissue transduced.

D. AAV6-CK6-Micro-Dystrophin

This section describes the results of experiments with an AAV6 containing a micro-dystrophin gene with the muscle specific CK6 promoter (AAV6-CK6-micro-dystrophin). The micro (or "mini") dystrophin used in this example (ΔR4-R23-Δ71-78) is the same construct shown in FIG. 5b in Harper et al., Nature Med., 8:253-261, 2002 (herein incorporated by reference). Other micro-dystrophin constructs shown in this paper (e.g. FIG. 1a) as well as in WO0229056 (herein incorporated by reference) could have been used in this example. FIG. 27 of WO0229056 also shows the micro-dystrophin construct used in this example (i.e. it shows ΔR4-R23-Δ71-78).

Figure 5:
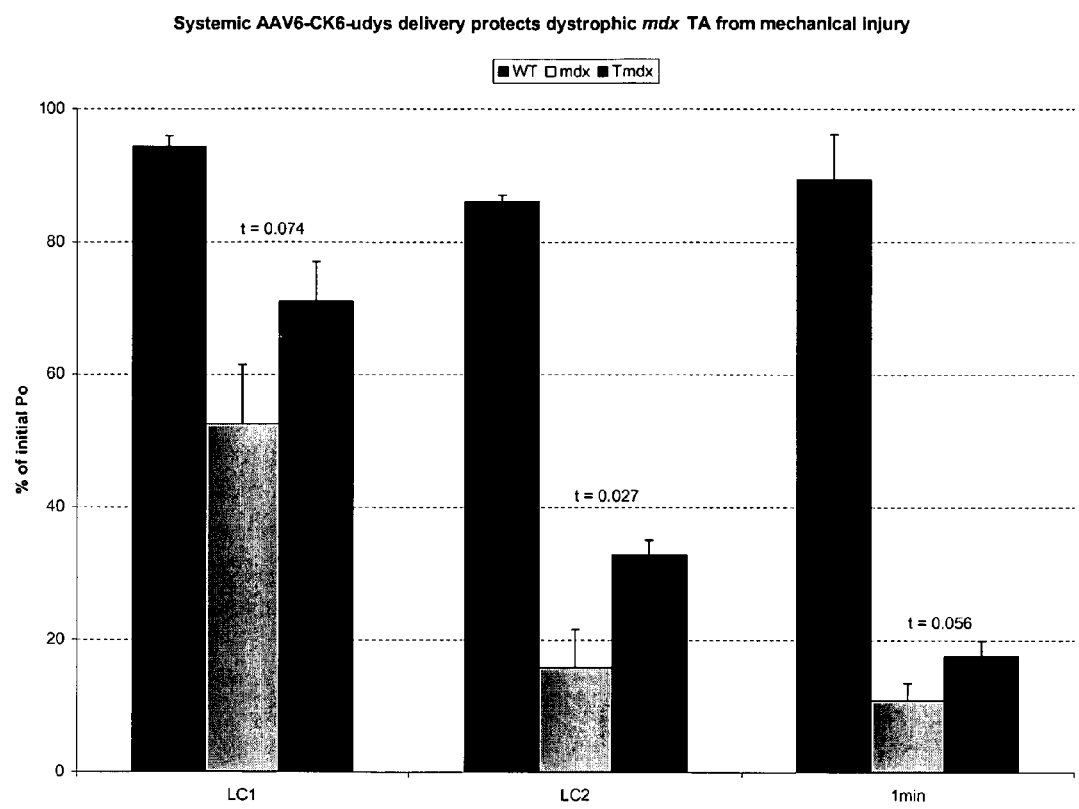
FIG. 5 demonstrates a functional correction of dystrophic muscle (tibialis anterior) following a single systemic administration of $1 \times 10^{12}$ viral genomes of pseudo-typed AAV6 CK6-micro-dystrophin.

FIG. 5 demonstrates a functional correction of dystrophic muscle (tibialis anterior) following a single systemic administration of $1\times10^{12}$ viral genomes of pseudo-typed AAV6 CK6-micro-dystrophin. Virus was delivered with 10 µg of V.P.F. and 2 I.U. of heparin in Ringer's supplemented with 0.08% mouse serum albumin. Animals were injected at 6-8 weeks of age and sacrificed at 8 weeks post injection. The two animal strains used were the wild-type C57B1/10J and the dystrophic C57B1/10ScSn-Dmd-mdx/J.

The assay with the mice in this example was a contraction-induced injury type assay. It is known that "stretches" do considerable damage to dystrophic muscle, and dystrophin has been shown to protect muscle fibers from damage from stretches (known officially as eccentric or lengthening contractions). This procedure is described in Delloruso et al., J. Muscle Res. and Cell Motility, 22:467-475, 2001, herein incorporated by reference. Briefly, in this example, the muscles of mice were administered a single stretch whilst maximally stimulated (i.e. to cause injury, the magnitude of which depends on how fragile the particular mouse strain happens to be). After a 10 second rest, a second stretch is administered, and after an additional 10 second rest, the procedure is repeated for a third time. LC1 in FIG. 5 is the maximum force generated by the muscle 10 s after it has endured a single contraction induced injury. LC2 in FIG. 5 is the maximum force generated by the muscle 10 s after it has been subjected to the second contraction induced injury. "1 min" in FIG. 5 is the maximum force produced by the muscle when recorded 60 s after the third stretch has been applied. Values in the graph have been presented relative to the initial force output of respective muscles, so the smaller the bar, the more severe the deterioration in force production experienced as a result of the stretch protocol. The t statistic is given on the graph for a one tailed t-test and refers to the difference between mdx and treated mdx (Tmdx) mice. This data represents a partial protection from contraction induced injury following a systemic delivery on par with the best results to date from a direct intramuscular injection of virus.

Figure 6:
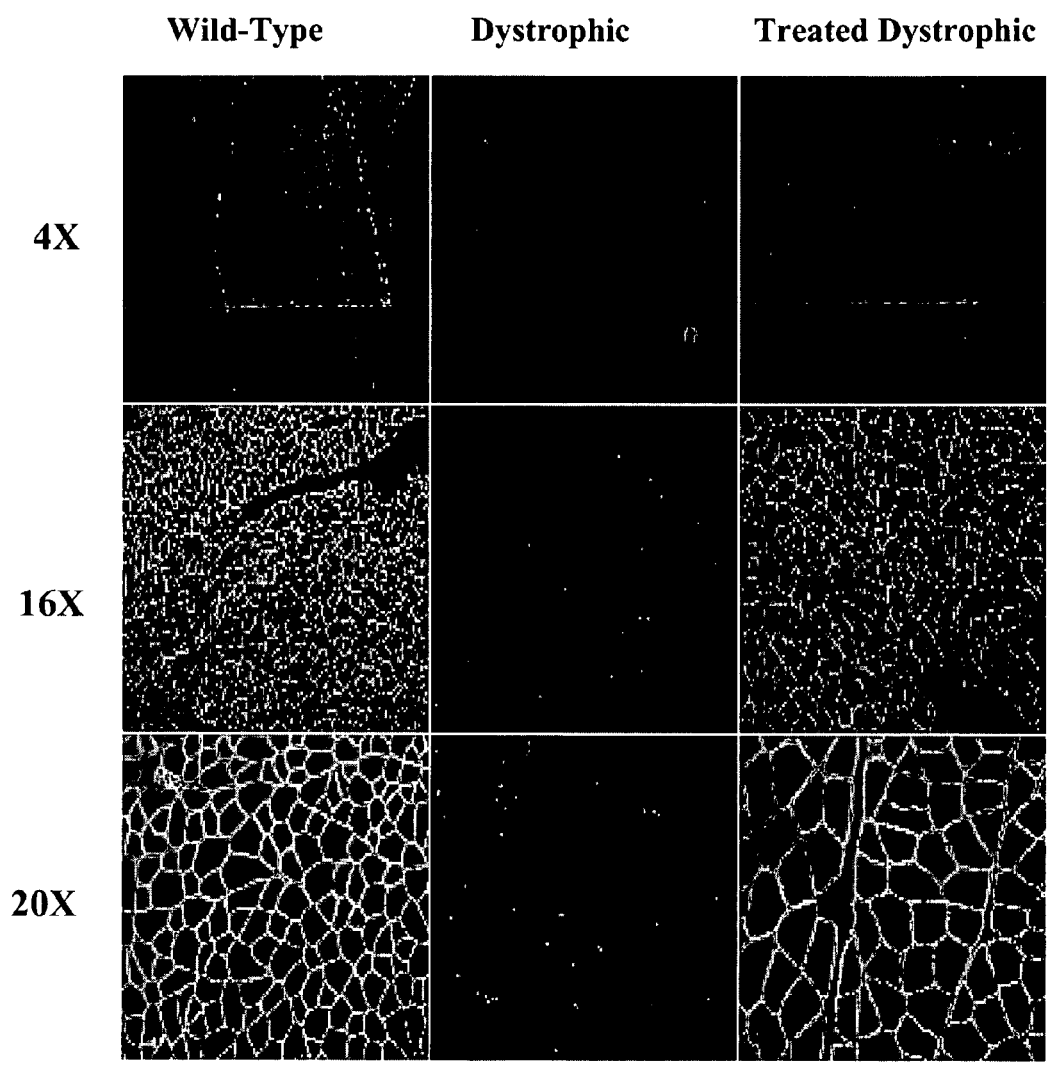
FIG. 6 shows that dystrophic animals have extremely widespread expression of approximately wild-type levels of micro-dystrophin in the quadriceps (Quad) muscle following systemic delivery of pseudo-typed AAV6 CK6-micro-dystrophin.
Figure 7:
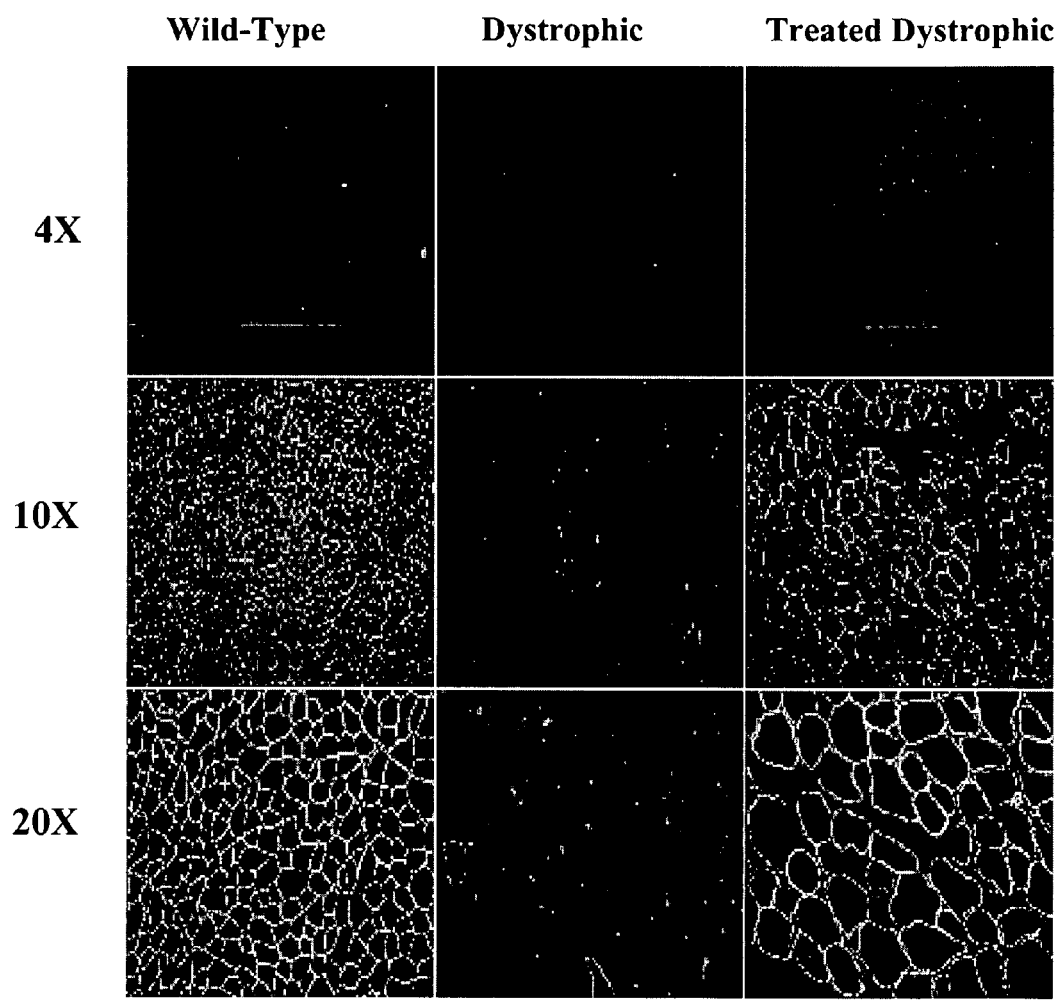
FIG. 7 shows that dystrophic animals have extremely widespread expression of approximately wild-type levels of micro-dystrophin in the tibialis anterior following systemic delivery of pseudo-typed AAV6 CK6-micro-dystrophin.

FIGS. 6 and 7 demonstrate high levels of mini-dystrophin expression in various muscle groups in mice following a single intravenous injection of AAV6-CK6-mini-dystrophin with VEGF. In particular, $1\times10^{13}$ viral genomes of pseudo-typed AAV6-CK6-micro-dystrophin were delivered in a 300 µl bolus with 10 µg of V.P.F. (VEGF) and 2 I.U. of heparin in Ringer's supplemented with 0.08% mouse serum albumin. The bolus was delivered via the tail vein. FIGS. 6 and 7 above demonstrate that dystrophic animals have extremely widespread expression of approximately wild-type levels of micro-dystrophin in both the quadriceps (Quad) muscle (FIG. 6), as well as in the tibialis anterior (T.A., FIG. 7), following systemic delivery of pseudo-typed AAV6 CK6-micro-dystrophin. Wild-type animals were of the C57B1/10J strain. Dystrophic and treated dystrophic animals were of the C57B1/10ScSn-Dmd-mdx/J strain. Animals were injected at between 6-8 weeks of age and tested 6 weeks post injection. It is noted that that these results are dramatic, and until the present invention, are not a result that was envisages as achievable in the scientific community.

Similar levels of dystrophin expression (as shown in FIGS. 6 and 7) were also observed in other muscles throughout the body including (but not limited to) the masseter, forelimb muscles, triceps, intercostals muscles, quadriceps. This specific vector did not elicit significant dystrophin expression in either the heart or the diaphragm, but this is attributable to the activity (or lack thereof) of the CK6 promoter cassette used, within these muscles. Other vectors with a constitutive promoter (such as CMV) demonstrate strong expression in the heart and diaphragm.

EXAMPLE 2

Systemic AAV Administration to a Large Mammal

Figure 8:
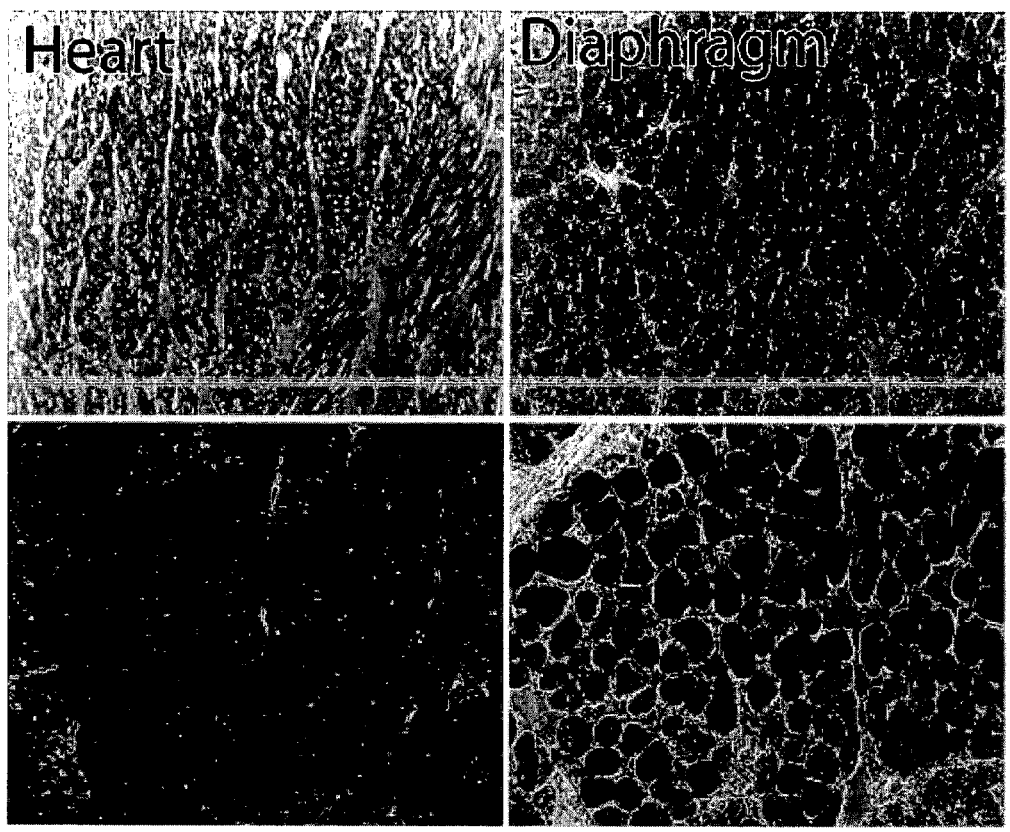
FIG. 8 shows results from Example 2 where rAAV6/RSV-hpAP was injected into the jugular vein of a 2 month old beagle and heart and diaphragm tissue was examined for hpAP expression.

This Example describes systemic AAV transduction in a dog. In this example, $4 \times 10^{13}$ vg/kg of rAAV6/RSV-hpAP (hpAP is human placental alkaline phosphatase; RSV is a promoter from Rous Sarcoma Virus) was injected into the jugular vein of a 2 month old beagle. Analysis of hpAP expression in the heart and diaphragm occurred at 3 weeks. The results are presented in FIG. 8, with the top two panels showing a control and the bottom two panels showing the injected canine tissue. This Example could be repeated with the addition of a vascular permeabilizing agent, such as VEGF-A.

EXAMPLE 3

Systemic Transduction with VEGF-$A_{121}$

Figure 9:
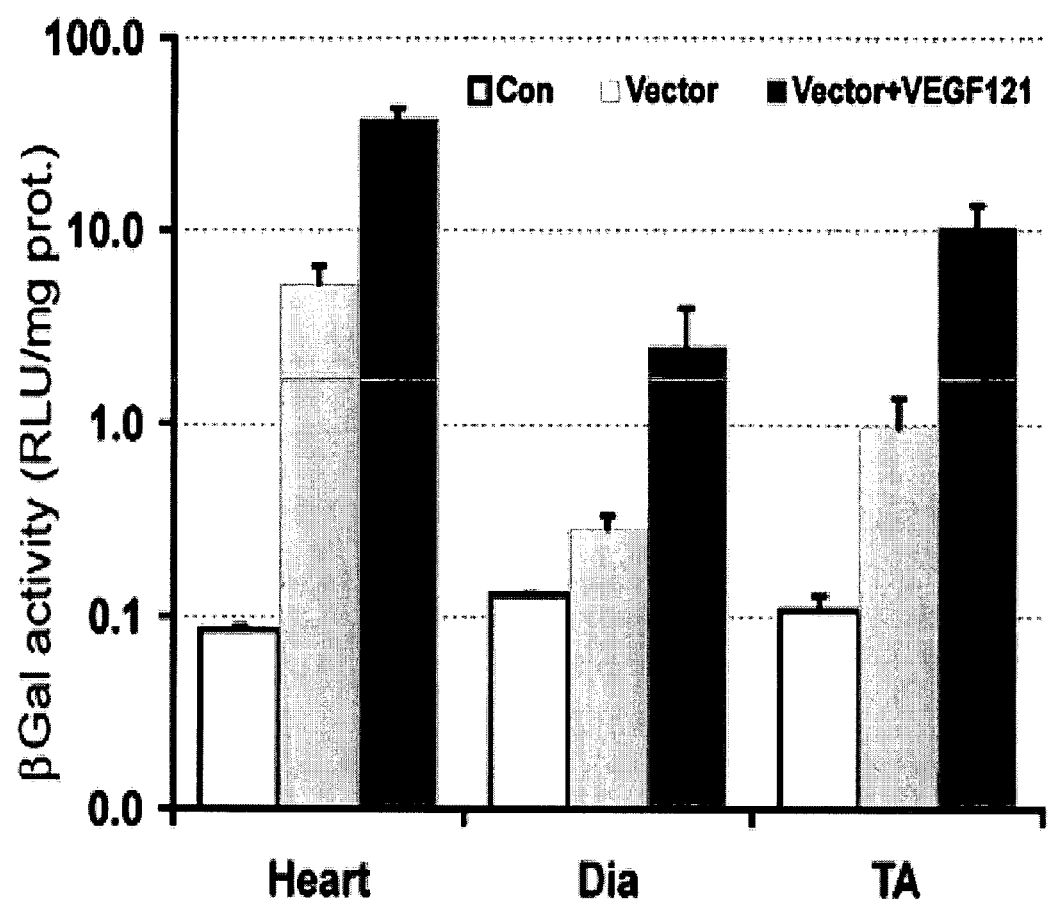
FIG. 9 is a graph that shows the results from Example 3 where rAAV6/CMV-lacZ plus VEGF-A121 were injected into the tail vein of mice and viral transduction in cardiac and skeletal muscle tissue was analyzed 11 days later for βgal activity.

This Examples describes systemic transduction of mice with AAV using VEGF-$A_{121}$ rather than VEGF-$A_{165}$. Mice were injected with $8 \times 10^{12}$ vg/kg of rAAV6/CMV-lacZ+/−260 ug/kg VEGF-$A_{121}$ via the tail vein 11 days prior to analysis of βgal activity. The results, presented in FIG. 9, show an approximately 10× increase in muscle transduction (e.g. in cardiac and skeletal muscle) by this shorter VEGF-A isoform.

EXAMPLE 4

Intravenous and Intra-Arterial Variable Timing Systemic Vector Delivery

Figure 10:
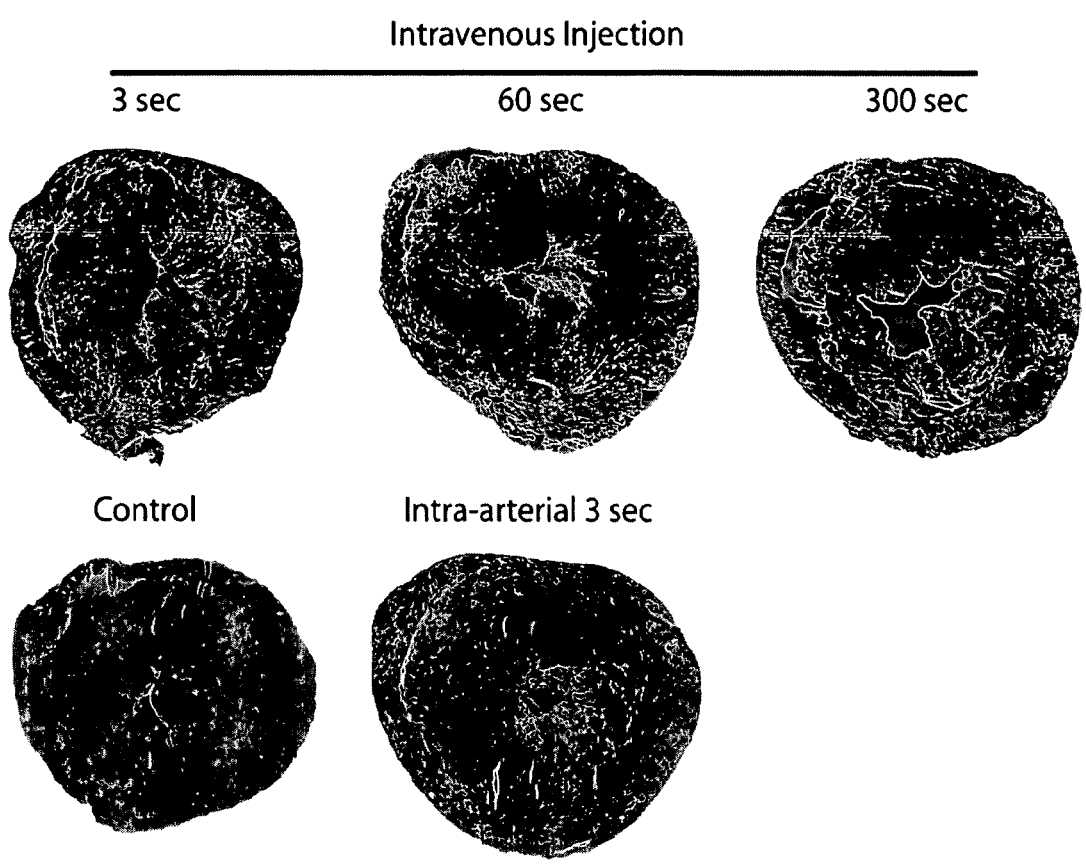
FIG. 10 shows the high level of beta-gal expression in cardiac tissue from the intravenous and intra-arterial administration of rAAV6-CMVlacZ described in Example 4 using different injection intervals (3 seconds, 60 seconds, or 600 seconds).

This Example describes success with both intravenous and intra-arterial systemic viral vector administration. Eight 10 week old C57B16 mice were injected with $3.3 \times 10^{13}$ vg/Kg (suspended in 250 microliters Ringers solution) of rAAV6-CMVlacZ via tail vein over different intervals (3 seconds, 60 seconds or 300 seconds) or via intra-femoral artery for 3 seconds. Neither injection used added VEGF (n=3 in each group). Eleven days after injection, mice were sacrificed, and tibialis anterior, Quadriceps, soleus, and heart muscles were dissected and then sectioned into 10 micron sections. As shown in FIG. 10, there was high level of beta-galactosidase expressions from CMV-lacZ cassettes in heart muscles using a 3 second infusion, as well as with 60 seconds, 300 seconds and with the femoral artery/3 seconds group. This Example shows that systemic transduction can be accomplished using multiple different delivery durations.

EXAMPLE 5

Enhancing Systemic Transduction with Empty AAV6 Capsids

Figure 11:
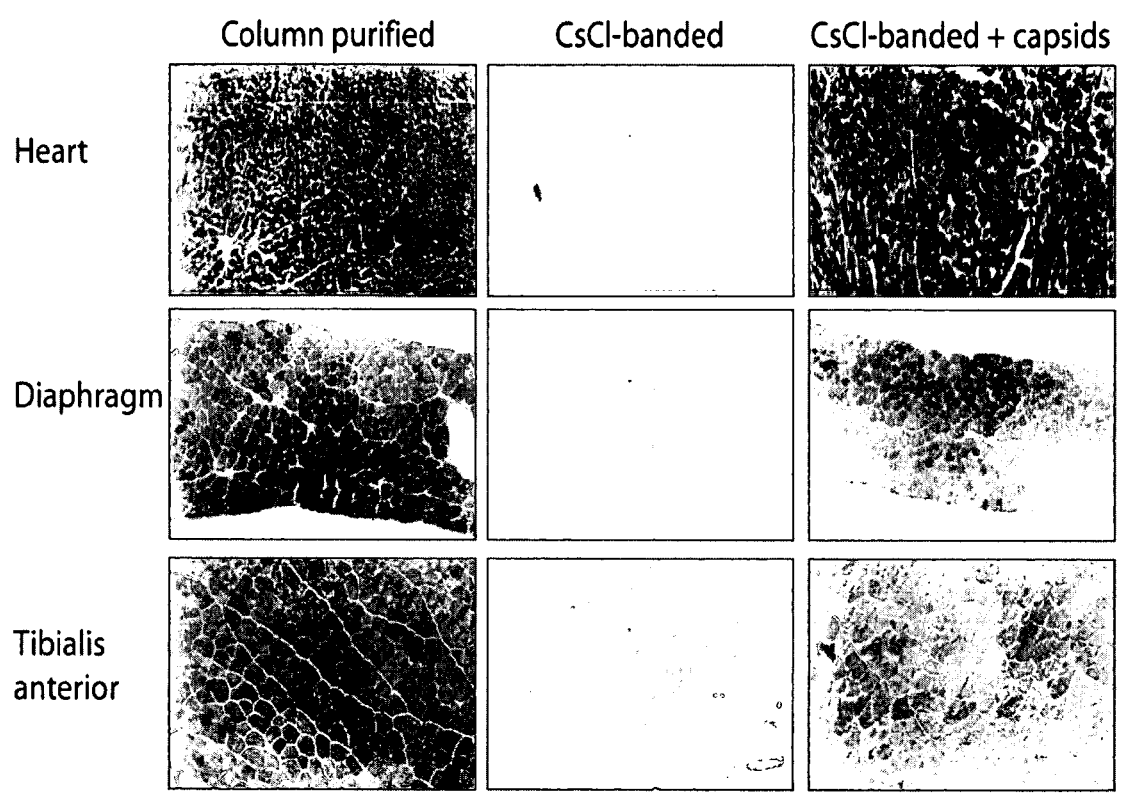
FIG. 11 shows results from Example 5, where preparation of approximately 95% empty AAV6 capsids ("column purified") were shown to enhance AAV6 viral transduction to a greater extent than a preparation of approximately 50% empty AAV6 viral capsids ('CsCl-banded").

This Example describes the use of empty AAV6 viral capsids (i.e. AAV6 particles without associated nucleic acid) to enhance systemic transduction with genome containing AAV6 particles. The vector used in this example was rAAV6-CMVlacZ. This vector was purified with heparin affinity chromatograph ("column-purified") to generate a preparation with approximately 95% empty AAV6 capsids, or was purified by cesium-chloride (CsCl-banded) to generate a preparation with approximately 50% empty AAV6 capsids. Wild type mice were intravenously injected with $1 \times 10^{12}$ pseudotype-6 AAV from either: 1) the "column-purified" preparation; 2) the "CsCl-banded" preparation, or 3) the "CsCl-banded" preparation combined with additional empty capsids taken from a preparation similar to the "column purified" preparation. Exogenous beta-galactosidase activity (darker gray) in the heart, diaphragm, and tibialis anterior was examined in cryosection of the mice after 12 days (see FIG. 11). This Figure shows greater systemic transduction with the 95% empty capsid preparations ("column purified" preparations), indicating that empty AAV capsids enhances systemic transduction of vectors.

EXAMPLE 6

Micro-Utrophin Treatment of mdx Mice

This Examples describes the treatment of mdx mice with micro-utrophin nucleic acid sequences. Mice were injected with $1 \times 10^{12}$ vector genomes (rAAV6:CK6-micro-utrophin, which is SEQ ID NO:1, shown in FIG. 13A) and analyzed at 6 weeks post injection. Immunofluorescence staining of a tibialis anterior muscle of the mdx mouse using an antibody against murine utrophin showed uniform staining. Immunofluorescence staining with α-syntrophin also shows micro-utrophin restores expression of utrophin and dystrophin associated proteins such as α-syntrophin. This Example could be repeated with the micro-utrophin sequence shown in FIG. 13B (SEQ ID NO:2).

EXAMPLE 7

Co-Delivery of IGF-1 and Dystrophin

This Examples describes the co-delivery of IGF-1 and dystrophin and the synergistic results achieved with such administration. In particular, this Example describes the delivery of IGF-1 and dystrophin to mdx (dystrophic) mice via AAV vectors.

Experimental Procedures

Isolation of Igf-I cDNA and rAAV Vector Construction

The 5'- and 3'-end of the Igf-I cDNA was amplified from a mouse muscle cDNA library using primers based on the published muscle Igf-I exon 3 sequence (MUSIGFI), together with library vector primers. The full-length mouse Igf-I cDNA was then isolated by recombinant PCR using primers based on sequence data from the 5'- and 3'-amplification products. Direct sequencing of PCR products showed that two alternative splice products of Igf-I, Ea and Eb were cloned. Igf-I Ea contains exons 1,3,4,6 (see SEQ ID NO:4 in FIG. 19), while Igf-I Eb contains exons 1,3,4,5,6 (see SEQ ID NO:3 in FIG. 19). Exon 5 in Igf-I Eb has an insert of 52 bp, which results in the alternative C-terminus of the peptide. Igf-I Eb is up-regulated in muscle subjected to stretch and therefore also referred to as mechano growth factor (MGF) (Yang et al., Journal of Muscle Research & Cell Motility 17:487-495, and McKoy et al., J Physiol 516 (Pt 2):583-592, herein incorporated by reference). Both muscle specific isoforms differ from the liver isoforms by using sequences encoded by exon 1 as a leader peptide in contrast to exon 2. The Igf-I Ea cDNA was then cloned into the EcoRI-HindIII site in the polylinker of pMCS-CMV (Stratagene, La Jolla, Calif.) that carried the CMV promoter and a bovine growth hormone polyadenylation site. The CMV promoter was removed with MluI and SacII, and replaced by the muscle-specific CK6 promoter. The complete expression cassette was then excised with NotI and moved into a pAAV vector backbone, containing serotype 2 inverted terminal repeats (Stratagene). The micro-dystrophin cDNA (DR4-R23/DCT, see FIG. 14A) is a truncated version of the full-length dystrophin cDNA and was generated by introducing deletions between repeat 4 and repeat 23 within the rod domain, and a deletion of the C-terminal domain (see Harper et al., Nature Medicine 8:253-261, 2002, herein incorporated by reference). The micro-dystrophin cDNA was cloned into the EagI site of the pDD344 plasmid.

rAAV Production and Quantitation

For production of AAV pseudotype 6 vectors, HEK293 cells were co-transfected with 10 mg recombinant AAV vector and 20 mg helper plasmid pDGM6 (Gregorevic et al., Nat Med. August 2004; 10(8):828-34, herein incorporated by reference in its entirety) using the calcium phosphate-DNA precipitation method. Viral vector purification was performed as described (Blankinship et al., Mol Ther. October 2004; 10(4): 671-8, herein incorporated by reference in its entirety). In brief, transfected cells and medium were homogenized through a microfluidizer (Microfluidics, Newton, Mass.) and cleared through a 0.22 mm filter. Vector particles were subsequently purified by affinity chromatography over a HiTrap heparin column (Amersham, Piscataway, N.Y.) using an AKTApurifier 10 high pressure liquid chromatography (HPLC) machine (Amersham), and dialyzed against physiological Ringer's solution. The vector titer was determined by quantitative slot blot analysis, using plasmid standards derived from a NotI or MscI digest of pAAV-Igf-I or pAAV-mdys, respectively. Vector genomes were hybridized with transgene-specific probes labeled with the CDP-Star kit (Amersham, Piscataway, N.J.) and visualized with a chemoluminescence imager (GeneGnome, Syngene, Frederick, Md.).

Intramuscular Injection

All experiments used male wild-type C57BL/10, or dystrophic mdx mice according to the guidelines of the University of Washington Institutional Animal Care and Use Committee (IACUC). Nine month-old mdx male mice were anesthetized with either 2,2,2-tribromoethanol (Sigma, St. Louis, Mo.) or isoflurane (Abbott Laboratories, Chicago, Ill.) such that they were non-responsive to tactile stimuli, and the tibialis anterior (TA) hindlimb muscles were surgically exposed by performing a small skin incision parallel to the muscle. Viral vector (1-2×10$^{10}$ vg) in 30 ml physiological Ringer's solution was then carefully injected into the muscle via a Hamilton syringe equipped with a 32-gauge needle. After injection, the skin incision was closed with Nexaband surgical grade adhesive (World Precision Instruments, Inc., Sarasota, Fla.). Controls for all experiments consisted of sham injections with physiological Ringer's solution.

Functional Analysis

At four months after vector administration, the contractile properties of the muscles of treated and control mice were tested as described (see DelloRusso, et al., Journal of Muscle Research and Cell Motility 22:467-475, 2001, herein incorporated by reference). In brief, mice were anesthetized with 2,2,2-tribromoethanol (Sigma, St. Louis, Mo.) to isolate and attach the distal tendon of the TA muscles to a dual-mode servomotor, and position electrodes adjacent to the motor nerve. The optimal muscle length (Lo) and the maximum isometric force were determined for each muscle sample. To assess the susceptibility of muscles to contraction-induced injury, muscles were then maximally stimulated and stretched twice from Lo through 40% of muscle fiber length. Maximum isometric force was measured after each lengthening contraction and reported as a percentage of initial maximum isometric force. The forces produced after LC1 and LC2 were used to model the ability of muscles to resist injury. At the completion of testing, the muscles were excised, weighed and prepared for biochemical and histological analysis.

RNA and DNA Isolation and Quantitation

For biochemical analysis, muscles were frozen in liquid nitrogen for storage at −80° C. until use. Muscles were homogenized (OMNI 5000, OMNI International) in lysis buffer (RNeasy, Qiagen, Sanita Clarita, Calif.) and then treated with proteinase K (20 mg/ml) to remove connective tissue and collagen. Residual debris was pelleted and the clear supernatant was loaded on a RNA purification column for further extraction according to the manufacturer's instructions (RNeasy, Qiagen). Before washing and eluting the RNA from the columns, an on-column DNase 1 digestion was performed to ensure complete removal of genomic and residual vector DNA (Qiagen). 500 mg total RNA of each sample was electrophoresed to confirm RNA integrity. One mg total RNA of each sample was reverse transcribed into cDNA. Igf-I mRNA transcripts were then quantified by real-time PCR, using the Applied Biosystems 7700 sequence detection system. cDNA templates were diluted 1:10, 1:100 and 1:1000 and each reaction was run in duplicate for Igf-I and GAPDH primer sets and probes, respectively. Expression levels of Igf-I transcripts were determined relative to GAPDH transcripts.

DNA was isolated from an aliquot of the same muscle sample taken after tissue lysis and extracted with a standard phenol/chloroform extraction protocol. Residual RNA was removed by RNase A treatment (50 mg/ml). Vector genomes were quantified by real-time PCR, using the Applied Biosystems 7700 sequence detection system. DNA samples were diluted to a final concentration of 100 ng, 10 ng and 1 ng and each reaction was run in duplicate by using DNA specific Igf-I primers. DNA vector persistence was determined by relative quantitation of samples of unknown concentration to a DNA standard curve.

Immunohistochemical Analysis

Muscles embedded in O.C.T. (Sakura Finetek, Torrance, Calif.) were frozen in melting isopentane, and stored at −80° C. until use. For basic morphological evaluation, frozen cryosections were treated with hematoxylin and eosin-phloxine. To detect dystrophin expression, serial cryosections were incubated with a primary antibody against the N-terminus of dystrophin. For immunofluorescence analysis, sections were then stained with FITC-conjugated goat anti-rabbit (Alexa 488, Molecular Probes) secondary antibody, washed and mounted with Vectashield mounting media (Vector Labs, Burlingame, Calif.). For immunohistochemical reaction, sections were treated with biotin blocking agent (Molecular probes, Eugene, Oreg.) and subsequently stained with the Vector ABC kit (Vector Labs). Sections were counterstained with a 0.5% Neutral Red solution and mounted with Permount mounting media.

Image Processing and Quantitative Measurements

Brightfield and fluorescence images of sections were acquired using a Spot-2 and JVC camera respectively via a Nikon E1000 microscope (Melville, N.Y.). Montage images of entire muscle cross sections were graduated using MONTAGE EXPLORER software (Syncroscopy, Frederick, Md.) to control stage position during image acquisition. Image analysis was completed using IMAGEPRO software (Media Cybernetics, Silver Spring, Md.) with manual on-screen selection of functions. Montage images of hematoxylin and eosin-phloxine stained sections were overlayed with a mask that randomly chose four 400 mm2 microscopic fields per muscle cross section. These fields were used to manually determine the percentage of centrally located myofibers, the average fiber diameter, obtained from the narrowest fiber diameter of each muscle fiber, and the number of muscle fibers per defined area. Montage images of dystrophin immunohistochemical staining were used to determine the percentage of dystrophin-positive area of muscle cross sections relative to total cross sectional area. Dystrophin-positive area was defined as the area within dystrophin-positive myofibers. This area excludes dystrophin-negative myofibers, interstitial space, connective tissue, blood vessels and nerves. Statistical analyses were performed by ANOVA using STATVIEW software (SAS Institute, Cary, N.C.).

Results

Igf-I and Dystrophin Expression

To characterize Igf-I expression in normal and dystrophin-deficient muscle, mRNA levels of the Igf-I Ea and Igf-I Eb isoforms were measured by quantitative PCR. Primer pairs were designed to uniquely detect Igf-I Eb or both, Igf-I Ea and Igf-I Eb. Both isoforms were expressed in wild-type and mdx muscles of 9-13 month old mice, unlike previous data that suggested that Igf-I Eb is not expressed in mdx muscles (Goldspink, et al., J of Physiology 495:162-163, 1996). No significant difference was detected in the Igf-I mRNA expression levels of both isoforms between mdx and wild-type muscles in the tested age group. The Igf-I Eb isoform was expressed at much lower levels than Igf-I Ea, which is in accordance with previous publications, showing that Igf-I Eb is mainly generated in muscles subjected to stretch (see Yang et al. and McKoy et al. above).

To study the effects of co-delivering both Igf-I and dystrophin to the muscles of dystrophic mdx mice, rAAV vectors were generated that carried expression cassettes in which the muscle-specific creatine kinase promoter/enhancer (CK) drove either the micro-dystrophin (DR4-R24/DCT) or the muscle-specific Igf-I cDNA (Igf-I-Ea) (see FIG. 14A). TA muscles of nine month old mdx mice were injected either with each vector separately, or in combination.

Four months post-injection, dystrophin expression was analyzed by immunohistochemical staining of muscle cross sections using an antibody against the N-terminal domain of dystrophin. AAV-mdys injected and AAV-mdys/Igf-I co-injected muscles revealed widespread distribution of dystrophin-positive fibers throughout the muscles. The percentage of dystrophin expressing fibers averaged 40% of the total cross sectional area (FIG. 14B). AAV-Igf-I and untreated control muscles contained only a few revertant, dystrophin-positive fibers, that accounted for less than 5% of the total cross sectional area (FIG. 14B).

To examine Igf-I expression, a quantitative PCR assay was performed to measure Igf-I mRNA levels in AAV-Igf-I injected, and AAV-mdys/Igf-I co-injected, muscles relative to untreated mdx and wild-type muscles. AAV-Igf-I injected mdx muscles demonstrated 50-100 fold higher expression of Igf-I MRNA than mdx control muscles at four months post-injection. In contrast, co-injection of AAV-mdys/Igf-I resulted in 200-400 fold higher expression of Igf-I mRNA than in mdx control muscles four months following the injection. The 4-5 fold increase of Igf-I expression over time in AAV-mdys/Igf-I co-treated versus AAV-Igf-I treated animals suggested that dystrophin expression protects muscle fibers from degeneration, and as a result from loss of viral vector DNA. To test this hypothesis, vector DNA persistence was examined in AAV-Igf-I treated, and in AAV-mdys/Igf-I co-treated, animals. Quantitation by real-time PCR detected ~$5 \times 10^4$ genomes/mg total DNA in AAV-Igf-I injected muscles. In agreement with mRNA expression analysis, muscles co-treated with AAV-mdys/Igf-I demonstrated a 4-5 fold increase in vector genomes, such that the average injected muscle showed ~$2.5 \times 10^5$ genomes/mg total DNA.

Functional Measurements

Figure 15:
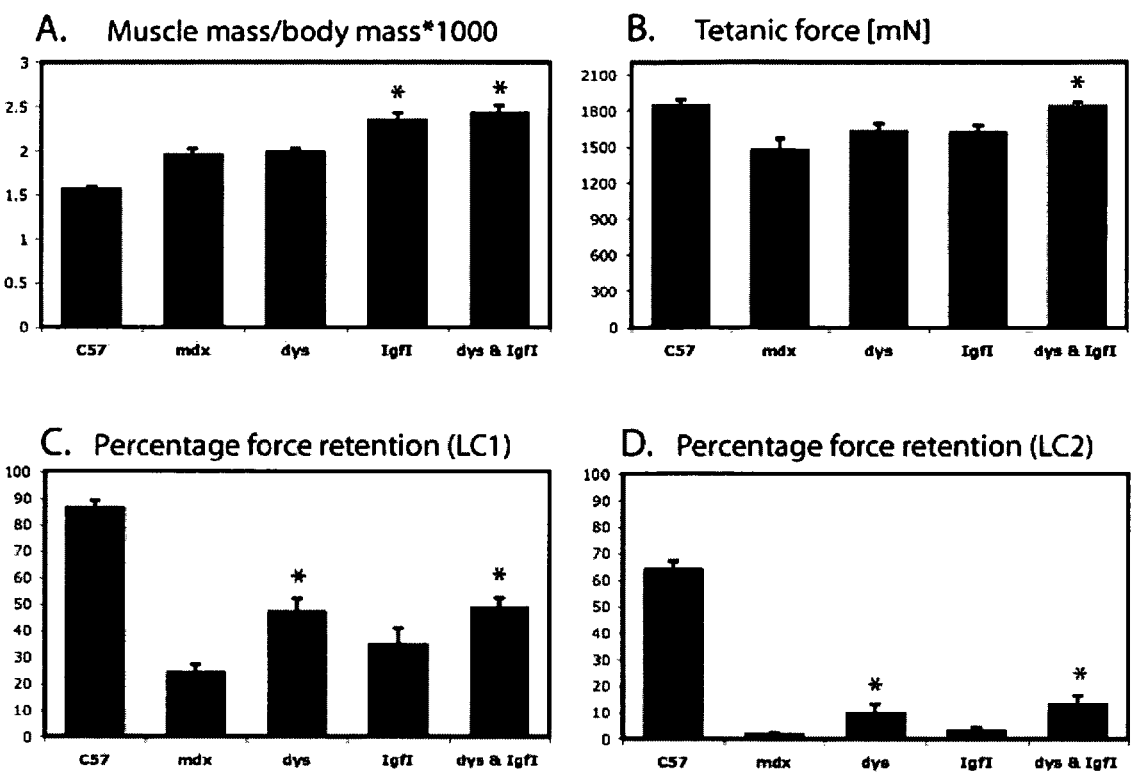
FIG. 15 shows results for the mice treated in Example 7, including: A) muscle mass/body mass, B) tetanic force measurements; C) percentage force retention (LC1); and D) percentage force retention (LC2).

Physiological properties of TA muscles injected with AAV-mdys, AAV-Igf-I or AAV-mdys/Igf-I were analyzed four months post-injection, and compared with the muscles of mdx and wild-type control animals. Muscles injected with AAV-Igf-I and AAV-mdys/Igf-I demonstrated a significant increase in muscle size and mass relative to mdx and AAV-mdys treated muscles. When muscle mass was normalized to whole body mass, mean values were increased 17% for AAV-Igf-I treated and 19% for AAV-mdys/Igf-I co-treated muscles compared with control mdx muscles (FIG. 15A). In comparing muscle mass to maximum force output, it was observed that AAV-Igf-I treatment resulted in a mean increase in maximum isometric force generation of 9% that was not significantly different from AAV-mdys and sham injected muscles. However, AAV-mdys/Igf-I co-treatment resulted in a significant increase of 20% in maximum isometric force generation (FIG. 15B). When isometric force values were normalized to cross-sectional area, no significant difference was observed between all treated groups and mdx animals. Thus, increased muscle masses due to Igf-I treatment translated into increased maximum force values in AAV-mdys/Igf-I co-treated, and to a lower extent in AAV-Igf-I treated, animals; however deficiencies in maximum force per cross sectional area were not corrected by Igf-I treatment.

Muscles from control and treated groups were also subjected to lengthening under maximum contraction to analyze muscle susceptibility to mechanical damage. All AAV-mdys treated and AAV-mdys/Igf-I co-treated animals demonstrated a significant protection from contraction-induced injury (FIG. 15C, 15D). After the first lengthening contraction, AAV-mdys injected and AAV-mdys/Igf-I co-injected muscles displayed force generating capacities that were ~47% and ~49% of the values before the contractions, compared with ~24% in mdx and ~86% in wild-type animals (FIG. 15C). AAV-Igf-I treated animals retained ~35% of the initial force generating capacity after the first lengthening contraction; however these values were not significantly different from mdx animals. After the second lengthening contraction, AAV-Igf-I treated muscles were as susceptible to muscle damage as mdx control muscles and showed a force generating retention of only 3% (FIG. 15D). In contrast, AAV-mdys treated, and AAV-mdys/Igf-I co-treated, animals demonstrated a statistically significant 10% and 13% retention of force generation, compared to 2% in mdx and 64% in wild-type animals. The values of AAV-mdys treated, and the AAV-mdys/Igf-I co-treated animals represent a 40% correction of the functional difference between mdx and wild-type muscles.

Histological Analysis

Muscle sections were stained with hematoxylin and eosin and analyzed for morphological characteristics of mdx pathology. Overall, AAV-mdys expressing fibers displayed no evidence of necrosis, while fibers that did not express dystrophin displayed features of dystrophic pathology, such as loss of membrane integrity, mononuclear cell infiltration and on occasion a staining pattern indicative of necrosis. Detailed morphological analysis of random fields of muscle cross sections demonstrated that 42% of nuclei were centrally located in mdx muscles, while less than 1% of nuclei were centrally located in wild-type muscles. AAV-Igf-I treated muscles showed an average percentage of central nucleation similar to mdx untreated muscles. In contrast, AAV-mdys treated, and AAV-mdys/Igf-I co-treated animals revealed a 19% reduction in central nucleation relative to mdx, giving further evidence for the presence of fewer cycles of degeneration and regeneration in AAV-mdys treated TA muscles (FIG. 16A). When central nucleation was analyzed selectively in dystrophin-expressing fibers, the percentage of centrally located nuclei decreased an additional 2-3% in comparison to random field analysis. Since reliable methods to directly visualize Igf-I expression in vivo are not available, analysis was limited to analyzing random fields, containing Igf-I transduced and non-transduced myofibers. The extent of transduction from one muscle to another could therefore vary and it remains to be determined precisely how Igf-I treatment influences myofiber morphology.

Overall analysis of AAV-Igf-I treated and AAV-mdys/Igf-I co-treated animals demonstrated an increase in total cross sectional area (CSA) compared with untreated mdx and AAV-mdys treated animals. This increased CSA was reflected by the muscle mass analysis (FIG. 15A). It was then analyzed whether muscle hypertrophy resulted from myofiber enlargement or an increase of total fiber number by analyzing fiber diameter and the number of fibers per defined unit area (FIG. 16B, 16C). AAV-Igf-I and AAV-mdys/Igf-I treatment both resulted in a ~11% and ~9% decrease in the total number of myofibers per unit area, which correlated with an increase in mean fiber diameter in AAV-Igf-I treated, and to a lesser extent in AAV-mdys/Igf-I co-treated, muscles compared with untreated mdx muscles. In addition, AAV-Igf-I and AAV-mdys/Igf-I demonstrated a higher absolute number of large muscle fibers than did AAV-mdys and mdx muscles (FIG. 16C). These results indicated that muscle fiber hypertrophy contributed to the increased muscle mass in AAV-Igf-I treated, and to a lesser extent in AAV-mdys/Igf-I, co-treated mdx muscles. AAV-mdys treated muscles demonstrated a small increase in mean fiber diameter that probably reflects a reduction in myofiber degeneration and thus the presence of fewer small caliber regenerating fibers (FIG. 16C). To determine the extent of muscle hyperplasia, the total number of muscle fibers per unit area was compared to the total number of muscle fibers per muscle cross section. Since it is difficult to distinguish between branched old and regenerated new muscle fibers due to the extensive muscle degeneration and regeneration that occurs in young adult mdx muscles, a precise estimate of absolute myofiber number was not possible in 13 month old mdx muscles. However, the total number of myofiber segments observed in thin sections increased to a significant extent in AAV-mdys/Igf-I, and to a lower extend in AAV-Igf-I treated, in comparison to mdx animals. These observations suggest that muscle enlargement after Igf-I treatment of nine month-old mdx mice results from a combination of hypertrophy and hyperplasia in AAV-mdys/Igf-I and AAV-Igf-I treated animals.

The results presented above show the synergistic affect of combined Igf-I and dystrophin treatment. AAV-Igf-1 treated muscles displayed an increase in muscle mass, but were not significantly protected from contraction-induced injuries (FIG. 15C). In contrast, AAV-uDys treated animals demonstrated increased protection from contraction-induced injury, but did not display increases in mass or specific force. However, the combined treatment of both AAV-Igf-I and AAV-uDys showed an increase in muscle mass and strength together with protection from contraction-induced injury, indicating that co-treatment is more beneficial that treatment with either protein alone.

EXAMPLE 8

Intravenous Administration of Igf-1 to Treat Symptoms of Aging

This Example describes administration of Igf-1 to old mice in order to reduce muscle wasting type symptoms in old mice. Old mice (approximately 20 months old) were administered $1 \times 10^{12}$ vg/kg rAAV6-CK-Igf-1 or rAAV6-CMV-Igf-1 and were examined approximately 7 months after administration. FIG. 17A shows intravenous administration of rAAV6-Igf-1 vectors to old mice results in increased body mass consistent with increased muscle mass. In particular, FIG. 17A shows the change in body mass for the control was approximately 3%, while the mice receiving Igf-1 was about 21% (CK promoter) and 18% (CMV promoter). FIG. 17B show the change in Tibialis anterior (hindlimb) muscle mass for the control was about 48%, while mice receiving Igf-1 was about 52% (for both the CK and CMV promoters). FIG. 18A shows intravenous administration of rAAV6-Igf-1 vectors to old mice results in increased muscle strength and performance. In particular, FIG. 18A shows the tibialis anterior (TA) muscles of treated old mice generate increased force compared with the muscles of untreated mice. FIG. 18B shows that the muscles of treated mice display increased force output over a protocol of repetitive stimulation and at recovery.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, and molecular biology or related fields are intended to be within the scope of the following claims.

We claim:

1. A method of systemic transduction of skeletal muscle tissue or heart tissue comprising;
   a) providing;
      i) a first composition comprising adeno-associated vectors, wherein said adeno-associated vectors comprise a nucleic acid sequence of interest,
      ii) a second composition comprising a systemic transduction enhancing agent, wherein said systemic transduction enhancing agent comprises empty adeno-associated viral capsids, and wherein at least 50% of the adeno-associated viral capsids in said second composition are said empty adeno-associated viral capsids, and iii) a subject comprising a first type of extravascular tissue, wherein said first type of extravascular tissue is skeletal muscle tissue or heart tissue; and b) administering said first and second compositions systemically to said subject, under conditions such that said first type of extravascular tissue is transduced by said adeno-associated vectors, wherein said first and second compositions are: i) administered simultaneously; ii) are administered within 5 minutes of each other, or iii) mixed together prior to said administering.

2. The method of claim 1, wherein at least approximately 95% of the adeno-associated viral capsids in said second composition are said empty adeno-associated viral capsids.

3. The method of claim 1, wherein said first and second compositions are administered simultaneously or within 5 minutes of each other.

4. The method of claim 1, wherein said first and second compositions are mixed together prior to said administering.

5. The method of claim 1, wherein said first or second composition further comprises heparin.

6. The method of claim 1, wherein said first type of extravascular tissue is heart tissue.

7. The method of claim 1, wherein said first type of extravascular tissue is skeletal muscle tissue.

8. The method of claim 1, wherein said adeno-associated vectors comprise an AAV6 capsid.

9. The method of claim 1, wherein said first composition is a vasodilating agent-free composition.

10. The method of claim 1, wherein said second composition is a vasodilating agent-free composition.

11. The method of claim 1, wherein said first composition comprises less than $1 \times 10^{12}$ adeno-associated vectors per milliliter.

12. The method of claim 1, wherein said nucleic acid sequence of interest encodes a micro-dystrophin, micro-utrophin, micro-dystrophinlutrophin hybrid, or insulin-like growth factor 1 (Igf-1).

13. The method of claim 1, wherein said nucleic acid sequence of interest is a reporter gene.

14. The method of claim 1, wherein said administering is without a systemic administration aid.

* * * * *